(12) United States Patent
Atmanli et al.

(10) Patent No.: US 10,900,070 B2
(45) Date of Patent: Jan. 26, 2021

(54) MULTIPLEX ANALYSIS OF GENE EXPRESSION IN INDIVIDUAL LIVING CELLS

(71) Applicant: THE GENERAL HOSPITAL CORPORATION, Boston, MA (US)

(72) Inventors: Ayhan Atmanli, Somerville, MA (US); Ibrahim J. Domian, Swampscott, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 257 days.

(21) Appl. No.: 15/570,514

(22) PCT Filed: Apr. 29, 2016

(86) PCT No.: PCT/US2016/029972
§ 371 (c)(1),
(2) Date: Oct. 30, 2017

(87) PCT Pub. No.: WO2016/178953
PCT Pub. Date: Nov. 10, 2016

(65) Prior Publication Data
US 2018/0142284 A1 May 24, 2018

Related U.S. Application Data

(60) Provisional application No. 62/155,945, filed on May 1, 2015.

(51) Int. Cl.
| | |
|---|---|
| *C12Q 1/68* | (2018.01) |
| *C12Q 1/6818* | (2018.01) |
| *C07H 21/02* | (2006.01) |
| *C07H 21/04* | (2006.01) |
| *C12Q 1/6841* | (2018.01) |
| *C12N 15/10* | (2006.01) |
| *C12N 15/70* | (2006.01) |
| *C12Q 1/6834* | (2018.01) |
| *G01N 33/58* | (2006.01) |

(52) U.S. Cl.
CPC ........... *C12Q 1/6818* (2013.01); *C07H 21/02* (2013.01); *C07H 21/04* (2013.01); *C12N 15/1086* (2013.01); *C12N 15/70* (2013.01); *C12Q 1/6834* (2013.01); *C12Q 1/6841* (2013.01); *G01N 33/58* (2013.01); *C12Q 2522/101* (2013.01); *C12Q 2563/107* (2013.01); *C12Q 2563/119* (2013.01)

(58) Field of Classification Search
None
See application file for complete search history.

(56) References Cited

U.S. PATENT DOCUMENTS

| | | |
|---|---|---|
| 2005/0260660 A1 | 11/2005 | Van Dongen et al. |
| 2010/0209933 A1* | 8/2010 | McReynolds ...... G01N 33/5308 435/5 |

OTHER PUBLICATIONS

Bao et al., "Fluorescent Probes for Live-Cell RNA Detection", Annual Review of Biomedical Engineering 11:25-47 (2009).

* cited by examiner

*Primary Examiner* — James Martinell
(74) *Attorney, Agent, or Firm* — Nixon Peabody LLP; David S. Resnick; Susanna C. Benn

(57) ABSTRACT

The technology as disclosed herein relates to methods, compositions and kits for multiplex measuring levels of expression of target RNA species (e.g., mRNA and non-coding RNAs) in single, living cells. Aspects of the invention relate to, in part, a duplex-binding protein which is labeled with a FRET dye, and a RNA-binding probe, which comprises a spectrally paired FRET dye and specifically hybridizes to a target RNA. When the RNA-binding probe binds to a target RNA, a duplex is formed, which is allows binding of the duplex-binding protein bringing the two FRET dyes into close proximity and allowing fluorescence resonance energy transfer (FRET) reaction and a detectable change in fluorescence, which determines the amount of target RNA species in the living cell. Aspects of the invention also include, kits, vectors and polynucleic acid sequences of the duplex-binding protein and RNA-binding probes disclosed herein, and cell and cell lines comprising the same.

12 Claims, 16 Drawing Sheets
Specification includes a Sequence Listing.

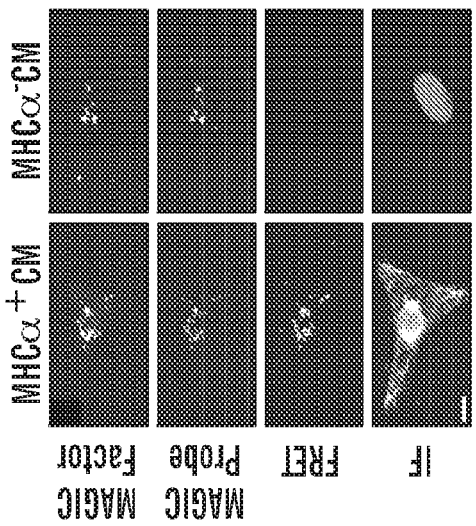
FIG. 7B
FIG. 7C
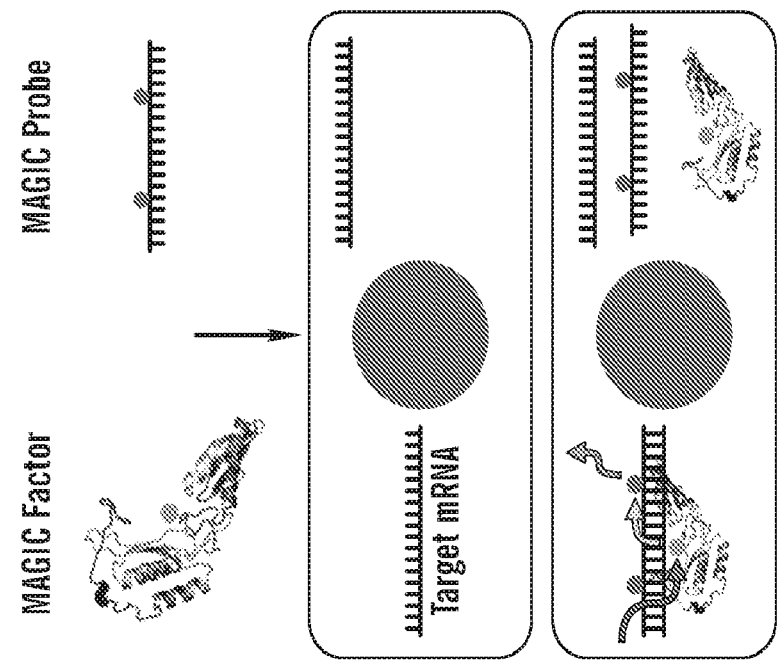
FIG. 7A

[   β1   ]            [   β2   ]       [   β3   ]
            [   REGION 2   ]
```

FIG. 13 (cont.)

```
         50                60                70
S A D G F K I T K A Q H L A A S K A E E T M Y   - SEQ ID NO: 3
E G E G N G K K V S K K R A A E K M L V E L Q K - SEQ ID NO: 4
R G T G N S K K L A K R N A A Q A L F E L L E A - SEQ ID NO: 5
E G E G R S K K E A K N A A A K L A V E I L N K - SEQ ID NO: 6
I G T G S T K Q E A K Q L A A K L A Y L Q I L S - SEQ ID NO: 7
T G E G T S K K L A K H R A A E A A I N I L K A - SEQ ID NO: 8
T G K G A S K K Q A K R N A A E K F L A K F S N - SEQ ID NO: 9
L G E G P S K A T P K Q K A A E F A L N I L R G - SEQ ID NO: 10
T G S G T S K Q V A K R V A A E K L L T K F K T - SEQ ID NO: 11
T G Q G P S K A A K H K A A E V A L K H L L K G - SEQ ID NO: 12
I G S G T S K K L A K R N A A A K M L L R V H T - SEQ ID NO: 13
G T A S - S K K L A K N K A A R A T L E I L I P - SEQ ID NO: 14
R G W C K N K K V G K Q L A S Q K L L Q L L H P - SEQ ID NO: 15
P A E A G S K K V A K Q D A A M K A M T I L L E - SEQ ID NO: 16
S V S A P S K K V A K Q M A A E E A M K A L H G - SEQ ID NO: 17
E G S G P T K K K A K L H A A E K A L R S F V Q - SEQ ID NO: 18
E G S G R N K K L A K A R A A Q S A L A A I F N - SEQ ID NO: 19
L G Q G R S K K V A R I E A A T A L R S F I Q   - SEQ ID NO: 20
D G T G P S K A T A K N A A A K A A L A S L C N - SEQ ID NO: 21
K G V G R S Y K I A K S A A A R R A L R S L K A - SEQ ID NO: 22
T G V G R N I K I A G I R A A E N A L R D K K M - SEQ ID NO: 23
V G T G S S K R K A E Q A A A E Q A L K K L E L - SEQ ID NO: 24
L G E G K S K K E A E Q R A A E L I K L L E E   - SEQ ID NO: 25
L P G F F N K K A A E Q S A A E V A L R E L A K - SEQ ID NO: 26
A - A T R T K D A E I S A G R T A L L A I Q S   - SEQ ID NO: 27
- G - G - S K K - A K - - A A E - A L - - L - - - SEQ ID NO: 28
- G - G - S - - - A - - - A A - - A L - - L - - - SEQ ID NO: 29
- - - - - - K K - - A - K - - - - - - - - - - - - SEQ ID NO: 30
- - - - - - K K - - - - - - - - - - - - - - - - - SEQ ID NO: 31
```

β3 — α2

REGION 3

MULTIPLEX ANALYSIS OF GENE EXPRESSION IN INDIVIDUAL LIVING CELLS

CROSS REFERENCE TO RELATED APPLICATIONS

This application is a 371 National Phase Entry of International Patent Application No. PCT/US2016/029972 filed on Apr. 26, 2016 which claims benefit under 35 U.S.C. § 119(e) of U.S. Provisional Application No. 62/155,945 filed on May 1, 2015, the contents of which are incorporated herein by reference in their entirety.

SEQUENCE LISTING

The sequence listing of the present application has been submitted electronically via EFS-Web as an ASCII formatted sequence listing with a file name "030258-085031-PCT_SL", creation date of Oct. 17, 2017 and a size of 43,417 bytes. The sequence listing submitted via EFS-Web is part of the specification and is herein incorporated by reference in its entirety.

FIELD OF THE INVENTION

This invention generally relates to the field of biotechnology and more particularly to real time detection and monitoring of multiple nucleic acids expressed in a living cell using fluorescence resonance energy transfer (FRET).

BACKGROUND OF THE INVENTION

Understanding the interactions between the components of a biological system and how they give rise to function is a key aim when studying systems biology. Most of our current information on the activation of downstream genes in many signal transduction cascades is derived from microarray data or protein gene reporter assays (Pepperkok, R. & Ellenberg, J. High-throughput fluorescence microscopy for systems biology. Nat Rev Mol Cell Biol 7, 690-696 (2006)). Microarray approaches are able to provide population or "census" information for the behavior of millions of cells. However each cell is most likely engaged in a different phase of response to the signaling cascade and what is measured is a more global and general picture. Within this mosaic picture lies information as to when specific cells are engaged in specific phases of their gene response. Theoretically this can be temporally related to when the pathway is activated and assist in building mechanistic models of how such dynamic signal transduction cascades function. However accurate temporal information on such transcriptional response is masked in the "noise" or stochastic variations of the microarray data.

Exploring macromolecules in their natural environment with high spatial and temporal resolution has become possible through the use of fluorescence-based imaging assays in living cells (Pepperkok, R. & Ellenberg, J. High-throughput fluorescence microscopy for systems biology. Nat Rev Mol Cell Biol 7, 690-696 (2006), Bastiaens, P. I. & Pepperkok, R. Observing proteins in their natural habitat: the living cell. Trends Biochem. Sci. 25, 631-637 (2000); Meyer, T. & Teruel, M. N. Fluorescence imaging of signaling networks. Trends Cell Biol. 13, 101-106 (2003); Wouters, F. S., Verveer, P. J. & Bastiaens, P. I. Imaging biochemistry inside cells. Trends Cell Biol. 11, 203-211 (2001). In principle, they can be used to explore proteins in their natural habitat, interrogating their biochemical interactions. However this has not been easily extended to imaging dynamics of gene expression, for example through observation of transcription of messenger RNA. Examining this activity on the single cell level would permit the temporal relationship between activation of a signal transduction cascade (the biochemical events) and a specific transcriptional response to be accurately related.

Though this has been attempted with gene reporter assays such as fluorescent protein or luciferase assays, what is measured is the translational and not transcriptional readout of a single gene in what is most likely hundreds of genes engaged in a transcriptional response. The kinetics of gene expression however cannot be directly inferred by the appearance of a protein as there is a lag between transcription of mRNA and translation to protein. Since translation is delayed from transcription, the ability to draw exact temporal relationships between genes may remain unsuccessful. As a result despite copious amounts of data, the temporal relationship between functional pathways activation remains unclear. These deficiencies have especially been observed when studying temporal relationships between immune pathways and inflammatory pathways (Karin, M. Nuclear factor-kappaB in cancer development and progression. Nature 441, 431-436 (2006); Karin, M., Lawrence, T. & Nizet, V. Innate immunity gone awry: linking microbial infections to chronic inflammation and cancer. Cell 124, 823-835 (2006)). To date, no genetically encoded tag exists that could be used to label mRNA in a similar way as GFP and comparable proteins.

High content screening allows for the evaluation of multiple biochemical and morphological parameters in cellular systems, if biological readouts in the system are amenable to quantitative data collection in vivo. By combining the imaging of single cells with image analysis algorithms, individual components of the biological system are assigned quantitative properties (Genovesio, A., Belhassine, Z. & Olivo-Marin, J. Adaptive gating in Gaussian Bayesian multi-target tracking. Image Processing, 2004. ICIP'04. 2004 International Conference on 1 (2004), Bork, P. & Serrano, L. Towards cellular systems in 4D. Cell 121, 507-509 (2005); Genovesio, A., Zhang, B. & Olivo-Marin, J. Interacting multiple model based method to track moving fluorescent biological spots. Biomedical Imaging: Macro to Nano, 2004. IEEE International Symposium on, 1239-1242 (2004); Olivo-Marin, J. Extraction of spots in biological images using multiscale products. Pattern Recognition 35, 1989-1996 (2002)). Thus, the nature of the dynamic system can be modelled, permitting true systems biology.

There are reports of collecting quantitative information for protein interactions in signal transduction pathways in living cells using image-based approaches (e.g., see, Starkuviene, V. High-content screening microscopy identifies novel proteins with a putative role in secretory membrane traffic. Genome Res. 14, 1948-1956 (2004); Liebel, U. A microscope-based screening platform for large-scale functional protein analysis in intact cells. FEBS Lett. 554, 394-398 (2003); Bastiaens, P. I. & Pepperkok, R. Observing proteins in their natural habitat: the living cell. Trends Biochem. Sci. 25, 631-637 (2000)).

However, in vivo single cell based transcriptional information, in functioning living cells, at the mRNA level that reports quantitative levels of transcriptional activity in a signal transduction cascade, in response to a given stimulus or in differing genetic backgrounds, is not yet a reality. Achieving this goal will enable the accurate modeling of transcription in signal transduction cascades.

The ability to follow and track individual mRNA complexes in vivo (i.e., in a living cell) has undergone significant advances. However, most approaches suffer from an inability to co-visualize multiple mRNA molecules simultaneously in space and in real-time. A further advance would enable spatiotemporally resolved studies to understand the orchestrated relationship between the mRNA species being expressed and functional effects of the expressed mRNA, and would allow the precise determination of the time points at which gene expression begins, the quantification of that expression and the development of quantitative models of gene expression, as well as determining the interaction and effect of multiple genes expressed on function.

Molecular beacons, nucleotide probes that fluoresce only upon hybridizing specifically to complementary mRNA sequences, present a general solution to the problem of visualizing gene expression (Tyagi, S. & Kramer, F. R. Molecular beacons: probes that fluoresce upon hybridization. Nat Biotechnol 14, 303-308 (1996)). In conjunction with fluorescent proteins and differing light microscopy and image analysis techniques they offer a possibility to be used in quantitative biology. However, improvements are still needed to enable relevant visualization and analysis of the signal delivered by these probes, especially when multiple gene expression and quantitative determination of hybridized probes is contemplated, as well as assessment of functional effects in vivo or in a living cell.

Several constraints exist to performing similar hybridization assays in living cells, chief among them, the ability of the probe to successfully pair with mRNA sequences which are found in complex secondary structures in vivo. In addition since the target nucleic acid is not immobilized or fixed prior to the introduction of the probe, dynamic interactions of mRNA with proteins and ribosomes are constantly occurring, meaning that many regions of the mRNA polymer are engaged in interactions with other cellular actors.

Previously, individual mRNA transcripts were tracked inside living cells using a construction that contained 96 beacon binding sites that were fused to a modified tetracycline response element in conjunction with a minimal CMV promoter (Vargas D. Y. et al, Mechanism of mRNA transport in the nucleus, PNAS vol. 102, no. 47, 17008-17013 (2005)). Such construction is not recognized by the transcriptional machinery inside eukaryotic cells to induce the reporter. Rather, this reporter system requires the presence of an engineered factor, the tetracycline-controlled transactivator, which consists of an engineered version of the bacterial Tet repressor molecule and repeats of a minimal VP16 transactivation domain. This reporter system is used to guaranty tightly regulated transcription depending on the amount of tetracycline added to the cells. Taken together, this reporter system does not allow the study of the expression of endogenous genes in eukaryotic cells from their natural promoter, and it requires the presence of (i) engineered factors to activate transcription, and of (ii) tetracycline as inducer of transcription.

Fluorescence resonance energy transfer (FRET) is one technique that has been used to assess gene expression. Fluorescence resonance energy transfer (FRET) is a form of molecular energy transfer (MET), a process by which energy is passed non-radioactively between a donor molecule and an acceptor molecule. FRET arises from the properties of certain chemical compounds; when excited by exposure to particular wavelengths of light, they emit light (i.e., they fluoresce) at a different wavelength. Such compounds are termed fluorophores. In FRET, energy is passed non-radioactively over a long distance (e.g., 10-100 Angstroms) between a donor molecule, which is a fluorophore, and an acceptor molecule, which is a quencher. The donor absorbs a photon and transfers this energy non-radioactively to the acceptor (Forster, 1949, Z. Naturforsch. A4: 321-327; Clegg, 1992, Methods Enzymol. 211: 353-388).

When two fluorophores whose excitation and emission spectra overlap are in close proximity, excitation of one fluorophore will cause it to emit light at wavelengths that are absorbed by and that stimulate the second fluorophore, causing it in turn to fluoresce. In other words, the excited-state energy of the first (donor) fluorophore is transferred by a resonance induced dipole-dipole interaction to the neighboring second (acceptor) fluorophore. As a result, the lifetime of the donor molecule is decreased and its fluorescence is quenched, while the fluorescence intensity of the acceptor molecule is enhanced and depolarized. When the excited-state energy of the donor is transferred to a non-fluorophore acceptor, the fluorescence of the donor is quenched without subsequent emission of fluorescence by the acceptor. In this case, the acceptor functions as a quencher.

Pairs of molecules that can engage in FRET are termed FRET pairs. In order for energy transfer to occur, the donor and acceptor molecules must typically be in close proximity (e.g., up to 70 to 100 Angstroms) (Clegg, 1992, Methods Enzymol. 211: 353-388; Selvin, 1995, Methods Enzymol. 246: 300-334). The efficiency of energy transfer falls off rapidly with the distance between the donor and acceptor molecules. Effectively, this means that FRET can most efficiently occur up to distances of about 70 Angstroms.

Thus, in FRET, a dye (called a "donor") transfers, after excitation by a light source, its energy to another dye (called "acceptor"). The energy transfer occurs when the emission spectrum of the donor dye overlaps significantly with the excitation spectrum of the acceptor. Sufficiently close juxtaposition of the two dyes, generally closer than 100 Ångstrom (Å), but preferably closer than 50 Ångstrom, is essential for energy transfer between the donor/acceptor pair. One Ångstrom, a metric unit of length, is equal to 0.1 nanometer or $10^{-10}$ meter. FRET is usually based on the interaction between donor and acceptor dyes that are both fluorescent. However, FRET can also be detected by the quenching of donor fluorescence using a non-fluorescent acceptor dye. Non-fluorescent acceptor dyes are in general advantageous because they eliminate the background fluorescence that results from direct acceptor excitation.

FRET energy transfer efficiency is inversely proportional to the sixth power of the distance between the donor and the acceptor. FRET, first described by Förster, has become extremely important for modern cell biology because FRET allows to measure distances between molecules on a scale of a few nanometers. This is far below the resolution limit of modern optical far field microscopy, which currently is at approximately 100 nm.

FRET technology has been used for detection of various individual (bio)molecules. FRET has been used to detect PCR amplification products in a method referred to the "molecular beacon probe" method described by Tyagi and Kramer (1996, Nature Biotech. 14:303-309) which is also the subject of U.S. Pat. Nos. 5,119,801 and 5,312,728 to Lizardi et al. This method employs oligonucleotide hybridization probes that can form hairpin structures. On one end of the hybridization probe (either the 5' or 3' end) there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus when the beacon is in the open conformation, the fluorescence of the donor fluorophore is detectable, whereas when the beacon is in the hairpin (closed) conformation, the fluorescence of the donor fluorophore is quenched. When employed in PCR, the molecular beacon probe, which hybridizes to one of the strands of the PCR product, is in the "open conformation," and fluorescence is detected, while those that remain unhybridized will not fluoresce (Tyagi and Kramer, 1996, Nature Biotechnol. 14: 303-306). As a result, the amount of fluorescence will increase as the amount of PCR product increases, and thus may be used as a measure of the progress of the PCR.

Additionally, U.S. Pat. No. 6,235,535 discloses a fluorescence-based immunoassay method for the detection of an analyte in a biological sample. The method is based on the ability of a multivalent analyte (antigen) to induce aggregation of identical receptor molecules (antibodies) labeled with a fluorophore, which molecules are immobilized onto yet freely mobile on a lipid membrane. Antigen-induced aggregation of the receptors causes FRET to take place. Also in U.S. patent Publication 2002/0081617, antibodies directed to the same epitope but labeled with either a donor of acceptor dye are immobilized, in this case onto beads. Upon addition of an analyte (antigen) of interest, the analyte functions as a bridge and brings a pair of antibodies into close proximity of each other which leads to FRET. Thus, U.S. Pat. No. 6,235,535 and U.S. patent Publication 2002/0081617 both relate to the detection or measurement of an analyte using immobilized, dye-conjugated probes and FRET-based detection methods. Since the probe sets of U.S. Pat. No. 6,235,535 and U.S. patent Publication 2002/0081617 are directed to a single molecule or molecular epitope, they are essentially not suitable for detecting distinct interacting molecules.

The extreme sensitivity of the FRET process on the distance between molecules renders it a very useful tool for the resolution of intracellular protein arrangements and protein dynamics. The presence of FRET indicates intermolecular interaction since it is observable only for nanometer-scale fluorophore distance. This implies in particular that simple co-localization of two molecules, e.g. proteins, is not sufficient to yield energy transfer. FRET is a technique that can give clear, unambiguous answers to questions about protein-protein interactions. FRET measurements can be used to determine protein interactions at the cell surface. The "green revolution" initiated by the introduction of the green fluorescent protein (GFP) from *Aequorea victoria* and the later developments of GFP-mutants possessing different spectral properties offered the possibility of simultaneous expression of different proteins, artificially tagged with fluorescent donor and acceptor domains in the same cell. This allowed measurement of their interactions by FRET. The combination of Cyano Fluorescent Protein (CFP) (donor) and Yellow Fluorescent Protein (YFP) (acceptor)—tagged proteins is often used. This FRET pair can be used to monitor the proximity of the two attached fluorescent tags in 3-6 nm. Co-expression of CFP- and YFP-tagged proteins has been successfully used to analyze short time changes in protein-protein interactions, e.g. oligomerization, co-localization, complex formation, activation of kinases and mapping of enzyme activities in living cells. FRET technology was also used in a highly specific fluorescence lifetime imaging microscopy (FLIM) method for monitoring epidermal growth factor receptor (EGFR) phosphorylation in cells. EGFR phosphorylation was monitored using a GFP-tagged EGFR and Cy3-conjugated anti-phosphotyrosine antibodies.

Although fluorescently tagged proteins have proven to be very useful, they do have limitations, such as their significant size (>200 amino acids). Also, the overall folding and tertiary structure of a tagged protein may be different from that of the native, non-tagged protein. This may result in different, erroneous interactions with other molecules. Another major drawback of the use of recombinant, tagged proteins lies in the fact that it requires transfection or co-transfection of a chimeric construct or constructs of interest into a cell and selection of a cell showing adequate expression of a construct to yield a functional protein. Such a system does not allow detection of an endogenous protein and can therefore not be used to evaluate endogenous interacting molecules.

FRET technology has also been applied for the detection of a protein-DNA interaction on the basis of a so-called indirect binding principle. For example, it was used to monitor the interaction between the p65 subunit of the transcription factor, NF-kappaB and its DNA binding site. NF-kappaB is of great relevance to the pharmaceutical sector due to its ability to regulate a number of genes involved in various immune and inflammatory responses, and as such, NF-kappaB has been implicated in several disease states including various viral infections (HIV), arthritis and cancer. An anti-GST antibody labeled with Cy3 (approx. 7-12 dyes per molecule) was allowed to interact with an affinity purified GST fusion protein of p65 and GST (p65GST). A double-stranded DNA (dsDNA) sequence which contains the NF-kappaB binding site was singly labeled with Cy5 at the 5' end of the coding sequence. This was then incubated with a Cy3 labeled antibody and p65GST. The reaction was done either in the presence or absence of unlabeled non-specific or specific competitor dsDNA. In the absence of either competitor, binding by p65-GST resulted in FRET between the Cy3 donor molecules on anti-GST and Cy5 acceptor molecule on dsDNA.

FRET technology has been reported to assess gene expression. US Patent Application 2009/0220961 reports a hairpin, double stranded self-quenching nucleic acid probe comprising both a fluorphore donor and acceptor molecule located in close proximity for use in real-time quantitative PCR methods where the amplification releases the fluorphore donor and emits fluorescence. Similarly, US Patent Application 2014/0295422 reports methods for real-time PCR using a dual labeled PCR primer. However, these systems are note suitable for gene expression analysis in living cells, and are also dependent on the precise placement of the distances of fluorphore donor and acceptor molecules on the probe/primers.

FRET technology has been reported to assess gene expression in living cells. For example, US Patent Application 2011/0021369 reports a similar stem-loop double stranded self-quenching oligonucleic acid probe as in 2009/0220961, where the hairpin probe comprises both a fluorphore donor and acceptor molecule located in close proximity, such that when the probe interacts with its target mRNA, the fluorphore donor and acceptor molecule are separated and FRET reaction is inhibited (i.e., the donor is no longer quenched by the acceptor molecule), providing a quantifiable signal (reduction in FRET) upon binding of the probe to the DNA. However, this system is dependent on a single probe and necessitates precise placement of the distances of fluorphore donor and acceptor molecules on the probe, and can lead to unwanted noise, or poor signal-to-noise, or relative insensitivity if the placement of these FRET molecules are incorrect.

Additionally, US Patent Application 2003/0096243 reports a method of mRNA quantification in living cells by attaching to a mRNA of interest a tag comprising a binding site for a RNA binding protein, allowing a fluorophore labeled RNA binding protein to bind to the tagged mRNA. Unlike the present invention, the method disclosed in 2003/0096243 requires the mRNA of the target gene to comprise a "RNA-tag" which is inserted by homologous recombination, viral infection or other recombinant DNA techniques, resulting in a synthetic tag inserted into the mRNA (located cis- (upsteam or downstream)) to the target mRNA, which could compromise mRNA translation and/or function.

Because most of these and other known methods using FRET use dual-labeled probes or technically demanding methods for precisely controlled fluorphore and acceptor placement, they are not universal for all gene expression systems. It would be advantageous to possess a method that allows the detection of multiple gene expression in living cells that is universal to any gene of interest to be studied, allowing for quick, simple and efficient analysis of expression of multiple genes simultaneously in living cells. Therefore, in view of the state of the art, a need exists for broadly applicable in vivo assays for analysis of multiple gene expression in single cells. The improvements needed involve primer design flexibility, and a universal system that is applicable to multiple cell types and organisms.

All publications and patent applications mentioned in this specification are herein incorporated by reference to the same extent as if each individual publication or patent application was specifically and individually indicated to be incorporated by reference.

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions

SUMMARY OF THE INVENTION

The present invention is directed methods, compositions and kits related to in vivo gene expression of multiple genes in single living cells. More particularly, the present invention relates to a method of Multiplex Analysis of Gene expression in Individual living Cells (also referred to herein as "MAGIC"), where a living cell is provided with (i) one or more RNA binding probes which are labeled with a FRET dye, where the RNA binding probes are specific (e.g., can specifically hybridize) to the mRNA of gene(s) of interest, and (ii) a polypeptide comprising a FRET dye that is spectrally paired with the FRET dye on the RNA binding probe, such that when the RNA binding probe hybridizes with the mRNA of gene of interest, it forms a duplex (e.g., a RNA binding probe-mRNA duplex or RBP:mRNA duplex) which is recognized and allows binding of the polypeptide, bringing the two FRET dyes into close proximity and allowing fluorescence resonance energy transfer (FRET) and a detectable change in fluorescence.

In all aspects, a RNA binding probe useful in the methods, compositions and kits as disclosed herein, is any nucleic acid that specifically hybridizes to the target mRNA. In some embodiments, the RNA binding probe is a nucleic acid substantially complementary to a portion of the target mRNA. In some embodiments, a RNA binding probe is a RNA, a RNA analogue or modified RNA, therefore forming a dsRNA duplex with the target mRNA. This dsRNA duplex is recognized and allows for binding of a polypeptide comprising a double stranded RNA binding domain (dsRBD). Other RNA binding probes are encompassed in the methods, compositions and kits as disclosed herein, for example, DNA, DNA analogues, LNA and the like, therefore allowing the formation of heteroduplexes between the RNA binding probe and the target mRNA, which are recognized by specific FRET dye labeled polypeptides.

In all aspects, a polypeptide useful in the methods, compositions and kits as disclosed herein is any polypeptide or peptide that binds to the duplex formed between the RNA binding probe and the target mRNA (RBP:mRNA duplex). In some embodiments, where the RBP:mRNA duplex is a double stranded RNA, the polypeptide comprises a double stranded RNA binding domain (dsRBD).

In an exemplary aspect, the methods, compositions and kits as disclosed herein relates to a method for multiple gene expression in individual living cells, where inside the cell is a RNA binding probe (RBP) that comprises RNA labeled with a second dye, and a polypeptide comprising a dsRBD labeled with a first dye, where the first and second dyes are spectrally paired such that when the dsRBD binds to a dsRNA duplex formed between the RNA binding probe and a portion of the mRNA of the target gene, the first and second dyes come into close proximity and are juxtapositioned together, allowing FRET to occur and a detectable change in emitted fluorescence. The detectable change in fluorescence can be monitored or imaged using fluorescence microscopy, including confocal fluorescence microscopy, live imaging fluorescence microscopy, FACs or other methods as disclosed herein.

Additionally, in some embodiments, the methods, compositions and kits as disclosed herein can be used to monitor the expression of multiple genes in a single living cell, for example, where a plurality of RNA binding probes are introduced into the cell, each RNA binding probe specifically hybridizing to a region of the mRNA of a different target gene of interest, and where each RNA binding probe is labeled with a different dye, such that when different RNA-binding probe-mRNA duplexes are formed, they are recognized by one or more polypeptides (i.e., duplex binding polypeptides) each comprising FRET dyes that are spectrally paired to each of the dyes of each of the RNA binding probes, such that the FRET reactions identify which of the RNA-binding probes are bound to the target mRNA, enabling simultaneous detection and monitoring of multiple genes expressed in a living cell in real time. In some embodiments, the methods, compositions and kits as disclosed herein can be used to monitor the expression of at least 2, or at least 3, or at least 4, or between 4-6, or between 7-10, or between 10-15, or between 16-20 or more than 20 genes at the same time.

Accordingly, one aspect of the present invention relates to a method for detection of the expression of one or more genes of interest in a living cell, comprising the steps of: a) providing a cell with (i) at least one RNA binding probe (RBP) which specifically hybridizes to a target RNA, e.g., a mRNA expressed by a gene of interest, or a non-coding RNA in the cell, whereby the RNA-binding probe and target RNA form a duplex (also referred to herein as a "RBP-RNA duplex" or "RBP-mRNA duplex"), and (ii) a duplex-binding polypeptide which binds to a RBP-RNA duplex, where the duplex binding polypeptide (also referred to herein as a "DBP") is labeled with, or fused to at least a first dye, where at least one RNA binding probe is labeled with at least a second dye, and where the first and second dyes are spectrally paired such that when juxtapositioned together, allows fluorescence resonance energy transfer (FRET) and detectable change of fluorescence, (b) allowing the RNA binding probe to hybridize to the target RNA (e.g. mRNA or non-coding RNA) to form the RBP-RNA duplex, and (c) measuring fluorescence of the cell and detecting a change in fluorescence when the duplex-binding protein (DBP) binds to the RBP-RNA duplex, thereby detecting gene expression of the RNA of interest (e.g., a mRNA of a gene of interst, or a non-coding RNA) in the living cell.

In some embodiments, the RNA binding probe for use in the methods, compositions and kits as disclosed herein comprises a nucleic acid sequence that is substantially complementary to the target RNA or target mRNA of the gene of interest. In some embodiments, the RNA binding probe is nucleic acid or nucleic acid analogue, for example, it can be selected from any of: RNA, modified RNA, DNA, ssDNA or a modified nucleic acid. In some embodiments, the RBP-RNA duplex is a homoduplex, e.g., a dsRNA duplex, and in alternative embodiments, the RBP-RNA duplex is a heteroduplex comprising a target RNA (e.g., mRNA or non-coding RNA) and RBP which is ssDNA or LNA or nucleic acid analogue. In some embodiment, a RNA binding probe is a RNA or modified RNA, and the duplex is a double stranded RNA (dsRNA) duplex.

In some embodiments, a duplex-binding polypeptide for use in the methods, compositions and kits as disclosed herein comprises a double stranded RNA binding domain (dsRBD). In some embodiments, a duplex-binding polypeptide for use in the methods, compositions and kits as disclosed herein comprises a dsRBD from the ADAR family or the Staufen family, or any dsRBD listed in Table 1. In some embodiments, a duplex-binding polypeptide for use in the methods, compositions and kits as disclosed herein comprises a dsRBD selected from any of the following double stranded RNA binding proteins (dsRBP): protein kinase R (PKR), ADAD2, ADAR1, ADAR2, TRBP2, Stau1, Dicer, X1RBPA, DGCR8, NFAR1, NFAR2, SPNR, RHA, NREBP/SON, TENR, RDE1, Kanadaptin, HYL1 or RNaseIII.

In some embodiments, a duplex-binding polypeptide for use in the methods compositions and kits as disclosed herein comprises a dsRBD from protein kinase R (PKR) or a homologue thereof, for example, the a duplex-binding polypeptide comprises a dsRBD comprising SEQ ID NO: 1 or a protein that has at least 80% amino acid sequence identity to SEQ ID NO: 1. In some embodiments, a dsRBD comprises SEQ ID NO: 2 or a protein that has at least 80% amino acid sequence identity to SEQ ID NO: 2. In some embodiments, a dsRBD comprises an amino acid of the consensus sequence of SEQ ID NO: 28.

In all aspects of the technology described herein, the methods, compositions and kits as disclosed herein can comprise at least 2 RNA binding probes, wherein each RNA binding probe hybridizes to (or is substantially complementary to), a different target RNA (e.g., mRNA expressed by a gene of interest or non-coding RNA) in the cell, and wherein each RNA binding probe comprises a different second dye. In some embodiments, the methods, compositions and kits as disclosed herein can comprise at least 3-5, or about 6-10, or more than 10, but less than 50 different RNA binding probes, wherein each RNA binding probe hybridizes to a different target RNA (e.g., mRNA expressed by a gene of interest, or non-coding RNA) in the cell, and wherein each RNA binding probe comprises a different second dye.

Another aspects of the technology described herein, release to a set of probes comprising; (i) a duplex-binding polypeptide as described herein, e.g., a polypeptide comprising a double stranded RNA binding domain (dsRBD) labeled with, or fused to, at least a first dye, and (ii) at least one RNA binding probe which hybridizes to a target RNA (e.g., a mRNA expressed by a gene of interest or a non-coding RNA) in a cell to form a RBP-RNA duplex, wherein the at least one RNA binding probe is labeled with a second dye, and where the first and second dyes are spectrally paired as discussed herein, such that when the first and second dye are juxtapositioned together, fluorescence resonance energy transfer (FRET) occurs and detectable change of fluorescence occurs, which can be measured by conventional fluorescence detection techniques.

In some embodiments, the set of probes comprises a duplex-binding polypeptide which comprises a dsRBD from the ADAR family or the Staufen family, or any dsRBD listed in Table 1. In some embodiments, a duplex-binding polypeptide for use in the methods, compositions and kits as disclosed herein comproses a dsRBD selected from any of the following double stranded RNA binding proteins (dsRBP): protein kinase R (PKR), ADAD2, ADAR1, ADAR2, TRBP2, Stau1, Dicer, X1RBPA, DGCR8, NFAR1, NFAR2, SPNR, RHA, NREBP/SON, TENR, RDE1, Kanadaptin, HYL1 or RNaseIII.

In some embodiments, set of probes comprises a duplex-binding polypeptide which comprises a dsRBD from protein kinase R (PKR) or a homologue thereof, for example, the a duplex-binding polypeptide comprises a dsRBD comprising SEQ ID NO: 1 or a protein that has at least 80% amino acid sequence identity to SEQ ID NO: 1. In some embodiments, a dsRBD comprises SEQ ID NO: 2 or a protein that has at least 80% amino acid sequence identity to SEQ ID NO: 2. In some embodiments, a dsRBD comprises an amino acid of the consensus sequence of SEQ ID NO: 28.

In all aspects of the technology described herein, the first dye is a donor dye (also referred to herein as a as "flurophore donor") and the second dye is an acceptor dye (also known as a "quencher" or "dark quencher"). In alternative embodiments, the first dye is an acceptor dye and the second dye is a donor dye. It does not necessarily matter if the RBP comprises the acceptor dye or the donor dye, so long as the dyes on the RBP and the duplex-binding protein are spectrally paired and that a FRET reaction occurs when the duplex-binding protein binds to the RBP-RNA duplex. In some embodiments, the duplex-binding protein comprises the donor dye (or fluorophore donor) and the RBP comprises the acceptor dye (or acceptor fluorophore).

Another aspect of the present invention relates to a duplex-binding polypeptide comprising a double stranded RNA binding domain (dsRBD) labeled with, or fused to a fluorophore donor. In some embodiments, the polypeptide is a fusion protein comprising a dsRBD fused to a fluorophore donor, wherein the flurophore donor is located at the N-terminal, or C-terminal or both of the dsRBP. As disclosed herein, the a duplex-binding polypeptide can comprise a dsRBD from the ADAR family or the Staufen family, or any dsRBD listed in Table 1. In some embodiments, a duplex-binding polypeptide can comprise a dsRBD selected from any of the following double stranded RNA binding proteins (dsRBP): protein kinase R (PKR), ADAD2, ADAR1, ADAR2, TRBP2, Stau1, Dicer, X1RBPA, DGCR8, NFAR1, NFAR2, SPNR, RHA, NREBP/SON, TENR, RDE1, Kanadaptin, HYL1 or RNaseIII. In some embodiments, a duplex-binding polypeptide which comprises a dsRBD from protein kinase R (PKR) or a homologue thereof, comprises SEQ ID NO: 1 or a protein that has at least 80% amino acid sequence identity to SEQ ID NO: 1. In some embodiments, a duplex-binding polypeptide comprises an amino acid sequence of SEQ ID NO: 2 or a protein that has at least 80% amino acid sequence identity to SEQ ID NO: 2. In some embodiments, a duplex-binding polypeptide comprises an amino acid of the consensus sequence of SEQ ID NO: 28.

In all aspects of the technology described herein, a donor dye is a fluorescent donor dye, also referred to herein as "flurophore donor" and the acceptor dye is a fluorescent acceptor dye (also known herein as "flurophore acceptor", "quencher" or "dark quencher".

In all aspects of the technology described herein, a the fluorophore donor can be selected from any fluorescent protein or small fluorescent dye molecule, such as a:
(i) fluorescent proteins are selected from the group consisting of
  a. blue fluorescent proteins, preferably selected from the group consisting of EBFP, EBFP2, Azurite and imTagBFP,
  b. cyan fluorescent proteins, preferably selected from the group consisting of ECFP, mECFP, Cerulean, mTurquoise, CyPet, AmCyan1, Midori-lshi Cyan, TagCFP and mTFP1 (Teal),
  c. yellow fluorescent proteins, preferably selected from the group consisting of EYFP, Topaz, Venus, mCitrine, YPet, TagYFP, PhiYFP, ZsYellow1 and mBanana,
  d. orange fluorescent proteins, preferably selected from the group consisting of Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer and mTangerine,
  e. red fluorescent proteins, preferably selected from the group consisting of mRuby, mApple, mStrawberry, AsRed2, mRFP1, JRed, mCherry, HcRed1, mRaspberry, dKeima-Tandem, HcRed-Tandem, mPlum and AQ143,
  f. green fluorescent proteins (GFP), selected from the group consisting of EGFP, Emerald, Superfolder GFP, Azami Green, mWasabi, TagGFP, TurboGFP, AcGFP, ZsGreen and T-Sapphire,
(ii) small fluorescent dye molecules selected from the group consisting of
  a. acridines, selected from: acridine orange or acridine yellow,
  b. cyanines, selected from: Cy2, Cy3, Cy3B, Cy3.5, Cy5, Cy5.5, Cy7,
  c. fluorones, selected from: Fluorescein, Carboxyfluorescein, Dichlorofluorescein, Eosin, Eosin B, Eosin Y or Erythrosine,
  d. oxazines, selected from: Cresyl violet, Nile blue or Nile red,
  e. phenanthridines, selected from: Ethidium bromide, Gelred or Propidium iodide, and
  f. rhodamines, selected from: Rhodamine, Rhodamine 123, Rhodamine 6G, Rhodamine B, Auramine, Sulforhodamine 101, Sulforhodamine B or Texas red, In all aspects of the technology described herein, a fluorophore acceptor for use in the methods, compositions and kits can be selected from any of the following:
(i) acridines, selected from acridine orange or acridine yellow,
(ii) cyanines, selected from Cy2, Cy3, Cy3B, Cy3.5, Cy5, Cy5.5 or Cy7,
(iii) fluorones, selected from Fluorescein, Carboxyfluorescein, Dichlorofluorescein, Eosin, Eosin B, Eosin Y or Erythrosine,
(iv) oxazines, preferably Cresyl violet, Nile blue or Nile red,
(v) phenanthridines, preferably ethidium bromide, Gelred or propidium iodide, and
(vi) rhodamines, preferably Rhodamine, Rhodamine 123, Rhodamine 6G,
(vii) Rhodamine B, Auramine, Sulforhodamine 101, Sulforhodamine B or Texas red, preferably cyanines (ii), more preferably Cy3.

In all aspects of the technology described herein, a dark quencher for use in the methods, compositions and kits can be selected from the group consisting of Dabcyl, Dabsyl, Black Hole Quencher (BHQ™) dyes, preferably BHQ-0, BHQ-1, BHQ-2 or BHQ-3, QXL quenchers, preferably QXL 490, QXL 570, QXL 610, QXL 670, or QXL 680, Iowa Black quenchers, preferably Iowa black FQ or Iowa Black RQ, and IRDyes, preferably IRDye 800, IRDye 800CW, IRDye 800RS, IRDye 680, IRDye 680LT, IRDye 700, or IRDye 700DX, more preferably Black Hole Quencher (BHQ™) dyes, most preferably BHQ-1.

In all aspects of the technology described herein, a spectrally paired fluorophore donor and fluorophore acceptor, or the spectrally paired fluorophore donor and dark quencher for use in the methods, compositions and kits can be selected from the group consisting of:
1. protein-protein pairs, selected from the group consisting of ECFP-Citrine, ECFP-Venus, Cerulean-Citrine, Cerulean-Venus, Cerulean-Ypet, Cerulean-YFP, CyPet-EYFP, CyPet-Venus, CyPet-YPet, CyPet-Citrine, mTurquoise-Venus, mTurquoise-Ypet, mTurquoise-Citrine, ECFP-EYFP, TagGFP-TagRFP, mTFP1-Citrine, Citrine-mKate2, mTurquoise1-SEYFP, mTurquoise2-SEYFP and clover-mRuby2,
2. protein-organic dye pairs, selected from the group consisting of EGFP-mCherry, SYFP2-mStrawberry, mTFP1-mOrange, Clover-mCherry, GFP-Cy3, YFP-Cy3, ECFP-BHQ-0, EYFP-BHQ-2, EGFP-Cy3 and EGFP-BHQ-1,
3. organic dye-organic-dye pairs, selected from the group consisting of mOrange-mCherry, Alexa488-Alexa555, Alexa488-Cy3, Alexa 568-Alexa633, Cy3-Cy5, Alexa 488-Alexa514, Alexa488-Alexa532, Alexa488-546, Alexa488-610, Alexa647-Alexa 680, Alexa647-Alexa680, Alexa647-Aelxa700, Alexa647-Alexa750, BHQ-1-FAM, BHQ-1-TET, BHQ-1-JOE, BHQ-1-HEX, BHQ-1-Oregon green, BHQ-2-TAMRA, BHQ-2-ROX, BHQ-2-Cy3, BHQ-2-Cy3.5, BHQ-2-CAL Red, BHQ-2-Red 640, BHQ-3-Cy5, or BHQ-3-Cy5.5, Dabcyl-Edans and Dabsyl-Edans, fluorescine.

Another aspect of the technology described herein relates to a nucleic acid sequence encoding a duplex-binding polypeptide as described herein. In some embodiments, the nucleic acid sequence encodes a polypeotide of SEQ ID NO: 1 or a polypeptide of at least 80% sequence identity thereof. In some embodiments, the nucleic acid sequence comprises a portion of SEQ ID NO: 75, where the portion of SEQ ID NO: 75 encodes the protein of SEQ ID NO: 1. In some embodiments, the nucleic acid sequence can encode a fusion protein comprising a polypeptide of SEQ ID NO: 8 fused to a donor fluorphore as disclosed herein, and optionally can also encode a nucleic acid sequence encoding a tag (e.g., His-tag) for purifition of the duplex-binding protein using standard purification methods commonly known in the art.

Another aspect of the technology described herein relates to a vector comprising a nucleic acid sequence encoding a duplex-binding polypeptide as described herein, e.g., encoding a polypeotide of SEQ ID NO: 1 or a polypeptide of at least 80% sequence identity thereof. Any vector can be used, typically the vector is an expression vector. Another aspect of the technology described herein relates to a cell or cell line comprising a vector comprising a nucleic acid sequence encoding a duplex-binding polypeptide as described herein, e.g., encoding a polypeotide of SEQ ID NO: 1 or a polypeptide of at least 80% sequence identity thereof.

Another aspect of the technology described herein relates to a living cell or cell line comprising at least one duplex-binding protein labeled with a first dye as described herein, and at least one, or at least 2, or at least three RNA-binding probes labeled with a second dye as disclosed herein, where the first and second dyes are spectrally paired such that when they are juxtapositioned together, a fluorescence resonance energy transfer (FRET) reaction occurs and a detectable change of fluorescence occurs. The living cell or cell line can be measured for a detectable change in fluorescence when one or more of the duplex-binding protein (DBP) bind to their target RNAs (e.g., mRNA or non-coding RNA) such that each RBP-RNA duplex is bound by a duplex-binding protein and a different FRET reaction occurs, allowing detection of expression of each RNA target of each of the RNA-binding proteins in the living cell.

Another aspect of the technology described herein relates to a kit comprising: (i) duplex-binding protein as disclosed herein, e.g., a double stranded RNA binding domain (dsRBD) labeled with, or fused to, at least a first dye and/or a vector comprising a nucleic acid for encoding the same; (ii) at least one second dye; and (iii) reagents for attaching the second dye to a RNA probe.

In some embodiments, the kit comprises one or more of: a T7 phage polymerase, dATP, dCTP, dGTP, aminoallyl-modified UTP, where a fluorphore (e.g., a fluorophore acceptor or second dye) can be added to UTP by amino-coupling to aminoallyl-modified uridine bases. In some embodiments, the kit also includes one or more flurophores, e.g., flurophore acceptors to be added to the RBP by amino-coupling to aminoallyl-modified uridine bases. In some embodiments, the kit also comprises reaction buffers and regents such that the kit user can in vitro transcribe RBPs that specifically hydride to their preferred target RNA, e.g., mRNA or other RNA type (e.g., small non-coding RNA). In some embodiments, the kit comprises a Alexa Fluor 647 which can be added to the amino groups on the uridine bases. The kit can comprise a number of different fluorphores, e.g., fluorphore accecpetors as described herein to allow the kit user to generate a range of dye-labeled RBP for multiplex gene expression analysis in single cells according to the methods disclosed herein. In some embodiment, the kit allows the addition of 1, 2 or 3 fluorophore molecules to be added to a single RNA-binding probe.

Accordingly, in some embodiments, the kit can comprise include reagents employed in the various methods, such as primers for generating and in vitro transcription of target RNA-binding probes, dNTPs and/or rNTPs, which may be either premixed or separate, one or more uniquely labeled dNTPs and/or rNTPs, such as fluorophore-labeled or tagged dNTPs, with different scattering spectra, or other post synthesis labeling reagent, and various buffer mediums, e.g. hybridization and washing buffers.

In some embodiments, the kit can optionally comprose a vector encoding a nucleic acid sequence encoding a duplex-binding protein as disclosed herein, e.g., a dsRBD as disclosed herein in Table 1 or comprising the amino acid sequence of SEQ ID NO: 1 or a protein of at least 80% sequence identity to SEQ ID NO: 1.

In some embodiments, the kit comprises a duplex-binding protein as disclosed herein, e.g., a dsRBD labeled with, or fused to, at least a first dye, the first dye is a donor dye, e.g., flurophore donor as disclosed herein. In some embodiments, the kit any fluorophore acceptor or dark quencher as disclosed herein, where the fluorophore acceptor or dark quencher can be added into a RNA-binding probe via in vitro transcription by being added to the amino groups on the modified uridine bases.

There are several advantages to the muliplex gene expression system in living cells in accordance with the present invention. These advantages include:

Cost effectiveness: The Multiplex Analysis of Gene expression system in Individual living Cells as disclosed herein utilizes a specific duplex binding protein attached to a dye and one or more RNA binding probes with a spectrally paired dye. Synthesis is simpler and more cost-effective than those gene expression systems requiring two or more dyes (donor and receptor) on the same molecule.

Simple RNA binding probe design: the RNA binding probe only comprises the sequence complementary to the mRNA target molecule and a dye, and need not comprise additional sequences or complex tertiary structures (e.g., hairpin folding). In comparison, other multiplex gene expression systems with probes comprising with two or more dyes require a proper positioning of dyes with respect to one another in order to accomplish the energy transfer, which usually can only be achieved by trial and error, making it a very time-consuming and costly step.

Less complexity for multiplex gene expression analysis: Almost all primer and probe-based technologies have inherent complexities related to the kinetics of the hybridization and detection, and often require a set of two gene specific primers as well as a gene specific probe. In the MAGIC system as disclosed herein, each target mRNA needs only two one RNA binding probe, making it less complex for multiplex gene expression.

Living cells: As the MAGIC system as disclosed herein can be used in living cells, it allows the functional effect of the expression of specific genes to be analyzed. Additionally, if the RNA binding probe is a inhibitory RNA (RNAi) molecule, it allows the functional effect of a knock-down or inhibition of an expressed gene to be assessed in real time in a living cell. Most multiplex gene expression systems are not applicable to living cells, nor can they be used to assess the functional effect of expression or inhibition of expression of multiple target genes at a single time.

Lower background: The fluorescence will be perfectly quenched in a living cell after a RNA binding probe binds to the target mRNA sequence and is recognized and bound by the duplex binding protein. As multiple RNA binding probe can be used simultaneously which are specific to different mRNA molecules, the expression of multiple genes can be assessed in real-time in a living cell. This system gives low background of fluorescence, making detection of specific gene expression products (e.g., mRNA) potentially more sensitive and specific.

BRIEF DESCRIPTION OF THE DRAWINGS

This patent or applicationn file contains at least one drawing executed in color. Copies of this patent or patent application publication with color drawing(s) will be provided by the Office upon request and payment of the necessary fee.

FIG. 1A shows an exemplary MAGIC factor that is the double-stranded (dsRNA)-binding domain (dsRBD) of human protein kinase R (PKR). Subsequent to multiple molecular cloning steps, the protein was expressed it in bacteria and purified via cobalt immobilized metal chelate affinity beads. The dsRBD was fluorescently labeled it via chemically attaching Alexa Fluor 488 to its primary amino groups. A fully functional purified probe was obtained via affinity purification using dsRNA-coupled agarose beads. FIG. 1B shows exemplary MAGIC RNA-binding probes consist of 20-mer RNA generated through standard in vitro transcription using T7 phage polymerase. In order to enable fluorescent labeling, the uridine bases were replaced with aminoallyl-modified uridine bases during in vitro transcription. This allowed the chemical attachment of Alexa Fluor 546, 594 and 647 to the amino-modified uridine base. The final MAGIC RNA-binding probes were obtained via purification of one- and two-labeled probes from a denaturing polyacrylamide gel.

FIG. 3A shows electrophoretic Mobility Shift Assay (EMSA) of fluorescent dsRNA and ssRNA with fluorescent MAGIC factor. Unlabeled and unpurified fluorescent MAGIC factor and affinity purified fluorescent MAGIC factor were reacted with Alexa Fluor 647-labeled dsRNA and ssRNA and run on a native gel. The gel was visualized in the RNA channel (Ex. 633 nm/Em. 670/30 nm BP), protein channel (Ex. 488 nm/Em. 526 nm SP) and FRET channel (Ex. 488 nm/Em. 670/30 nm). FIG. 3B shows representative EMSA and the corresponding binding curves of unpurified and affinity purified fluorescent MAGIC factor with $K_d$ and Hill coefficients. The dashed lines represent the cutoff after which increasing concentrations of only unpurified MAGIC factor were reacted with dsRNA.

FIG. 4A shows in vitro transcribed and fluorescently-labeled a 20-mer RNA-binding probe with Alexa Fluor 647, where one-, two-, three- and four-labeled RNA-binding probes were purified from a denaturing polyacrylamide gel. FIG. 4B shows the fluorescent intensity of the four RNA probes as measured with a spectrophotometer. Data is shown as mean±s.e.m. p<0.01 and *p<0.001.

FIG. 5A shows that in vitro transcribed and fluorescently-labeled a 20-mer RNA-binding probes with Alexa Fluor 647, where one-, two-, three- and four-labeled RNA-binding probes are purified from a denaturing polyacrylamide gel. FIG. 5B shows fluorescent intensity of the four RNA probes as measured with a spectrophotometer. Data is shown as mean±s.e.m. p<0.01 and *p<0.001.

FIG. 6A shows an Electrophoretic Mobility Shift Assay (EMSA) of fluorescent dsRNA with various degrees of fluorescent labeling with a fluorescent dsRBD MAGIC factor. The gel was visualized in the RNA channel (Ex. 633 nm/Em. 670/30 nm BP), protein channel (Ex. 488 nm/Em. 526 nm SP) and FRET channel (Ex. 488 nm/Em. 670/30 nm). FIG. 6B shows a quantitative assessment of the EMSA with respect to the relative shift of the dsRNA, the corrected FRET (cFRET) intensity of shifted dsRNA and the cFRET/shift ratio.

FIG. 7A-7G shows Multiplex Analysis of Gene Expression in Individual Living Cells (MAGIC). FIG. 7A shows that, upon delivery into living cells via transfection, MAGIC RNA-binding probes hybridize to their target gene and generate a RNA-RNA hybrid. This enables dsRBD MAGIC factor to bind and FRET to occur (blue arrow: excitation of the donor; orange arrow: energy transfer; red arrow: emission of the acceptor). FIG. 7B shows single living NKX2-5 eGFP$^+$ CMs were first analyzed for MHCα gene expression using MAGIC and then analyzed for MHCα protein expression by immunofluorescence (IF). FIG. 7C shows a contingency table of analyzed CMs (n=38). FIG. 7D shows single living NKX2-5 eGFP$^+$ CMs were analyzed for their MHCα gene expression first and then loaded with Fluo-4 AM to analyze their spontaneous Ca$^{2+}$ handling properties. Representative Ca$^{2+}$ transient of MHCα$^+$ and MHCα$^-$ CMs is shown. FIG. 7E shows the quantification of Ca$^{2+}$ kinetics of MHCα$^+$ and MHCα$^-$ CMs with time to reach peak amplitude, time to decay to baseline and decay velocity (n=28). FIG. 7F shows single living NKX2-5 eGFP$^+$ CMs were analyzed for their MHCα gene expression first and then loaded with Fluo-4 AM to analyze their Ca$^{2+}$ handling properties in response to caffeine. Representative Ca$^{2+}$ transient of MHCα$^+$ and MHCα$^-$ CMs before and after caffeine administration is shown. FIG. 7G shows a caffeine-induced change of peak fluorescence intensity (n=20). Scale bar 10 µm. Data is shown as mean±s.e.m. p<0.01 and *p<0.001.

FIG. 8A shows a single living NKX2-5 eGFP$^+$ CMs were first analyzed for MLC2v gene expression using MAGIC and subsequently analyzed for MLC2v protein expression by immunofluorescence (IF). The cells were imaged using indicated filter sets. FIG. 8B shows a contingency table of analyzed CMs (n=45). Scale bar 10 µm.

FIG. 9A shows hESC-CMs were either not transfected, exposed to the transfection reagents only or delivered with unlabeled MAGIC factor and unlabeled MAGIC probe against the human β-actin mRNA. The viability of over 1,200 living cells in each group was assessed when cells would be imaged (6 h) or after an additional 18 h (24 h) of cell culture using a two-color fluorescence assay (n=3). The transfection protocol was associated with no increase in cell death (green cells are living, red cells are dead). FIG. 9B shows representative images of (A). Scale bar 100 µm. Data is shown as mean±s.e.m. NS, not significant.

FIG. 10A shows transcript levels of the (β-actin gene were assessed when cells would be imaged (6 h) or after an additional 18 h (24 h) of cell culture via quantitative PCR and normalized after the ratio to the housekeeping gene GAPDH was calculated (n=3). FIG. 10B shows a representative immunoblots of (β-actin and the housekeeping protein α-tubulin of corresponding controls and experimental group. Data is shown as mean±s.e.m. NS, not significant.

FIG. 11A shows spectral imaging using laser scanning confocal microscope and imaging in the spectral range 500-740 nm using 488 nm, 561 nm and 639 nm lasers. Images showing 30 nm spectral windows excited by each laser of the same region of interest are shown. FIG. 11B shows linear unmixing and independent component analysis resulted in the acquisition of seven distinct fluorescence images, showing each type of construct individually. The merge image was color-coded.

FIG. 12 shows that the technology described herein can be used to discern at least three different FRET pairs, demonstrating its multiplex potential.

(FIG. 13 is reproduced from Masliah et al., RNA recognition by double-stranded RNA binding domains: a matter of shape and sequence., Cell Mol Life Sci. 2013; 70(11): 1875-1895).

DETAILED DESCRIPTION OF THE INVENTION

Figures 1A, 1B:
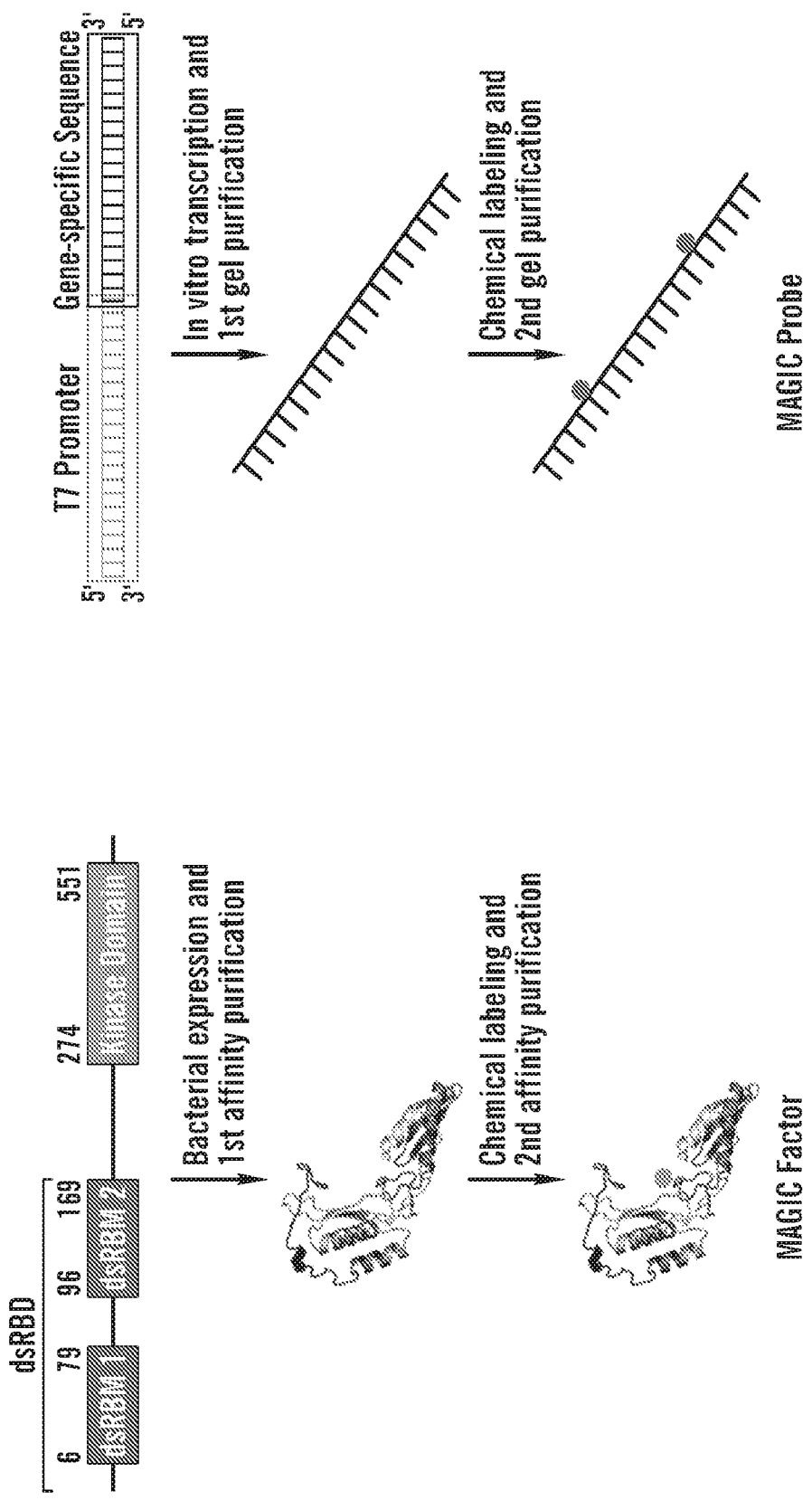
FIG. 1A-1B are schematic drawings showing a strategy for the Engineering of MAGIC Factor and MAGIC Probes.

The present invention is directed methods, compositions and kits related to in vivo gene expression of multiple genes in single living cells. More particularly, the present invention relates to a method of Multiplex Analysis of Gene expression in Individual living Cells (also referred to herein as "MAGIC"), where a living cell is provided with (i) one or more RNA binding probes which are labeled with a FRET dye, where the RNA binding probes are specific (e.g., can specifically hybridize) to the mRNA of gene(s) of interest, and (ii) a polypeptide comprising a FRET dye that is spectrally paired with the FRET dye on the RNA binding probe, such that when the RNA binding probe hybridizes with the mRNA of gene of interest, it forms a duplex (e.g., a RNA binding probe-mRNA duplex or RBP:mRNA duplex) which is recognized and allows binding of the polypeptide, bringing the two FRET dyes into close proximity and allowing fluorescence resonance energy transfer (FRET) and a detectable change in fluorescence.

In all aspects, a RNA binding probe useful in the methods, compositions and kits as disclosed herein, is any nucleic acid that specifically hybridizes to the target mRNA. In some embodiments, the RNA binding probe is a nucleic acid substantially complementary to a portion of the target mRNA. In some embodiments, a RNA binding probe is a RNA, a RNA analogue or modified RNA, therefore forming a dsRNA duplex with the target mRNA. This dsRNA duplex is recognized and allows for binding of a polypeptide comprising a double stranded RNA binding domain (dsRBD). Other RNA binding probes are encompassed in the methods, compositions and kits as disclosed herein, for example, DNA, DNA analogues, LNA and the like, therefore allowing the formation of heteroduplexes between the RNA binding probe and the target mRNA, which are recognized by specific FRET dye labeled polypeptides.

In all aspects, a polypeptide useful in the methods, compositions and kits as disclosed herein is referred to a "duplex-binding protein" and is any polypeptide or peptide that binds to the duplex formed between the RNA binding probe and the target mRNA (RBP:mRNA duplex). In some embodiments, where the RBP:mRNA duplex is a double stranded RNA, the polypeptide comprises a double stranded RNA binding domain (dsRBD).

In an exemplary aspect, the methods, compositions and kits as disclosed herein relates to a method for multiple gene expression in individual living cells, where inside the cell is a RNA binding probe (RBP) that comprises RNA labeled with a second dye, and a polypeptide comprising a dsRBD labeled with a first dye, where the first and second dyes are spectrally paired such that when the dsRBD binds to a dsRNA duplex formed between the RNA binding probe and a portion of the mRNA of the target gene, the first and second dyes come into close proximity and are juxtapositioned together, allowing FRET to occur and a detectable change in emitted fluorescence. The detectable change in fluorescence can be monitored or imaged using fluorescence microscopy, including confocal fluorescence microscopy, live imaging fluorescence microscopy, FACs or other methods as disclosed herein.

Additionally, in some embodiments, the methods, compositions and kits as disclosed herein can be used to monitor the expression of multiple genes in a single living cell, for example, where a plurality of RNA binding probes are introduced into the cell, each RNA binding probe specifically hybridizing to a region of the mRNA of a different target gene of interest, and where each RNA binding probe is labeled with a different dye, such that when different RNA-binding probe-mRNA duplexes are formed, they are recognized by one or more polypeptides (i.e., duplex binding polypeptides) each comprising FRET dyes that are spectrally paired to each of the dyes of each of the RNA binding probes, such that the FRET reactions identify which of the RNA-binding probes are bound to the target mRNA, enabling simultaneous detection and monitoring of multiple genes expressed in a living cell in real time. In some embodiments, the methods, compositions and kits as disclosed herein can be used to monitor the expression of at least 2, or at least 3, or at least 4, or between 4-6, or between 7-10, or between 10-15, or between 16-20 or more than 20 genes at the same time.

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein, the term "RNA binding probe" is used interchangeably with the term "RBP" and refers to an oligomer having a sequence of nucleotide bases (i.e., oligonucleotide sequence) with a subunit-to-subunit backbone that allows the RNA binding probe to hybridize to a target sequence in an mRNA molecule by Watson-Crick base pairing, to form an RBP:mRNA duplex within the target sequence. The RBP may have exact sequence complementarity to the target sequence or near complementarity. In some embodiments, a RBP can bind or specifically hybridize to an external region (i.e., an accessible surface) of the mRNA molecule, and may not inhibit translation of the mRNA. In alternative embodiments, a RBP oligomer may block or inhibit translation of the mRNA containing the target sequence, or inhibit gene transcription.

As used herein, a oligonucleotide sequence (e.g., a RNA binding primer) that is complementary to one or more of the genes described herein, refers to oligonucleotides that are capable of hybridizing under stringent conditions to at least part of the nucleotide sequence of said genes. Such hybridizable oligonucleotides will typically exhibit at least about 75% sequence identity at the nucleotide level to said genes, preferably about 80% or 85% sequence identity or more preferably about 90% or 95% or more sequence identity to said genes.

The term "primer" or "probe" as used herein in reference to a "RNA-binding probe" refers to a sequence of nucleic acid which is complementary or substantially complementary to a portion of a target mRNA of a gene of interest.

As used herein, the term "RBP composition" refers to a composition comprising one or more RBP for use in the RNA detection methods of the present invention. In some cases, such an "RBP composition" comprises a plurality of RBPs, each of which are complementary to a different target mRNA and are labeled with a different dye, as disclosed herein.

As used herein, a RBP "specifically hybridizes" to a target mRNA if the oligomer hybridizes to the target under physiological conditions, with a $T^m$ substantially greater than 37° C., preferably at least 50° C., and typically 6° C.-8° C. or higher. Such hybridization preferably corresponds to stringent hybridization conditions, selected to be about 10° C., and preferably about 5° C. lower than the thermal melting point (T[m]) for the specific sequence at a defined ionic strength and pH. At a given ionic strength and pH , the T[m] is the temperature at which 50% of a target sequence hybridizes to a complementary polynucleotide.

RBPs are described as "complementary" to the target mRNA when hybridization occurs in an antiparallel configuration between a single stranded RBP and the mRNA molecule. A double-stranded RBP molecule can be "complementary" to a mRNA, if hybridization can occur between one of the strands of the RBP and the mRNA. Complementarity (the degree that one polynucleotide is complementary with another) is quantifiable in terms of the proportion of bases in opposing strands that are expected to form hydrogen bonds with each other, according to generally accepted base-pairing rules.

As used herein, the term "target", relative to an mRNA or other nucleic acid sequence, refers to an mRNA or other nucleic acid sequence which is preferentially expressed in a live cell to be analyzed.

The term "nucleic acid" or "nucleic acid sequence" as used herein is defined as a molecule comprised of two or more deoxyribonucleotides or ribonucleotides. The exact length of the sequence will depend on many factors, which in turn depends on the ultimate function or use of the sequence. The sequence can be generated in any manner, including chemical synthesis, DNA replication, reverse transcription, or a combination thereof. Due to the amplifying nature of the present invention, the number of deoxyribonucleotide or ribonucleotide bases within a nucleic acid sequence can be virtually unlimited. The term "oligonucleotide," as used herein, is interchangeably synonymous with the term "nucleic acid sequence".

As used herein, the term "DNA" is defined as deoxyribonucleic acid.

As used herein, the term "gene" has its meaning as understood in the art. However, it will be appreciated by those of ordinary skill in the art that the term "gene" can include gene regulatory sequences (e.g., promoters, enhancers, etc.) and/or intron sequences. It will further be appreciated that definitions of gene include references to nucleic acids that do not encode proteins but rather encode functional RNA molecules such as tRNAs. For clarity, the term gene generally refers to a portion of a nucleic acid that encodes a protein; the term can optionally encompass regulatory sequences. This definition is not intended to exclude application of the term "gene" to non-protein coding expression units but rather to clarify that, in most cases, the term as used in this document refers to a protein coding nucleic acid. In some cases, the gene includes regulatory sequences involved in transcription, or message production or composition. In other embodiments, the gene comprises transcribed sequences that encode for a protein, polypeptide or peptide. In keeping with the terminology described herein, an "isolated gene" can comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof.

The term "homoduplex" as used herein refers to a double-stranded (duplex) molecule comprising two nucleic acid molecules where both nucleic acid strands are the same type of nucleic acid. In some embodiments, the term homoduplex refers to a homoduplex of dsRNA.

The term "heteroduplex" as used herein refers to a double-stranded (duplex) molecule of complementary strands of nucleic acid molecules derived from different sources, or of different nucleic acid types. One such example is the heteroduplex comprising a DNA strand which complementary base pairs with complementary RNA molecule. Another examples include, but are not limited to, are heteroduplexes formed when non-natural analogs of nucleic acids are used to bind with nucleic acids; e.g., single-stranded peptide nucleic acids, or 2'-O-methyl phosphorothioate or Morpholino oligo nucleic acids that bind with RNA.

As used herein, the term "gene expression" means transcription of the gene into an RNA copy.

As used herein, the term "fluorescent donor" is used interchangeably herein with "fluorophor donor" and refers to the radical of a fluorogenic compound which can absorb energy and is capable of transferring the energy to another fluorogenic molecule or part of a compound. Suitable donor fluorogenic molecules include, but are not limited to, coumarins and related dyes xanthene dyes such as fluoresceins, rhodols, and rhodamines, resorufins, cyanine dyes, bimanes, acridines, isoindoles, dansyl dyes, aminophthalic hydrazides such as luminol and isoluminol derivatives, aminophthalimides, aminonaphthalimides, aminobenzofurans, aminoquinolines, dicyanohydroquinones, and europium and terbium complexes and related compounds.

As used herein, the term "acceptor" is used interchangeably herein with "fluorophor acceptor" refers to a quencher which operates via fluorescence resonance energy transfer. Many acceptors can re-emit the transferred senergy as fluorescence. Examples include coumarins and related fluorophores, xanthenes such as fluoresceins, rhodols, and rhodamines, resorufins, cyanines, difluoroboradiazaindacenes, and phthalocyanines. Other chemical classes of acceptors generally do not re-emit the transferred energy. Examples include indigos, benzoquinones, anthraquinones, azo compounds, nitro compounds, indoanilines, di- and triphenyl-methanes.

As used herein, the term "quencher" refers to a chromophoric molecule or part of a compound which is capable of reducing the emission from a fluorescent donor when attached to the donor. Quenching may occur by any of several mechanisms including fluorescence resonance energy transfer, photoinduced electron transfer, paramagnetic enhancement of intersystem crossing, Dexter exchange coupling, and exciton coupling such as the formation of dark complexes.

As used herein, the term "dye" refers to a molecule or part of a compound which absorbs specific frequencies of light, including but not limited to ultraviolet light. The terms "dye" and "chromophore" are synonymous.

As used herein, the term "scanning" means obtaining intensity measurements of the fluorescent signals from the cell. Such measurements can comprise either obtaining a spatial array of intensities or a single intensity measurement per field of view. In a preferred embodiment, the scanning comprises imaging the fluorescent signals from the cell, where "imaging" means obtaining a digital representation of the fluorescent signals from the cell, and does not require a specific arrangement or display of the digital representation. In preferred embodiments, well known formats for such "imaging" are employed, including but not limited to dib, tiff, jpg, .bmp. In further preferred embodiments, the images are displayed to provide a visual representation of the image.

The term "signature" as used herein refers to the differential expression pattern or levels of expression of multiple genes in a specific type of tissue or cell, under normal or other conditions.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene and polypeptides obtained by translation of mRNA transcribed from a gene.

The term "bind(s) substantially" refers to complementary hybridization between a probe nucleic acid (e.g., a RNA-binding probe) and a target nucleic acid (e.g., a target mRNA sequence) and embraces minor mismatches that can be accommodated by reducing the stringency of the hybridization media to achieve the desired detection of the target polynucleotide sequence.

The term "hybridization" or "hybridizes" as used herein involves the annealing of a complementary sequence (e.g., a RNA binding probe) to the target nucleic acid (i.e., the sequence to be detected, e.g., mRNA target molecule). The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA, 46:453 (1960) and Doty et al., Proc. Natl. Acad. Sci. USA, 46:461 (1960) have been followed by the refinement of this process into an essential tool of modern biology.

The phrase "hybridizing specifically to" as used herein refers to the binding, duplexing or hybridizing of a nucleic acid molecule (e.g., a RNA binding probe) substantially to, or only to a particular nucleotide sequence or sequences (e.g., a target mRNA sequence) under stringent conditions when that sequence is present in a complex mixture (e.g., total cellular) DNA or RNA.

The terms "complementary" or "substantially complementary" as used herein refer to the hybridization or base pairing between nucleotides or nucleic acids, such as, for instance, between the two strands of a double stranded DNA (dsDNA) molecule or between an oligonucleotide primer (e.g., a RNA binding primer/probe) and a binding site on a single stranded nucleic acid molecule (e.g. mRNA). Complementary nucleotides are, generally, A and T (or A and U), or C and G. A nucleic acid molecule, e.g., a ssDNA molecule can be substantially complementary to a target region on a mRNA molecule. Two single stranded RNA (ssRNA) to form a dsRNA duplex, or two single standed DNA (ssDNA) molecules to form a dsDNA duplex, or a DNA:RNA hybrid duplex are said to be substantially complementary when the nucleotides of one strand, optimally aligned with appropriate nucleotide insertions or deletions, pair with at least about 80% of the nucleotides of the other strand, usually at least about 90% to 95%, and more preferably from about 98 to 100%. Alternatively, substantial complementarity exists when an RNA and/or DNA strand will hybridize under selective hybridization conditions to its complement. Typically, selective hybridization will occur when there is at least about 65% complementarity over a stretch of at least 14 to 25 nucleotides, preferably at least about 75%, more preferably at least about 90% complementarity. See M. Kanehisa, Nucleic Acids Res., 12:203 (1984), incorporated herein by reference. The term "at least a portion of" as used herein, refers to the complimentarity between a mRNA molecule and an oligonucleotide RNA binding probe/primer of at least one base pair.

Partially complementary sequences will hybridize under low stringency conditions. This is not to say that conditions of low stringency are such that non-specific binding is permitted; low stringency conditions require that the binding of two sequences to one another be a specific (i.e., selective) interaction. The absence of non-specific binding can be tested by the use of a second target which lacks even a partial degree of complementarity (e.g., less than about 30% identity); in the absence of non-specific binding the probe will not hybridize to the second non-complementary target.

The term "stringency" refers to the degree of specificity imposed on a hybridization reaction by the specific conditions used for a reaction. When used in reference to nucleic acid hybridization, stringency typically occurs in a range from about $T_m-5°$ C. (5° C. below the $T_m$ of the probe) to about 20° C., 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences. Suitably stringent hybridization conditions for nucleic acid hybridization of a primer or short probe include, e.g., 3×SSC, 0.1% SDS, at 50° C.

When used in reference to nucleic acid hybridization the art knows well that numerous equivalent conditions can be employed to comprise either low or high stringency conditions; factors such as the length and nature (DNA, RNA, base composition, modifications etc.) of the RNA probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution can be varied to generate conditions of either low or high stringency hybridization different from, but equivalent to, the above listed conditions.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene. By way of an example only, in some embodiments a RBP that is a RNAi molecule binds to a target sequence in a mRNA of a gene of interest, and inhibits or gene silence the gene.

As used herein, a "siRNA" refers to a nucleic acid that forms a double stranded RNA (dsRNA), which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116:281-297), comprises a dsRNA molecule.

The term "biomarker" means any gene, protein, or an EST derived from that gene, the expression or level of which changes between certain conditions. Where the expression of the gene correlates with a certain condition, the gene is a biomarker for that condition.

"Biomarker-derived polynucleotides" means the RNA transcribed from a biomarker gene, any cDNA or cRNA produced therefrom, and any nucleic acid derived therefrom, such as synthetic nucleic acid having a sequence derived from the gene corresponding to the biomarker gene.

The term "phenotype" refers to one or a number of total biological characteristics that define the cell or organism under a particular set of environmental conditions and factors, regardless of the actual genotype.

The term "cell culture medium" (also referred to herein as a "culture medium" or "medium") as referred to herein is a medium for culturing cells containing nutrients that maintain cell viability and support proliferation. The cell culture medium can contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The term "cell line" refers to a population of largely or substantially identical cells that has typically been derived from a single ancestor cell or from a defined and/or substantially identical population of ancestor cells. The cell line can have been or can be capable of being maintained in culture for an extended period (e.g., months, years, for an unlimited period of time). Cell lines include all those cell lines recognized in the art as such. It will be appreciated that cells acquire mutations and possibly epigenetic changes over time such that at least some properties of individual cells of a cell line can differ with respect to each other.

The term "cross-linked" as used herein refers to a covalent bond formed between a polymer chain and a second molecule. The term "cross-linking reagent" refers to an entity or agent which is an intermediate molecule to catalyze the covalent linkage of a polymer with an entity, e.g., first affinity molecule or co-stimulatory factor.

As used herein, the term "fused" means that at least one protein or peptide is physically associated with a second protein or peptide. In some embodiments, fusion is typically a covalent linkage, however, other types of linkages are encompassed in the term "fused" include, for example, linkage via an electrostatic interaction, or a hydrophobic interaction and the like. Covalent linkage can encompass linkage as a fusion protein or chemically coupled linkage, for example via a disulfide bound formed between two cysteine residues.

The terms "decrease", "reduced", "reduction", "decrease" or "inhibit" are all used herein generally to mean a decrease by a statistically significant amount. However, for avoidance of doubt, ""reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2 SD) or greater difference in a value of the marker. The term refers to statistical evidence that there is a difference. It is defined as the probability of making a decision to reject the null hypothesis when the null hypothesis is actually true. Statistical significance can be determined by t-test or using a p-value.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following, including the Examples, but the scope of the invention should not be limited thereto.

It is understood that the detailed description and the Examples that follow are illustrative only and are not to be taken as limitations upon the scope of the invention. Various changes and modifications to the disclosed embodiments, which will be apparent to those of skill in the art, can be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. All statements as to the date or representation as to the contents of these documents are based on the information available to the applicants and do not constitute any admission as to the correctness of the dates or contents of these documents.

Generally

The method of the invention can be used to quantitate the expression of any target gene, including expression of protein-encoding messenger RNA (mRNA) genes, ribosomal RNA encoding genes, and transfer RNA encoding genes. In a preferred embodiment, the expression product of the target gene expression is a mRNA. When a RNA-binding probe (RBP), e.g., a RNA or other nucleic acid, hybridizes to a target mRNA to form a duplex, the duplex is recognized and bound by the polypeptide, allowing a FRET reaction of the dyes attached to the RBP and the polypeptide.

Duplex Binding Polypeptides (DBP)

In all aspects of the present invention, a polypeptide for use in the methods, compositions and kits as disclosed herein encompass any polypeptide that binds to the RNA-binding probe-mRNA duplex in the living cell, and is also referred to herein as a "duplex-binding polypeptide" or "duplex-binding protein" or "DBP". In all aspects, a duplex-binding polypeptide as disclosed herein is a homoduplex binding protein, and binds to a homoduplex formed, for example, by the complementary base pairing of a RNA binding probe which is single stranded RNA (ssRNA) or a modified RNA or variant thereof, forming a dsRNA RBP:mRNA duplex with the target mRNA.

In some embodiments, a duplex-binding polypeptide binds is a heteroduplex binding protein which binds to heteroduplex formed, for example, by the complementary base pairing of a RNA binding probe is not ssRNA to the target mRNA. In such embodiments, a heteroduplex-binding polypeptide binds to a duplex that comprises, for example, a RBP such as, e.g., a DNA or nucleic acid analogue, e.g., locked nuclear acid (LNA), or variant thereof, that is hybridized to, or complementary based paired to, the target mRNA.

Accordingly, in some embodiments, a heteroduplex binding protein useful of the methods, compositions and kits as disclosed herein can bind to a hybrid DNA:mRNA duplex. Such heteroduplex binding polypeptides are known in the art, for example, are disclosed in WO 2013/102289, WO2001/005800 which are incorporated herein in its entirety by reference. In some embodiments, a heteroduplex binding protein that binds to a DNA:mRNA hybrid duplex comprises any of: a TALE (Transcription Activator Like Effectors, transcription activator-like effector) polypeptide, Resolvases and modified forms thereof or fragment or variant thereof a. dsRNA Binding Domains (dsRBD)

In some embodiments, the duplex binding polypeptide as disclosed herein comprises one or more dsRNA binding domain (dsRBD). These dsRNA binding domains can themselves be full length proteins with dsRNA binding activity, or fragments thereof that retain dsRNA binding activity, as well as synthetically derived polypeptide sequences that have been selected for their dsRNA binding activity, using techniques known in the art, such as Systematic Evolution of Ligands by Exponential enrichment (SELEX), as described in U.S. Pat. No. 6,110,900. The dsRNA binding polypeptide may be membrane permeant and added to the cell, or it may be encoded by an expression vector that is used to transfect the cells to be studied, thereby allowing expression of the dsRNA binding polypeptide by the cell.

Various dsRNA binding domains are known in the art to bind with high specificity and affinity to dsRNA sequences and/or structures. Examples of such dsRNA binding domains include, but are not limited to, dsRBD the ADAR family, the Staufen family, the RNase III family, including but not limited to, bacterial RNase III, yeast Rnt1p, Dicer, Drosher, the PKR family, TRBP/PACT family, TRBP family and HYL1, HEN1 family of double-stranded RNA binding proteins (dsRBP). In some embodiments, a dsRBD for use in the methods, compositions and kits as disclosed herein encompasses any dsRBD from the following double stranded RNA binding proteins (dsRBP): protein kinase R (PKR), ADAD2, ADAR1, ADAR2, TRBP2, Stau1, Dicer, X1RBPA, DGCR8, NFAR1, NFAR2, SPNR, RHA, NREBP/SON, TENR, RDE1, Kanadaptin, HYL1 or RNaseIII.

In some embodiments, a dsRBD for use in the methods, compositions and kits as disclosed herein is a dsRBD or a fragment thereof, from the protein kinase R (PKR) protein or a homologue thereof. In some embodiments, a dsRBD for use in the methods, compositions and kits as disclosed herein comprises SEQ ID NO: 1 or a protein that has at least 80% amino acid sequence identity to SEQ ID NO: 1, where SEQ ID NO: 1 is as follows:

```
                                          (SEQ ID NO: 1)
magdlsagf fmeelntyrq kqgvvlkyqe lpnsgpphdrr ftfqviidgr efpegegrsk keaknaaakl aveilnkekk aysplllttt nsseglsmgn yiglinriaq kkrltvnyeq casgvhgpeg fhykckmgqk eysigtgstk geakqlaakl aylqilseet svksdylssg sfat
```

In some embodiments, a dsRBD for use in the methods, compositions and kits as disclosed herein comprises a dsRBD or a fragment thereof from the protein kinase R (PKR) protein or a homologue thereof, where the is a tag, e.g., a Histadine tag at the N-terminus to aid the purification of the dsRBD protein. Accordingly, in some embodiments, a dsRBD for use in the methods, compositions and kits as disclosed herein comprises SEQ ID NO: 2 or a protein that has at least 80% amino acid sequence identity to SEQ ID NO: 2, where SEQ ID NO: 2 is as follows:

```
                                          (SEQ ID NO: 2)
mgsshhhhhh ssglvprgsh mmagdlsagf fmeelntyrq kqgvvlkyqe lpnsgpphdrr ftfqviidgr efpegegrsk keaknaaakl aveilnkekk aysplllttt nsseglsmgn yiglinriaq kkrltvnyeq casgvhgpeg fhykckmgqk eysigtgstk geakqlaakl aylqilseet svksdylssg sfat
```

In some embodiments, a dsRBD polypeptide comprises an amino acid sequence having at least 50% identity, at least 55% identity, at least 60% identity, at least 65% identity, at least 70% identity, at least 75% identity, at least 80% identity, preferably at least 85% identity, at least 90% identity, at least 95% identity, at least 96% identity, at least 97% identity, at least 98% identity, or at least 99% identity, and more preferably at least 99.3% identity to SEQ ID NO: 1).

In some embodiments, a dsRBD as disclosed herein, has at least 80%, or at least about 82%, or at least about 85%, or at least about 90%, or at least about 95%, or at least about 97%, or at least about 98%, or at least about 99% or more amino acid sequence identity to SEQ ID NO: 1 or a fragment of at least 20 amino acids thereof.

Double stranded RNA binding domain (dsRBD) are a small protein domains of 65-70 amino acids, typically adopting an αββα fold, whose central property is to bind to double stranded RNA (dsRNA). This domain is present in proteins implicated in many aspects of cellular life, including antiviral response, RNA editing, RNA processing, RNA transport and last but not least RNA silencing. Even though proteins containing dsRBDs can bind to very specific dsRNA targets in vivo, the binding of dsRBDs to dsRNA is commonly believed to be shape-dependent rather than sequence-specific. Recent structural information on dsRNA recognition by dsRBDs opens the possibility that this domain performs a direct readout of RNA sequence in the minor groove, allowing a global reconsideration of the principles describing dsRNA recognition by dsRBDs, which is discussed in Masliah et al., 2013; Cell Mol Life Sci., 70(11), 1875-1895 entitled: "RNA recognition by double-stranded RNA binding domains: a matter of shape and sequence", which is incorporated herein in its entirety by reference.

Accordingly, in some embodiments, as dsRBD have a highly conserved amino acid sequence, as discussed in Masliah et al., 2013; Cell Mol Life Sci., 70(11), in some embodiments, a dsRBD for use in the methods, compositions and kits as disclosed herein is a dsRBD comprises an amino acid of the consensus sequence of SEQ ID NO: 28, which is consensus sequence of dsRBD as follows:

```
                                         (SEQ ID NO: 28)
NPNNNLNELNNPGPNHNNNFNNNVNVNGGNGNSK
KNAKNNAAENALNNLNN
```

Figure 13:
FIG. 13 shows the sequence alignment of various double-stranded RNA binding domains (dsRBDs). Multiple sequence alignment of various dsRBD from human (*Homo sapiens*, Hs), fruitfly (*Drosophila melanogaster*, Dm), baker's yeast (*Saccharomyces cerevisiae*, Sc), frogs (*Xenopus leavis*, Xl), plants (*Arabidopsis thaliana*, At) and bacteria (*Escherichia coli*, Ec and *Aquifex aeolicus*, Aa). Alignment was done with Multalin and manually optimized using 3D structural information. For each sequence, the name of the protein and the dsRBD number are given in the first item. The second item corresponds to the accession code in the UniProt database (available at world-wide web: "uniprot.org"). The third item corresponds to the range of amino acid composing the dsRBD in the numbering of the full-length protein. The alignment is shaded by amino-acid conservation (>40%) and properties. The sequence consensus (>40%) (SEQ ID NO: 28), the residues conserved for the fold and/or dsRNA binding and the canonical secondary structured elements are shown below the alignment. The three regions of interaction with dsRNA are also indicated.

In some embodiments, a dsRBD is any dsRBD shown in FIG. 13 herein, or a polypeptide that has at least 80%, or at least about 82%, or at least about 85%, or at least about 90%, or at least about 95%, or at least about 97%, or at least about 98%, or at least about 99% or more amino acid sequence identity to SEQ ID NO: 3-27 or a fragment of at least 20 amino acids thereof.

In some embodiments, a polypeptide comprising a dsRBD comprises a dsRBD or a fragment thereof from human (*Homo sapiens*, Hs), fruitfly (*Drosophila melano-* gaster, Dm), baker's yeast (*Saccharomyces cerevisiae*, Sc), frogs (*Xenopus leavis*, Xl), plants (*Arabidopsis thaliana*, At) or bacteria (*Escherichia coli*, Ec and *Aquifex aeolicus*, Aa) species.

In some embodiments, a polypeptide comprising a dsRBD comprises a dsRBD or a fragment thereof from any of the dsRBD listed in Table 1.

Table 1. dsRBD useful in the methods, kits and compositions as disclosed herein. ([a] Apart for *E. coli* RNase III structure for which no coordinates have been deposited (n.d.: not deposited), PDB accession codes are given. [b] Primary references are related to each structure and are listed in the references from Masliah et al., *RNA recognition by double-stranded RNA binding domains: a matter of shape and sequence.*, Cell Mol Life Sci. 2013; 70(11): 1875-1895), which is incorporated herein in its entirety by reference. In the case of structures solved by structural genomics centers and not associated with a publication, the name of the structural genomic center is given.

| Protein Name | PDB accession Code[a] | References[b] |
|---|---|---|
| RNase III family | | |
| *E. coli* RNase III | n.d. | [38] |
| *S. cerevisiae* Rnt1p | 1T4O, 1T4N, 1T4L, 2LBS | [40-42] |
| *A. aeolicus* RNase III | 1RC7, 1YZ9, 1YYK, 1YYO, 1YYW, 2EZ6, 2NUG, 2NUF, 2NUE | [43-46] |
| *T. maritima* RNase III | 1O0W JCSG | |
| *M. musculus* Dicer | 3C4B, 3C4T | [47] |
| *S. pombe* Dcr1 | 2L6M | [48] |
| *K. polysporus* Dcr1 | 3RV0 | [49] |
| *H. sapiens* Drosha | 2KHX | [50] |
| ADAR family | | |
| *R. norvegicus* ADAR2 | 2B7T, 2B7V, 2L3C, 2L2K, 2L3J | [51, 52] |
| *D. melanogaster* ADAR | 2LJH | [53] |
| Staufen Family | | |
| *D. melanogaster* Staufen | 1STU, 1EKZ | [39, 54] |
| *M. musculus* Stau2 | 1UHZ | RIKEN |
| TRBP/PACT Family | | |
| *X. leavis* RBPA | 1DI2 | [55] |
| *H. sapiens* TRBP | 3ADL, 3LLH, 2CPN | [56, 57] |
| *H. sapiens* PACT | 2DIX | RIKEN |
| HYL1/HEN1 Family | | |
| *A. thaliana* HYL1 | 3ADI, 3ADJ, 3ADG, 2L2N, 2L2M | [56, 58] |
| *A. thaliana* HEN1 | 3HTX | [59] |
| DGCR8 Family | | |
| *H. sapiens* DGCR8 | 2YT4, 1X47 | [60] and RIKEN |
| PKR Family | | |
| *H. sapiens* PKR | 1QU6 | [61] |
| *M. musculus* PKR | 1X48, 1X49 | RIKEN |
| ILF3/SPNR family | | |
| *H. sapiens* ILF3 | 3P1X, 2L33 | NESGC |
| *H. sapiens* SPNR | 2DMY | RIKEN |
| RHA Family | | |
| *M. musculus* RHA | 2RS6, 2RS7, 1UIL, 1WHQ | [62] and RIKEN |

One of skill in the art will recognize that many other polypeptides, or peptides with RNA binding domains can be utilized in the present invention, and that various modifications to a dsRBD amino acid sequence, can be prepared using standard techniques and verified to retain specific binding between the RNA binding domain and the RNA tag.

In some embodiments, a duplex binding polypeptide that binds to a dsRNA homoduplex comprising a RNA RBP: RNA duplex in the living cell is labeled via covalent attachment of appropriate fluorophores, as discussed below.

In some embodiments, a duplex-binding polypeptide as disclosed herein comprises the dsRBD of the dsRBP PKB (also known in the art as EIF2AK1, PKR, PPP1R83, "protein phosphatase 1, regulatory subunit 83"). PKB corresponds to NP_002750.1(amino acid sequence) and is encoded by the nucleic acid sequence of of accession number: NM_002759.3 (SEQ ID NO: 75) which is as follows:

```
                                                     (SEQ ID NO: 75)
  1    agcagacgag ggcttgtgcg agaggggggcc gggcggctgc agggaaggcg gagtccaagg 61    ggaaaacgaa actgagaacc agctctcccg aagccgcggg tctccggccg gcggcggcgg 121    cggcggcggc ggcggcgcag tttgctcata ctttgtgact tgcggtcaca gtggcattca 181    gctccacact tggtagaacc acaggcacga caagcataga aacatcctaa acaatcttca 241    tcgaggcatc gaggtccatc ccaataaaaa tcaggagacc ctggctatca tagaccttag 301    tcttcgctgg tatcactcgt ctgtctgaac cagcggttgc attttttttaa gccttctttt 361    ttctcttttta ccagtttctg gagcaaattc agtttgcctt cctggatttg taaattgtaa 421    tgacctcaaa actttagcag ttcttccatc tgactcaggt ttgcttctct ggcggtcttc 481    agaatcaaca tccacacttc cgtgattatc tgcgtgcatt ttggacaaag cttccaacca 541    ggatacggga agaagaaatg gctggtgatc tttcagcagg tttcttcatg gaggaactta 601    atacataccg tcagaagcag ggagtagtac ttaaatatca agaactgcct aattcaggac 661    ctccacatga taggaggttt acatttcaag ttataataga tggaagagaa tttccagaag 721    gtgaaggtag atcaaagaag gaagcaaaaa atgccgcagc caaattagct gttgagatac
```

-continued

```
 781   ttaataagga aaagaaggca gttagtcctt tattattgac aacaacgaat tcttcagaag
 841   gattatccat ggggaattac ataggcctta tcaatagaat tgcccagaag aaaagactaa
 901   ctgtaaatta tgaacagtgt gcatcggggg tgcatgggcc agaaggattt cattataaat
 961   gcaaaatggg acagaaagaa tatagtattg gtacaggttc tactaaacag gaagcaaaac
1021   aattggccgc taaacttgca tatcttcaga tattatcaga agaaacctca gtgaaatctg
1081   actacctgtc tctggttct tttgctacta cgtgtgagtc ccaaagcaac tctttagtga
1141   ccagcacact cgcttctgaa tcatcatctg aaggtgactt ctcagcagat acatcagaga
1201   taaattctaa cagtgacagt ttaaacagtt cttcgttgct tatgaatggt ctcagaaata
1261   atcaaaggaa ggcaaaaaga tctttggcac ccagatttga ccttcctgac atgaaagaaa
1321   caaagtatac tgtggacaag aggtttggca tggattttaa agaaatagaa ttaattggct
1381   caggtggatt tggccaagtt ttcaaagcaa acacagaat tgacggaaag acttacgtta
1441   ttaaacgtgt taaatataat aacgagaagg cggagcgtga agtaaaagca ttggcaaaac
1501   ttgatcatgt aaatattgtt cactacaatg gctgttggga tggatttgat tatgatcctg
1561   agaccagtga tgattctctt gagagcagtg attatgatcc tgagaacagc aaaaatagtt
1621   caaggtcaaa gactaagtgc cttttcatcc aaatggaatt ctgtgataaa gggaccttgg
1681   aacaatggat tgaaaaaaga gaggcgaga aactagacaa agttttggct ttggaactct
1741   ttgaacaaat aacaaagggg gtggattata cattcaaa aaaattaatt catagagatc
1801   ttaagccaag taatatattc ttagtagata caaacaagt aaagattgga ctttggac
1861   ttgtaacatc tctgaaaaat gatggaaagc gaacaaggag taagggaact ttgcgataca
1921   tgagcccaga acagatttct tcgcaagact atggaaagga agtggacctc tacgctttgg
1981   ggctaattct tgctgaactt cttcatgtat gtgacactgc ttttgaaaca tcaaagtttt
2041   tcacagacct acgggatggc atcatctcag atatatttga taaaaaagaa aaaactcttc
2101   tacagaaatt actctcaaag aaacctgagg atcgacctaa cacatctgaa atactaagga
2161   ccttgactgt gtggaagaaa agcccagaga aaaatgaacg acacacatgt tagagcccctt
2221   ctgaaaaagt atcctgcttc tgatatgcag ttttccttaa attatctaaa atctgctagg
2281   gaatatcaat agatatttac cttttatttt aatgtttcct ttaatttttt actattttta
2341   ctaatctttc tgcagaaaca gaaaggtttt cttcttttg cttcaaaaac attcttacat
2401   tttactttt cctggctcat ctctttattc tttttttttt tttaaagaca gagtctcgct
2461   ctgttgccca ggctggagtg caatgacaca gtcttggctc actgcaactt ctgcctcttg
2521   ggttcaagtg attctcctgc ctcagcctcc tgagtagctg gattacaggc atgtgccacc
2581   cacccaacta ttttgtgt ttttaataaa gacagggttt caccatgttg gccaggctgg
2641   tctcaaactc ctgacctcaa gtaatccacc tgcctcggcc tcccaaagtg ctgggattac
2701   agggatgagc caccgcgccc agcctcatct ctttgttcta agatggaaaa accaccccc
2761   aaatttttctt tttatactat taatgaatca atcaattcat atctatttat taaatttcta
2821   ccgcttttag gccaaaaaaa tgtaagatcg ttctctgcct cacatagctt acaagccagc
2881   tggagaaata tggtactcat taaaaaaaaa aaaaaagtg atgtacaacc acttcggaaa
2941   acaatttggc attatctagt aaagttgaat ccatgtatac ccacatagct atcaattcta
3001   ttcctacata cgtgcttaca agaatgtcca taaacccctg tttataatag ccaaaagaac
3061   agggaacaac cataatgcac atcaaaagaa gaatggatta aaaaaattat attcacacac
3121   aggagtacta tatagtattg aaaacaattg aagtacagct aaatgtaata acgtaacaca
```

```
-continued
3181    atacaactct cagaaacata atgttaagcg aacaaagcag gttttcagaa aatatatgca 3241    gaataattcc atttatataa agttccagag catgcaaaac taaatcattt tgtataaaaa 3301    acccaacaaa tgtgatgaga caataatggg aaggaaggga atgagaaata ttaaattctg 3361    gatggtggtt atctttgagg gaggggaatg atgtgattgg ggaaatggac tttcaaaggt 3421    aatggtaact tccttaagct ggatggtagg tccactagtg tttgctgcat agttatacct 3481    tttatcttaa atacattttg tatctattgt aacaaccact ttaaagacaa ccgtgctgta 3541    aggcagtagc taaaaacaga aaatagtcca tcgggaaggg taagatggct ttctgctgag 3601    cacagggcta gaagtgacag cccagtgggc cttccaacta tatgccaggg tgttagatga 3661    gtagagagga gaccacccag gaagtctgga caagggtct ggcatgagct ctggagaaga 3721    tatatttgag gaacatgggg tatgctagtt tgttgtcctg aattgctgta gagaagataa 3781    tttaaattgc atcttagaag acgaccctga gggtgaattt caacttaggg caattgtttt 3841    agtttgtttc ttattggttt aaatggatac ttgaagctgg ataatttata aggaaaagag 3901    atttatatga cttacagttc tgcaggctgt acaagaaaca tggcaccagc atctgcttct 3961    tccccggctg cttccactca tggtggaagg tgaaggggag ccggatgtgc agagatcata 4021    tggcaagaga ggaagcaaga gagcgaggga gaaggtgcca ggctcttttt aaataaccgg 4081    ctcttgaggg aactaataga ttgagaactc cttgcttctc ctccccagca cacccaccc 4141    ccagggacgg cattaatgta ttcatgaggg gtcttccccc atgacccaaa cacctcccat 4201    caggccccac ctccaacact gggatcaaat ttcaacatga gattttgggg gacaaacatg 4261    caaactatag cagcaaccag ctaccattct aaaactgcca tatgatttta ggatttttaa 4321    aaagggccaa atttaggtta agcaaaaaaa aaaaaaaaa a
```

Modifications of the Duplex Binding Polypeptide

In some embodiments, a duplex binding polypeptide, e.g., a dsRBD useful in the methods, compositions and kits as disclosed herein can have improved properties, such as a reduction in non-specific binding or a further improvement in duplex binding, while retaining the characteristics of the wild type dsRBD. Applicants herein have demonstrated that the dsRBD of SEQ ID NO: 1 is a fragment of the full length PKR dsRBP, and only a proportion of the fragments retained their ds RNA binding ability. Accordingly, fragments of dsRBP comprising the dsRBD can be screened and purified for dsRNA binding ability using affinity chromatography using dsRNA attached to agarose beads as disclosed herein in the Examples, or other methods known by persons of ordinary skill in the art.

In some embodiments, a dsRBD for use as a duplex binding protein as disclosed herein comprises a -tag to aid purification of the dsRBD polypeptide. Tags are well known in the art and include, but are not limited to biotin, His-tags and the like. In some embodiments a His tag is used, e.g., for example a His- at the N-terminus of SEQ ID NO: 1. In some embodiments, the dsRBD comprises SEQ ID NO: 2.

Fusion Proteins

Additionally, in some embodiments, a duplex binding polypeptide, e.g., a dsRBD useful in the methods, compositions and kits as disclosed herein can be a fusion protein, where the duplex binding polypeptide, e.g., a dsRBD is fused to one or more protein dye molecules as disclosed herein. In alternative embodiments, a duplex binding polypeptide, e.g., a dsRBD is conjugated or attached to a fluorescent molecule or molecules which are synthetic, non-proteinaceous flourophores that are membrane-permeant, and thus diffuse into the cell when added to the bathing medium (see, for example, Griffin et al., 1998; Rozinov and Nolan, 1998). Specific binding of such a membrane-permeant fluorophore to duplex binding polypeptide, e.g., a dsRBD may be achieved, for example, by adding an amino acid sequence to the duplex binding polypeptide, e.g., a dsRBD (preferably outside the dsRNA-binding domain). for example, via 'molecular evolution' techniques to bind the membrane-permeant organic fluorophore with high affinity (for example, the fluorescein-binding antibody fragment described by Boder et al., 2000). In another embodiment, the fluorescent molecule or molecules comprise fluorescently-labeled synthetic peptides that are membrane-permeant (Lindgren et al, 2000), in which case a segment of said peptide is engineered to bind duplex binding polypeptide, e.g., a dsRBD, preferably does not interfere with the binding of the dsRBD to the dsRNA.

In some embodiments, the dye fused to a duplex-binding protein as disclosed herein is a donor dye, e.g., a donor fluorphore as disclosed herein. In some embodiments, the dye is fused to the N-terminus of the duplex-binding protein, e.g., a dsRBD, or alternatively, the dye is fused to the C-terminus of the duplex-binding protein. In some embodiments, the dye is fused at both the C- and N-terminus of the duplex-binding domain.

In some embodiments, a fluorophore can be attached to the amino terminus of the duplex-binding polypeptide via a direct peptide bond; or in alternative embodiments, one or more fluorophores may be linked to maleimide or iodoacetamide for attaching the fluorophore to a cysteine residue, or may be linked to isothiocyanate or succinimide ester for attaching the fluorophore to a lysine or the amino terminus of the duplex-binding polypeptide. The amino acid to which the fluorophore is attached is preferably unique within the duplex-binding polypeptide and can be placed anywhere within the duplex-binding polypeptide sequence, so long as its presence does not interfere with dsRNA binding, and in embodiments in which the duplex-binding polypeptide has been modified to comprise a membrane permeant peptide, so long as the peptide retains its ability to permeate the cell membrane.

One of ordinary skill in the art can determine a suitable location of the dye on the duplex-binding protein, and it is preferred that it does not interfere substantially with its ability to bind to dsRNA. By way of example only, one of ordinary skill of the art can assess the effect of the dye on the function of a dsRBD on binding to dsRNA and select suitable dsRBD-dye fusion protein using a dsRNA affinity chromatography as disclosed herein in the Examples.

Cell Permeable Peptides

In some embodiments, a duplex binding polypeptide, e.g., a dsRBD can be modified to be membrane permeant, to permit loading of the cells with a duplex binding polypeptide, e.g., a dsRBD simply by addition to the cell bathing medium. There are several classes of known membrane permeant peptides that can be added to the duplex binding polypeptide, e.g., a dsRBD, including but not limited to arginine rich peptides (Tan and Frankel, 1995; Futaki et al., 2001). Furthermore, it is known that the addition of certain peptide sequences to other, non-membrane permeant polypeptides, results in a chimeric polypeptide that is membrane permeant. Such peptide sequences include, but are not limited to, peptides with 4-12 arginines (e.g., a poly R amino acid sequence, e.g., 7R, 9R, 11R and the like); penetratin (RQIKIWFQNRRMKWKK) (SEQ ID NO: 67); signal sequence based peptides (GALFLGWL-GAAGSTMGAWSQPKKKRKV (SEQ ID NO: 32); AAVALLPAVLLALLAP (SEQ ID NO:33); transportan (GWTLNSAGYLLKINLKALAALAKKIL) (SEQ ID NO:34); and amphiphilic model peptide (KLALKLALKA-LKAALKLA) (SEQ ID NO:36) (Futaki et al., 2001; Lindgen et al., 2000). Other pearmeable peptides include, but are not limited to cell penetrating agents as disclosed below.

In some embodiment of the invention, a cell penetrating can be attached a duplex-binding protein as disclosed at the C- and/or N-terminus end. In some embodiments, a cell pearmeable peptide comprises amino acids 47-57 of the HIV-1 TAT peptide (SEQ ID NO:37). In another embodiment, a cell penetrating agent comprises the basic region comprising amino acids 48-60 of the HIV-1 TAT peptide (SEQ ID NO:38). In yet another embodiment, a cell penetrating agent comprises the basic region comprising amino acids 49-57, 48-60, or 47-57 of the HIV-1 TAT peptide, does not comprise amino acids 22-36 of the HIV-1 TAT peptide, and does not comprise amino acids 73-86 of the HIV-1 TAT peptide. In still another embodiment, the specific peptides set forth in Table 2, below, or fragments thereof, can be used as cell penetrating agents in the methods and compositions as disclosed herein.

TABLE 2

| PEPTIDE | SEQUENCE | SEQ ID NO: |
|---|---|---|
| HIV-1 TAT (49-57) | RKKRRQRRR | 39 |
| HIV-1 TAT (48-60) | GRKKRRQRRRTPQ | 38 |
| HIV-1 TAT (47-57) | YGRKKRRQRRR | 37 |
| Kaposi fibroblast growth factor | AAV ALL PAV LLA LLA P + VQR KRQ KLMP | 40 |
| of caiman crocodylus Ig(5) light chain | MGL GLH LLV LAA ALQ GA | 41 |
| HIV envelope glycoprotein gp41 | GAL FLG FLG AAG STM GA + PKS KRK 5 (NLS of the SV40) | 42 |
| Drosophila Antennapedia | RQI KIW FQN RRM KWK K amide | 43 |
| RGD peptide | X-RGD-X | 44 |
| influenza virus hemagglutinin envelop glycoprotein | GLFEAIAGFIENGWEGMIDGGGYC | 45 |
| transportan A | GWT LNS AGY LLG KIN LKA LAA LAK KIL | 46 |
| Pre-S-peptide | (S)DH QLN PAF | 47 |
| Somatostatin (tyr-3-octreotate) | (S)FC YWK TCT | 48 |

(s) optional Serine for coupling
italic = optional D isomer for stability

Internalization via these peptides bypasses the endocytic pathway and therefore removes the danger of rapid degradation in the harsh lysosomal environment, and can reduce the concentration required for biological efficiency compared to free oligonucleotides.

Other arginine rich peptides are also included for use as cell penetrating agents as disclosed herein. For example, a TAT analog can comprise D-amino acids and arginine-substituted TAT (47-60), RNA-binding peptides derived from virus proteins such as HIV-1 Rev, and flock house virus coat proteins, and the DNA binding sequences of leucine zipper proteins, such as cancer-related proteins c-Fos and c-Jun and the yeast transcription factor GCN4, all of which contain several arginine residues (see Futaki, et al. (2001) *J Biol Chem* 276(8):5836-5840 and Futaki, S. (2002) *Intl. Pharm* 245(1-2):1-7, which are incorporated herein by reference). In one embodiment, the arginine rich peptide contains about 4 to about 11 arginine residues. In another embodiment, the arginine residues are contiguous residues.

In another embodiment, the duplex-binding protein can comprise a membrane signal peptide or membrane translocation sequence capable of translocating across the cell membrane. A cell penetrating "signal peptide" or "signal sequence" refers to a sequence of amino acids generally of a length of about 10 to about 50 or more amino acid residues, many (typically about 55-60%) residues of which are hydrophobic such that they have a hydrophobic, lipid-soluble portion. Generally, a signal peptide is a peptide capable of penetrating through the cell membrane to allow the import and/or export of cellular proteins.

As used herein a "signal sequence", also known as a "leader sequence" can be used, when desired, to direct the peptide through a membrane of a cell. Such a sequence refers to an amino acid sequence which can be naturally present on the peptides of the present invention or provided from heterologous sources by recombinant DNA techniques.

Signal peptides can be selected from the SIGPEP database (von Heijne, Protein Sequence Data Analysis 1:4142 (1987); von Heijne and Abrahmsen, L., FEBS Letters 224:439-446 (1989)). Algorithms can also predict signal peptide sequences for use in the compositions (see, e.g., SIGFIND— Signal Peptide Prediction Server version SignalP V2.0b2, Bendtsen et al. "Improved prediction of signal peptides: SignalP 3.0." J. Mol. Biol., 340:783-795, 2004; Nielsen et al. "Identification of prokaryotic and eukaryotic signal peptides and prediction of their cleavage sites." Protein Engineering, 10:1-6, 1997; Bairoch and Boeckmann, "The SWISS-PROT protein sequence data bank: current status" Nucleic Acids Res. 22:3578-3580, 1994.). When a specific cell type is to be targeted, a signal peptide used by that cell type can be chosen. For example, signal peptides encoded by a particular oncogene can be selected for use in targeting cells in which the oncogene is expressed. Additionally, signal peptides endogenous to the cell type can be chosen for importing biologically active molecules into that cell type. Any selected signal peptide can be routinely tested for the ability to translocate across the cell membrane of any given cell type (see, e.g., U.S. Pat. No. 5,807,746, which is incorporated herein in its entirety by reference). Exemplary signal peptide sequences with membrane translocation activity include, by way of example and not limitation, those of Karposi fibroblast growth factor AAVALLPAVLLALLAPA-AADQNQLMP. (SEQ ID NO: 49) or a derivative, variant or fragment thereof.

In another embodiment of the present invention, cell penetrating agents comprise Herpes Simplex Virus VP22 tegument protein, its analogues, derivatives and variants (Elliott, G. and O'Hare, P., Gene Ther. 6:12-21 (1999); Derer, W. et al., J. Mol. Med. 77:609-613 (1999)). VP22, encoded by the UL49 gene, is a structural component of the tegument compartment of the HSV virus. A composition containing the C-terminal amino acids 159-301 of HSV VP22 protein is capable of translocating different types of cargoes into cells. Translocating activity is observed with a minimal sequence of DAATATRGRSAASRPTER-PRAPARSASRPRRPVE (SEQ ID NO: 50). Homologues of VP22 found in herpes viruses are also capable of delivery of attached compounds of interest across cell membranes (Harms, J. S. et al., J. Virol. 74:3301-3312 (2000); Dorange, F. et al., J. Gen. Virol. 81:2219-2230 (2000), which are incorporated herein in their entirety by reference).

In another embodiment the present invention, the cell penetrating peptides comprise cationic peptides with membrane translocation activity. Cationic amino acids include for example, but are not limited to, arginine, lysine, and ornithine. Active peptides with arginine rich sequences are present in the Grb2 binding protein, having the sequence RRWRRWWRRWWRRWRR (SEQ ID NO: 51) (Williams, E. J. et al., J. Biol. Chem. 272:22349-22354 (1997)) and polyarginine heptapeptide RRRRRRR (7R) (SEQ ID NO: 52), RRRRRRRRR (9R) (SEQ ID NO: 53), RRRRRRRRRRR (11R) (SEQ ID NO: 54) (Chen, L. et al., Chem. Biol. 8:1123-1129 (2001); Futaki, S. et al., J. Biol. Chem. 276:5836-5840 (2001); and Rothbard, J. B. et al., Nat. Med. 6(11):1253-7 (2000) which are incorporated herein in their entirety by reference). An exemplary cell penetrating peptide of this type has the sequence RPKKRKVRRR (SEQ ID NO: 55), which is found to penetrate the membranes of a variety of cell types. Also useful are branched cationic peptides capable of translocation across membranes, including by way of example and not limitation, $(KKKK)_2GGC$ (SEQ ID NO:56), $(KWKK)_2GCC$ (SEQ ID NO: 57), and $(RWRR)_2GGC$ (SEQ ID NO: 58) (Plank, C. et al., Human Gene Ther. 10:319-332 (1999) which are incorporated herein in their entirety by reference).

In a further embodiment, the cell penetrating peptides comprise chimeric sequences of cell penetrating peptides that are capable of translocating across cell membrane. An exemplary molecule of this type is transportan GALFLGFLGGAAGSTMGAWSQPKSKRKV (SEQ ID NO:59), a chimeric peptide derived from the first twelve amino acids of galanin and a 14 amino acid sequence from mastoporan (Pooga, M et al., Nature Biotechnol. 16:857-861 (1998). Analogues of transportans are described in Soomets, U. et al., Biochim Biophys Acta. 1467(1): 165-76 (2000) and Lindgren, M. et al. Bioconjug Chem. 11 (5):619-26 (2000). An exemplary deletion analogue, transportan-10, has the sequence AGYLLGKINLKALAALAKKIL (SEQ ID NO: 60).

Other types of cell penetrating peptides are the VT5 sequences DPKGDPKGVTVTVTVTVTGKGDPKPD (SEQ ID NO: 61), which is an amphipathic, beta-sheet forming peptide (Oehlke, J., FEBS Lett. 415(2):196-9 (1997); unstructured peptides described in Oehlke J., Biochim Biophys Acta. 1330(1):50-60 (1997); alpha helical amphipatic peptide with the sequence KLALKLALKAL-KAALKLA (SEQ ID NO: 62) (Oehlke, J. et al., Biochim Biophys Acta. 1414(1-2):127-39 (1998); sequences based on murine cell adhesion molecule vascular endothelial cadherin, amino acids 615-632 LLIILRRRIRKQAHAHSK (SEQ ID NO: 63) (Elmquist, A. et al., Exp Cell Res. 269(2):237-44 (2001); sequences based on third helix of the islet 1 gene enhancer protein RVIRVWFQNKRCKDKK (SEQ ID NO: 64) (Kilk, K. et al., Bioconjug. Chem. 12(6):911-6 (2001)); amphipathic peptide carrier Pep-1 KETWWETWWTEWSQPKKKRKV (SEQ ID NO: 65) (Morris, M. C. et al., Nat Biotechnol. 19(12):1173-6 (2001)); and the amino terminal sequence of mouse prion protein MANLGYWLLALFVTMWTDVGLCKKRPKP (SEQ ID NO: 66) (Lundberg, P. et al., Biochem. Biophys. Res. Commun. 299(1):85-90 (2002)). In some embodiments, the cell penetrating peptides are variants, fragments of derivatives of SEQ ID NOS: 32 to 67.

In some embodiments of the present invention, a cell penetrating agent does not comprise amino acids. In such an embodiment, the cell penetrating agents is a small molecule or comprises polymers of subunits other than amino acids. For example such subunits can include, but are not limited to, hydroxy amino acids, N-methyl-amino acids amino aldehydes, and the like, which result in polymers with reduced peptide bonds. Other subunit types can be used, depending on the nature of the selected backbone. A variety of backbone types can be used to order and position the sidechain guanidino and/or amidino moieties, such as alkyl backbone moieties joined by thioethers or sulfonyl groups, hydroxy acid esters (equivalent to replacing amide linkages with ester linkages), replacing the alpha carbon with nitrogen to form an aza analog, alkyl backbone moieties joined by carbamate groups, polyethyleneimines (PEIs), and amino aldehydes, which result in polymers composed of secondary amines.

Such membrane permeant polypeptides can be added to the cell at a wide range of concentrations; some arginine-rich peptides have shown no cytotoxicity when added to cells at up to 100 µM.

RNA Binding Probe (RBP)

In all aspects as disclosed herein, a RNA binding probe (RBP) useful in the methods, compositions and kits as disclosed herein comprises a nucleic acid sequence which binds to a target region on a mRNA of a gene of interest. In some embodiments, the RBP is RNA or a modified RNA, such that when it hybridizes to the mRNA it forms a dsRNA homoduplex which allows binding of a duplex-binding protein which comprises a dsRBD. In alternative embodiments, the RBP is a single stranded DNA (ssDNA) or double stranded DNA (dsDNA) or a DNA analogue, such as for example, but not limited to, Locked nucleic acid (LNA) and variants thereof, forming a heteroduplex, e.g., a DNA or LNA:mRNA heteroduplex.

In some embodiments, a RNA binding probe (RBP) useful in the methods, compositions and kits as disclosed herein can be RNA or DNA, and can be single or double stranded, and can be selected from a group comprising: oligonucleotides; and nucleic acid analogues; for example peptide-nucleic acid (PNA), pseudo-complementary PNA (pc-PNA), locked nucleic acid (LNA),) or analogue thereof.

In some embodiments, a RBP is a Tiny LNA oligonucleotide which is complementary to at least part to the mRNA target sequence of a gene of interest. In some embodiments, a RBP is an antagomir, fully 2'-O-methoxyethyl (2'-MOE), 2'-F/MOE mixmer, LNA/DNA mixmer, a tiny LNA or a combination thereof, which are complementary to, or complementary in part, to a target region of a mRNA of a gene of interest. As used herein, the term "tiny LNA" refers to a short, e.g., 6, 7, 8, 9, 10, 11 or 12-mer oligonucleotide that is comprised entirely of locked nucleic acid monomers. Tiny LNAs are described in Obad et al., (Nature Genetics, 2010, 43(4): 371-380, content of which is incorporated herein by reference. In some embodiments, the tiny LNA comprises phosphorothioate inter-sugar linkages at all positions. In some embodiments, the tiny LNA is 8 nucleotides in length and comprises phosphorothioate inter-sugar linkages at all positions.

In some embodiments, a RBP for use in the methods, compositions and kits as disclosed herein may be any suitable size, including but not limited to, in the range of 10-100 nucleotides or 10-80 nucleotides, or 20-40 nucleotides.

In some embodiments, a RBP for use in the methods, compositions and kits as disclosed herein comprises a short nucleic acid molecule, such as a DNA oligonucleotide, which can annealed to a complementary target mRNA sequence by nucleic acid hybridization to form a hybrid between the RBP and the mRNA target nucleic acid strand. The specificity of a RBP increases with its length. Thus, for example, a RBP that includes 30 consecutive nucleotides will anneal to a mRNA target sequence with a higher specificity than a corresponding RBP of only 15 nucleotides. Thus, to obtain greater specificity, RBP useful herein can be selected from RBP that include at least 5, 10, 15, 20, 25, 30, 35, 40, 45, 50 or more consecutive nucleotides.

In some embodiments, a RBP is at least 15 nucleotides in length, such as at least 5 contiguous nucleotides complementary to a target mRNA molecule. Particular lengths of RBPs that can be used to practice the methods of the present disclosure include RBPs having at least 5, at least 10, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target mRNA molecule of the gene of interest, such as a RBP of 5-60 nucleotides, 15-50 nucleotides, 15-30 nucleotides or greater.

Sequences for exemplary RBP for use in the methods, compositions and kits and as disclosed herein are shown in Table 3:

| RNA target | Probe Sequence | Target Site |
|---|---|---|
| ssRNA for EMSA, labeled | 5'-GAGTCCTTCCACGATACC-3' (SEQ ID NO: 68) | |
| ssRNA for EMSA, unlabeled | 5'-GGTATCGTGGAAGGACTC-3' (SEQ ID NO: 69) | |
| Human α-actin | 5'-GGATAGCACAGCCTGGATA-3' (SEQ ID NO: 70) | 507-489 |
| Human Myosin heavy chain a (MHCα) | 5'-GGGCATCGGTCATCTTGG-3' (SEQ ID NO: 71) | 84-67 |
| Human Myosin light chain v (MLC2v), ventricular/cardiac muscle isoform | 5'-GAGCCCCTCCTAGTCCTTC-3' (SEQ ID NO: 72) | 582-563 |
| Mouse S100A | 5'-GGAAGTCAACTTCATTGTCC-3' (SEQ ID NO: 73) | 269-250 |
| Control Probe | 5'-GAGTGCCGGCTCGCCC1TT-3' (SEQ ID NO: 74) | |

In some embodiments, a RBP can be single-stranded or double-stranded. A single-stranded oligonucleotide can have double-stranded regions and a double-stranded oligonucleotide can have single-stranded regions. A RBP can have a hairpin structure or have a dumbbell structure. A RBP can be, e.g., wherein the 5'end of the oligonucleotide is linked to the 3' end of the oligonucleotide.

Methods for preparing RBPs are described in, for example, Sambrook et al. (1989) Molecular Cloning: A Laboratory Manual, Cold Spring Harbor, N.Y.; Ausubel et al. (1987) Current Protocols in Molecular Biology, Greene Publ. Assoc. & Wiley-Intersciences.

A dye as disclosed herein is attached to aRBP. Methods for labeling and guidance in the choice of labels appropriate for various purposes are discussed, for example, in Sambrook et al., Molecular Cloning: A Laboratory Manual, Cold Spring Harbor Laboratory Press (1989) and Ausubel et al., Current Protocols in Molecular Biology, Greene Publishing Associates and Wiley-Intersciences (1987).

In some embodiment, at least one, or at least 2 or at least 3 fluorphore molecules are added to a single RNA-binding probe. In some embodiment, each RBP molecule comprises not more than one, or no more than 2 or no more than 3 fluorphore molecules.

In some embodiments, a RBP for use in the methods may be DNA or RNA or chimeric mixtures or derivatives or modified versions thereof, so long as they are still capable of binding to the mRNA of the target gene of interest. In addition to being labeled with a dye, e.g., a fluorphore acceptor, a RBP can be modified at the base moiety, sugar moiety, or phosphate backbone, and may include other appending groups or labels, so long as it is still capable of binding and hybridizing to the mRNA target molecule.

In some embodiments, a RBP can be completely DNA, completely RNA, or comprise both RNA and DNA nucleotides. It is to be understood that when the RBP is completely DNA, RNA or a mix of both, the RBP can comprise one or more oligonucleotide modifications described herein.

In some embodiments, a RBP can be a chimeric oligonucleotide. As used herein, a "chimeric" oligonucleotide" or "chimera" refers to an oligonucleotide which contains two or more chemically distinct regions, each made up of at least one monomer unit, i.e., a modified or unmodified nucleotide in the case of an oligonucleotide. Chimeric oligonucleotides can be described as having a particular motif. In some embodiments, the motifs include, but are not limited to, an alternating motif, a gapped motif, a hemi-mer motif, a uniformly fully modified motif and a positionally modified motif. As used herein, the phrase "chemically distinct region" refers to an oligonucleotide region which is different from other regions by having a modification that is not present elsewhere in the oligonucleotide or by not having a modification that is present elsewhere in the oligonucleotide. An oligonucleotide can comprise two or more chemically distinct regions. As used herein, a region that comprises no modifications is also considered chemically distinct.

A chemically distinct region can be repeated within an oligonucleotide. Thus, a pattern of chemically distinct regions in an oligonucleotide can be realized such that a first chemically distinct region is followed by one or more second chemically distinct regions. This sequence of chemically distinct regions can be repeated one or more times. Preferably, the sequence is repeated more than one time. Both strands of a double-stranded oligonucleotides can comprise these sequences. Each chemically distinct region can actually comprise as little as a single nucleotide. In some embodiments, each chemically distinct region comprises 1, 2, 3, 4, 5, 6, 7, 8, 9, 10, 11, 12, 13, 14, 15, 16, 17 or 18 nucleotides.

In some embodiments, alternating nucleotides comprise the same modification, e.g. all the odd number nucleotides in a strand have the same modification and/or all the even number nucleotides in a strand have the similar modification to the first strand. In some embodiments, all the odd number nucleotides in an oligonucleotide have the same modification and all the even numbered nucleotides have a modification that is not present in the odd number nucleotides and vice versa.

In some embodiments, when a RBP is double-stranded and both strands of the double-stranded RBP comprise the alternating modification patterns, nucleotides of one strand can be complementary in position to nucleotides of the second strand which are similarly modified. In an alternative embodiment, there is a phase shift between the patterns of modifications of the first strand, respectively, relative to the pattern of similar modifications of the second strand. Preferably, the shift is such that the similarly modified nucleotides of the first strand and second strand are not in complementary position to each other. In some embodiments, the first strand has an alternating modification pattern wherein alternating nucleotides comprise a 2'-modification, e.g., 2'-O-Methyl modification. In some embodiments, the first strand comprises an alternating 2'-O-Methyl modification and the second strand comprises an alternating 2'-fluoro modification. In other embodiments, both strands of a double-stranded oligonucleotide comprise alternating 2'-O-methyl modifications. When both strands of a double-stranded oligonucleotide comprise alternating 2'-O-methyl modifications, such 2'-modified nucleotides can be in complementary position in the duplex region. Alternatively, such 2'-modified nucleotides may not be in complementary positions in the duplex region.

In some embodiments, a RBP comprises a mix of LNA and DNA monomers, e.g., a LNA/DNA mixmer. The LNA and DNA monomers can be arranged in any pattern. In some embodiments, the LNA and DNA monomers are arranged in an alternative pattern, e.g., a LNA monomer followed by a DNA monomer. This alternating pattern can be repeated for the full length of the RBP.

For example, a RBP may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2 thiouracil, 3-(3-amino-3-N-2-carboxypropyl)uracil, (acp3)w, and 2,6-diaminopurine.

In another embodiment, a RBP can comprises at least one modified sugar moiety selected from the group including but not limited to arabinose, 2-fluoroarabinose, xylulose, and hexose.

In yet another embodiment, a RBP can comprises at least one modified phosphate backbone selected from the group including but not limited to a phosphorothioate, a phosphorodithioate, a phosphoramidothioate, a phosphoramidate, a phosphordiamidate, a methylphosphonate, an alkyl phosphotriester, and a formacetal or analog thereof. In some embodiments, the oligonucleotides may be modified to more strongly bind to the target. Examples of modifications that may enhance the binding or an RNA or DNA or to its target include but are not limited to: 2'-O-alkyl modified ribonucleotides, 2'-O-methyl ribonucleotides, 2'-orthoester modifications (including but not limited to 2'-bis(hydroxyl ethyl), and 2' halogen modifications and locked nucleic acids (LNAs).

In some embodiments, a RBP can comprise nucleotides with modified bases, modified sugar moieties, and modified phosphate backbones, for example as described in U.S. Pat. No. 5,866,336 to Nazarenko et al. Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N^6-sopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, 2,6-diaminopurine and biotinylated analogs, amongst others.

Examples of modified sugar moieties which may be used to modify nucleotides at any position on its structure include, but are not limited to arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof RNAi as RNA Binding Probe In some embodiments, a RBP for use in the methods, composition and kits as disclosed herein can hybridize to a complementary RNA, e.g., mRNA, pre-mRNA, microRNA, or pre-microRNA. In some embodiments, a RBP does not affect the function of the RNA molecule, e.g., mRNA, i.e., the RBP does not inhibit protein expression and/or translation from the RNA molecule, e.g., mRNA molecule.

In alternative embodiments, a RBP inhibits protein expression and/or translation from the RNA molecule, e.g., mRNA molecule. This can be by reducing access of the translation machinery to the target RNA transcript, thereby preventing protein synthesis. The RBP can induce cleavage of the complementary RNA by an enzyme, such RISC mediated cleavage or RNase H and thus reducing the amount of the target RNA. The RBP itself can cleave the complementary RNA, e.g., a ribozyme, RISC mediated cleavage or RNase H and thus reducing the amount of the target mRNA. The RBP, by hybridizing to the target mRNA, can inhibit binding of the target mRNA to another complementary strand.

In some embodiments, a RNA binding probe (RBP) is a RNA interference agent (RNAi). In such embodiments, the methods, compositions and kits as disclosed herein can be used to assess if a RNAi agent is effective at knocking down a target mRNA molecule, as well as the functional effect of knocking down or inhibiting the mRNA molecule in real-time in a living cell.

Accordingly, in some embodiments, where the RBP is RNA, the RNA can be single stranded RNA (ssRNA) or double stranded RNA (dsRNA) or a modified RNA. In some embodiments, a RBP can be a small inhibitory RNA (RNAi), siRNA, microRNA, shRNA, miRNA and analogues and homologues and variants thereof effective in gene silencing MicroRNAs: MicroRNAs (miRNAs or mirs) are a highly conserved class of small RNA molecules that are transcribed from DNA in the genomes of plants and animals, but are not translated into protein. Pre-microRNAs are processed into miRNAs. Processed microRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

MicroRNAs have also been implicated in modulation of pathogens in hosts. For example, see Jopling, C. L., et al., *Science* (2005) vol. 309, pp 1577-1581. Without wishing to be bound by theory, administration of a microRNA, microRNA mimic, and/or anti microRNA oligonucleotide, leads to modulation of pathogen viability, growth, development, and/or replication. In some embodiments, the oligonucleotide is a microRNA, microRNA mimic, and/or anti microRNA, wherein microRNA is a host microRNA.

The number of miRNA sequences identified to date is large and growing, illustrative examples of which can be found, for example, in: *"miRBase: microRNA sequences, targets and gene nomenclature"* Griffiths-Jones S, Grocock R I, van Dongen S, Bateman A, Enright A J. NAR, 2006, 34, Database Issue, D140-D144; *"The microRNA Registry"* Griffiths-Jones S. NAR, 2004, 32, Database Issue, D109-D111; and also on the worldwide web at microrna.dot.sanger.dot.ac.dot.uk/sequences/.

miRNA mimics: miRNA mimics represent a class of molecules that can be used to imitate the gene modulating activity of one or more miRNAs. Thus, the term "microRNA mimic" refers to synthetic non-coding RNAs (i.e. the miRNA is not obtained by purification from a source of the endogenous miRNA) that are capable of entering the RNAi pathway and regulating gene expression. miRNA mimics can be designed as mature molecules (e.g. single stranded) or mimic precursors (e.g., pri- or pre-miRNAs).

In one design, miRNA mimics are double stranded molecules (e.g., with a duplex region of between about 16 and about 31 nucleotides in length) and contain one or more sequences that have identity with the mature strand of a given miRNA. Double-stranded miRNA mimics have designs similar to as described above for double-stranded oligonucleotides.

In some embodiments, a miRNA mimic comprises a duplex region of between 16 and 31 nucleotides and one or more of the following chemical modification patterns: the sense strand contains 2'-O-methyl modifications of nucleotides 1 and 2 (counting from the 5' end of the sense oligonucleotide), and all of the Cs and Us; the antisense strand modifications can comprise 2' F modification of all of the Cs and Us, phosphorylation of the 5' end of the oligonucleotide, and stabilized internucleotide linkages associated with a 2 nucleotide 3' overhang.

Supermirs: A supermir refers to an oligonucleotide, e.g., single stranded, double-stranded or partially double-stranded, which has a nucleotide sequence that is substantially identical to an miRNA and that is antisense with respect to its target. This term includes oligonucleotides which comprise at least one non-naturally-occurring portion which functions similarly. In a preferred embodiment, the supermir does not include a sense strand, and in another preferred embodiment, the supermir does not self-hybridize to a significant extent. A supermir featured in the invention can have secondary structure, but it is substantially single-stranded under physiological conditions. A supermir that is substantially single-stranded is single-stranded to the extent that less than about 50% (e.g., less than about 40%, 30%, 20%, 10%, or 5%) of the supermir is duplexed with itself. The supermir can include a hairpin segment, e.g., sequence, preferably at the 3' end can self hybridize and form a duplex region, e.g., a duplex region of at least 1, 2, 3, or 4 and preferably less than 8, 7, 6, or 5 nucleotides, e.g., 5 nucleotides. The duplexed region can be connected by a linker, e.g., a nucleotide linker, e.g., 3, 4, 5, or 6 dTs, e.g., modified dTs. In another embodiment the supermir is duplexed with a shorter oligo, e.g., of 5, 6, 7, 8, 9, or 10 nucleotides in length, e.g., at one or both of the 3' and 5' end or at one end and in the non-terminal or middle of the supermir.

Selection of the RNA Binding Probe Sequence

A preliminary selection of sequences for use as RNA binding probes (RBP) as disclosed herein may be made having recourse to available algorithms, such as "mfold" providing data on sequences which are deemed to harbour accessible binding sites when comprised in RNA sequences. The secondary structure of the mRNA is accordingly determined by identifying potential hybridization sites that are accessible to binding by the RBP. There is a large body of evidence suggesting that heteroduplex formation is primarily constrained by local secondary structure and folding of mRNA. The composition and length of the RBP appears to be of less importance. Candidate RNA-binding probes identified by algorithm are then tested in vitro for their ability to bind an in vitro transcribed mRNA. Those able to best form heteroduplexes are retained and used as RBP in the methods, compositions and kits as disclosed herein.

Another solution to address this question of designing RBPs has focused on the selection of nucleic acid probes by empirical approaches, using oligonucleotide scanning arrays, for example. Using such arrays has reinforced the strength of empirical approaches over prediction algorithms.

Comparisons between empirical methods to determine regions of mRNA accessible to hybridization, versus those theoretically determined by the prediction algorithm, have consistently highlighted the superior strength of empirical approaches. In fact the most appropriate oligonucleotides (selected for hybridization to single stranded regions) do not correspond to the positions predicted as loops by the algorithm. Moreover it is far from clear that the single stranded regions predicted by prediction algorithms are indeed more accessible to heteroduplex formation, than stem-loops.

The following description for preparation of molecular beacon is adapted from Bratu D. (Molecular beacons: Fluorescent probes for detection of endogenous mRNAs in living cells. Methods Mol Biol 319, 1-14 (2006)). Theoretically, any sequence within a target mRNA can be chosen as a site for RBP binding. The endless possibilities give one the confidence that such regions are easily identified. However, the extent of target accessibility is primarily a consequence of complex secondary and tertiary intramolecular structures, which are difficult to predict and which can mask many of these regions. Furthermore, inside the cell, mRNAs exist in association with proteins that further occlude parts of the mRNA. Although regions involved in protein binding can only be identified by experimental analysis, reasonable attempts can be made to predict the regions that are not involved in tight secondary structures. So far, several in vitro assays and theoretical algorithms are available to help identify putative target sites within mRNA sequences, as well as probes with high affinity for binding (Tyagi, S. & Kramer, F. R. Molecular beacons: probes that fluoresce upon hybridization. Nat Biotechnol 14, 303-308 (1996); Mir, K. U. & Southern, E. M. Determining the influence of structure on hybridization using oligonucleotide arrays. Nat Biotechnol 17, 788-792 (1999); Matsuo, T. (1998). In situ visualization of messenger RNA for basic fibroblast growth factor in living cells. Biochim Biophys Acta 1379, 178-84; Sokol, D. L., Zhang, X., Lu, P. & Gewirtz, A. M. (1998). Real time detection of DNA:RNA hybridization in living cells. Proc Natl Acad Sci USA 95, 11538-43). The mfold RNA folding algorithm is used to predict the most thermodynamically stable secondary structure along with an ensemble of suboptimal structures (Southern, E. M., Milner, N. & Mir, K. U. (1997). Discovering antisense reagents by hybridization of mRNA to oligonucleotide arrays. Ciba Found Symp 209, 38-44; discussion 44-6; Ho, S. P., Bao, Y., Lesher, T., Malhotra, R., Ma, L. Y., Fluharty, S. J. & Sakai, R. R. (1998). Mapping of mRNA accessible sites for antisense experiments with oligonucleotide libraries. Nat Biotechnol 16, 59-63). Since none of these structures can be considered to represent the naturally occurring conformation, the parameters that describe the entire ensemble are analyzed. The number of candidate sites is reduced down by employing a second algorithm. OligoWalk scans the folded RNA sequence for regions to which various length oligonucleotides are capable of binding. With consideration of the base composition of each RBP oligonucleotide, and of the predicted secondary structure of the mRNA, the output provides information about the stability of the expected hybrid, and thus identifies potential target regions. Once identified, RBP for those regions can be designed and synthesized by one of ordinary skill in the art and tested empirically with in vitro synthesizedm RNA in a spectrofluorometer.

FRET

The field of the invention relates to the use of Forster resonance energy transfer (FRET), which is a mechanism describing energy transfer between two chromophores. When both chromophores are fluorescent, i.e. so-called fluorophores, the term "fluorescence resonance energy transfer" is often used instead. In order to avoid an erroneous interpretation of the phenomenon that is always a non-radiative transfer of energy (even when occurring between two fluorophores), the name "Forster resonance energy transfer" is preferred. A fluorophore donor, initially in its electronically excited state, may transfer energy to a fluorophore acceptor through non-radiative dipole-dipole coupling. The efficiency of this energy transfer is inversely proportional to the sixth power of the distance between donor and acceptor making FRET extremely sensitive to small distances.

A fluorophore is a fluorescent chemical compound that can re-emit light upon light excitation. Fluorophores typically contain several combined aromatic groups, or planar or cyclic sub-structures with several π bonds.

Measurements of FRET efficiency can be used to determine if two fluorophores are within a certain distance of each other, typically in the proximity of 1 to 10 nm. Such measurements are used as research tools in biology and chemistry. FRET is typically determined by measuring the variation in acceptor emission intensity. When the donor and acceptor are in proximity the acceptor emission will increase because of the FRET from the donor to the acceptor (sensitized emission). FRET efficiencies can also be inferred from the photobleaching rates of the donor in the presence and absence of an acceptor.

Alternatively, FRET can be measured between a fluorophore donor and a dark quencher. A dark quencher is a family of substances that absorbs emission energy from a fluorophore donor and dissipates the energy as non-UV-visible light or heat, whereas a typical "fluorescent quencher" i.e. fluorophore acceptor re-emits much of the "donated" energy as light. Black hole quencher (BHQ™) dyes from Biosearch Technologies, Inc., Novato, Calif., USA) are examples of members of the dark quencher family. Dark quenchers such as BHQ dyes are used in molecular biology in conjunction with fluorophores. When the two are close together, e.g. 10-100 A, such as in a molecule, e.g. a protein, the donor's emission is at least partially suppressed by the quencher. This effect can be used to study molecular geometry and motion.

In some embodiments, a donor dye is a fluorophore donor, which absorbs light energy of a specific wavelength (donor excitation spectrum) and emits light at a longer wavelength (donor emission spectrum). The fluorophore donor "donates" the excitation energy for the fluorophore acceptor (acceptor excitation spectrum), a fluorescent chemical that re-emits the accepted excitation energy at a longer wavelength (acceptor emission spectrum).

In some embodiments, a fluorophore donor and a spectrally paired fluorophore acceptor are useful in the methods, compositions and kits as disclosed herein. In alternative embodiments, a fluorophore donor and a spectrally paired dark quencher are useful in the methods, compositions and kits. Spectrally paired as used herein means that they are selected such that the energy spectrum emitted by the fluorophore donor (fluorophore donor emission spectrum) and the energy spectrum absorbed by the fluorophore acceptor (fluorophore acceptor excitation spectrum) or the energy absorbed by the dark quencher (quencher absorption spectrum) overlap at least partially.

a. Donor Dye

In some embodiments, a fluorophore donor useful in the methods, compositions and kits as disclosed herein is capable of absorbing radiation having a wavelength between about 300 nm to 900 nm, more preferably between 350 nm and 800 nm and is capable of transferring energy to the fluorophore acceptor or dark quencher acceptor.

In some embodiments, at least one fluorophore donor useful in the methods, compositions and kits as disclosed herein for is selected from fluorescent proteins and small fluorescent dye molecule, where the fluorescent proteins are selected from the group consisting of:

(1.1) blue fluorescent proteins, preferably selected from the group consisting of EBFP, EBFP2, Azurite and mTagBFP,
(1.2) cyan fluorescent proteins, preferably selected from the group consisting of ECFP, mECFP, Cerulean, mTurquoise, CyPet, AmCyan1, Midori-lshi Cyan, TagCFP and mTFP1 (Teal),
(1.3) yellow fluorescent proteins, preferably selected from the group consisting of EYFP, Topaz, Venus, mCitrine, YPet, TagYFP, PhiYFP, ZsYellow1 and mBanana,
(1.4) orange fluorescent proteins, preferably selected from the group consisting of Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer and mTangerine,
(1.5) red fluorescent proteins, preferably selected from the group consisting of mRuby, mApple, mStrawberry, AsRed2, mRFP1, JRed, mCherry, HcRed1, mRaspberry, dKeima-Tandem, HcRed-Tandem, mPlum and AQ143, and
(1.6) green fluorescent proteins (GFP), preferably selected from the group consisting of EGFP, Emerald, Superfolder GFP, Azami Green, mWasabi, TagGFP, TurboGFP, AcGFP, ZsGreen and T-Sapphire, more preferably green fluorescent proteins (i.6) and yellow fluorescent proteins (i.3), most preferably EGFP;

In some embodiments, a small fluorescent dye molecule useful as a donor dye in the methods, compositions and kits as disclosed herein is selected from the group consisting of:

(11.1) acridines, preferably acridine orange or acridine yellow,
(11.2) cyanines, preferably Cy2, Cy3, Cy3B, Cy3.5, Cy5, Cy5.5, Cy7,
(11.3) fluorones, preferably Fluorescein, Carboxyfluorescein, Dichlorofluorescein, Eosin, Eosin B, Eosin Y or Erythrosine, (11.4) oxazines, preferably Cresyl violet, Nile blue or Nile red,
(11.5) phenanthridines, preferably Ethidium bromide, Gelred or Propidium iodide, and
(11.6) rhodamines, preferably Rhodamine, Rhodamine 123, Rhodamine 6G, Rhodamine B, Auramine, Sulforhodamine 101, Sulforhodamine B or Texas red,
(iii) and cyanine and rhodamine dyes.

The above fluorophore donors are common knowledge in the art. For example, they are cited under e.g. fluirophores.org.

In some embodiments, a fluorophore donor is Green fluorescent protein (GFP), which features 238 amino acids and exhibits bright green fluorescence (eGFP, $Ex_{max}$=488 nm, $Em_{max}$=509 nm) upon excitation. The term Green fluorescent protein(s) as used herein is generally meant to include its derivatives, preferably those selected from the group consisting of EGFP, Emerald, Superfolder GFP, Azami Green, mWasabi, TagGFP, TurboGFP, AcGFP, ZsGreen and T-Sapphire.

In some embodiments, the fluorophore donor is a commonly used fluorophore. Fluorophores that are commonly used in FRET include, but are not limited to, fluorescein, 5-carboxyfluorescein (FAM™), 2'7'-dimethoxy-4'5'-dichloro-6-carboxyfluorescein (JOE™), rhodamine, 6-carboxyrhodamine R6G), N,N,N',N'-tetramethyl-6-carboxyrhodamine (TAMRA™), 6-carboxy-X-rhodamine (ROX™), 4-(4'-dimethylaminophenylazo)benzoic acid (DABCYL), and 5-(2'-aminoethyl)aminonaphthalene-1-sulfonic acid (EDANS). The fluorophore can be any fluorescent label known in the art, including, but not limited to: FAM™, TET™, HEX™, Cy3™, TMR™, ROX™, Texas Red®, LightCycler® Red 640, Cy5™, and LightCycler® Red 705.

Fluorophores for use in the methods, compositions and kits as disclosed herein can be chosen from, for example: 4-acetamido-4'-isothiocyanatostilbene-2,2' disulfonic acid; acridine and derivatives (e.g., acridine, acridine isothiocyanate); 5-(2'-aminoethyl)aminonaphthalene1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives (e.g., coumarin, 7-amino-4-methylcoumarin, 7-amino-4-trifluoromethylcoumarin); cyanosine; 4',6-diaminoidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylenetraimine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives (e.g., eosin, eosin isothiocyanate); erythrosine and derivatives (e.g., erythrosine B, erythrosine isothiocyanate); ethidium; fluorescein and derivatives (e.g., 5-carboxyfluorescein (FAM™), 5-(4,6-dichlorotriazin-2-yl)aminofluorescein (DTAF), 2'7'-dimethoxy-4'5'-dichloro-6-carboxyfluorescein (JOE™), fluorescein, fluorescein isothiocyanate, and QFITC (XRITC)); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives (e.g., pyrene, pyrene butyrate, succinimidyl 1-pyrene butyrate); Reactive Red 4 (Cibacron Brilliant Red 3B-A); rhodamine and derivatives (e.g., 6-carboxy-X-rhodamine (ROX™), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red®); N,N,N',N'-tetramethyl-6-carboxyrhodamine (TAMRA™); tetramethyl rhodamine (tetramethyl rhodamine isothiocyanate (TRITC)); riboflavin; rosolic acid; and terbium chelate derivatives.

Fluorophores for use in the methods disclosed herein may be obtained commercially, for example, from Biosearch Technologies (Novato, Calif.), Life Technologies (Carlsbad, Calif.), GE Healthcare (Piscataway N.J.), Integrated DNA Technologies (Coralville, Iowa) and Roche Applied Science (Indianapolis, Ind.). In some embodiments, the fluorophore is chosen to work well with a specific acceptor dye or quencher as disclosed herein. In some embodiments, if the method is designed for the detection of two or more target sequences (multiplex gene expression), and therefore two or more RNA binding probes are used, the fluorophores are chosen with absorption and emission wavelengths that are well separated from each other (have minimal spectral overlap).

In some embodiments a fluorophore donor may be on the duplex binding protein, or at the N- or C-terminal end. In alternative embodiments, a fluorophore donor may be present in the RNA binding probe, either internally, near the 5' end or at the 5' end. The fluorophore may be situated on any part of the duplex binding protein, or RBP as long as it does not interfere with the binding of the protein to the RBP:mRNA duplex, or binding of the RBP to the mRNA target sequence, respectively. The specific part of the duplex binding protein, or RBP that the fluorophore is on is not as important as the distance between the fluorophore and acceptor or quencher, when the duplex binding protein (e.g, dsRBD) binds to the RBP;mRNA duplex. Thus, the quencher/acceptor-fluorophore pair is chosen so that the fluorophore is quenchable by the acceptor/quencher when the complex of RBP;mRNA duplex is bound by the duplex binding protein (e.g., dsRBD). The distance may be different for different fluorophore-quencher/acceptor pairs.

b. Acceptors

In some embodiments, an acceptor fluorophore useful in the methods, compositions and kits as disclosed herein absorbs light at a wavelength which is at least 10 nm higher and more preferably at least 20 nm higher, most preferably at least 30 nm higher than the maximum absorbance wavelength of the donor fluorophore.

In some embodiments, an acceptor dye for use in the methods, compositions and kits as disclosed herein is a dark quencher. A dark quencher is a substance that at least partially absorbs excitation energy from the fluorophore donor and dissipates the energy as heat. In some embodiments, a dark quencher acceptor absorbs at least 30% of the emitted wavelength by the fluorophore donor, more preferably at least 50%, most preferably all of the emitted wavelength. In some embodiments, a dark quencher useful for practicing the methods compositions and kits as disclosed herein is a Black hole quencher (BHQ™) dyes.

In some embodiments, an acceptor fluorophore or dark quencher useful in the methods, compositions and kits as disclosed herein, is capable of absorbing radiation having a wavelength between about 300 nm to 900 nm, more preferably between 350 nm and 800 nm, and has an excitation spectra overlapping with the emission of the fluorophore donor, such that the energy emitted by the donor can excite the acceptor.

In some embodiments, the spectral overlap for the fluorophore donor emission spectrum and the dark quencher absorption spectrum, preferably black hole quencher (BHQ™) absorption spectrum is at least 30, preferably at least 50, 60 or 70, more preferably at least 80, most preferably at least 95 or 100%.

In some embodiments, the at least one fluorophore acceptor is selected from the group consisting of:

(i) acridines, preferably acridine orange or acridine yellow, (ii) cyanines, preferably Cy2, Cy3, Cy3B, Cy3.5, Cy5, Cy5.5 or Cy7, (iii) fluorones, preferably Fluorescein, Carboxyfluorescein, Dichlorofluorescein, Eosin, Eosin B, Eosin Y or Erythrosine, (iv) oxazines, preferably Cresyl violet, Nile blue or Nile red, (v) phenanthridines, preferably ethidium bromide, Gelred or propidium iodide, and (vi) rhodamines, preferably Rhodamine, Rhodamine 123, Rhodamine 6G, Rhodamine B, Auramine, Sulforhodamine 101, Sulforhodamine B or Texas red.

In some embodiments, a flurophore acceptor useful in the methods, compositions and kits as disclosed herein, is a cyanines, e.g., Cy3. Cyanine 3 (Cy3) is a small molecule fluorophore featuring a bright pink fluorescence ($Ex_{max}$=550 nm, $Em_{max}$=570 nm) upon excitation. In some embodiments, a Cy3 compound useful in the methods, compositions and kits as disclosed herein is attached to a ribonucleotide in the RNA binding probe by reaction with the azide (1), which has the following formula (I):

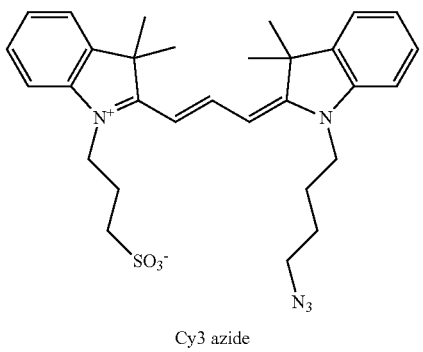

Cy3 azide

In some embodiments, at least one dark useful in the methods, compositions and kits as disclosed herein, is selected from the group consisting of Dabcyl, Dabsyl, Black Hole Quenchers (BHQ™) dyes, preferably BHQ-0, BHQ-1, BHQ-2 or BHQ-3, QXL quenchers, preferably QXL 490, QXL 570, QXL 610, QXL 670, or QXL 680, Iowa Black quenchers, preferably Iowa black FQ or Iowa Black RQ, and IRDyes, preferably IRDye 800, IRDye 800CW, IRDye 800RS, IRDye 680, IRDye 680LT, IRDye 700, or IRDye 700DX, more preferably Black Hole Quenchers (BHQ™) dyes, most preferably BHQ-1.

The term Black Hole Quenchers (BHQ™) dyes as used herein is meant to include any functional derivatives. Black hole quencher 1 (BHQ1) is a small molecule that absorbs fluorescence when excited (broad range, Ex=480 to 580 nm). In some embodiments, a BHQ1 functional derivative for demonstrating the method of the invention as illustrated in the examples is attached to a ribonucleotide in the miRNA by reaction with the azide (II), which has the following formula (II):

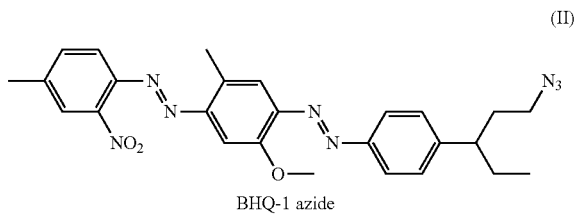 [SMILES: CCC(CCN=[N+]=[N-])c1ccc(/N=N/c2cc(C)c(/N=N/c3ccc(C)cc3[N+](=O)[O-])cc2OC)cc1]

BHQ-1 azide

In some embodiments, any quencher may be used as long as it decreases the fluorescence intensity of the fluorophore that is being used. Quenchers commonly used for FRET include, but are not limited to, Deep Dark Quencher DDQ-I, Dabcyl, Eclipse® Dark Quencher, Iowa Black® Quencher FQ, Black Hole Quenchers®, Black Hole Quencher® BHQ-1, QSY®-7 dye, Black Hole Quencher® BHQ-2, Deep Dark Quencher II (DDQ-II), Iowa Black® Quencher RQ, QSY®-21 dye, and Black Hole Quencher® BHQ-3. Quenchers for use in the methods disclosed herein may be obtained commercially, for example, from Eurogentec (Belgium), Epoch Biosciences (Bothell, Wash.), Biosearch Technologies (Novato Calif.), Integrated DNA Technologies (Coralville, Iowa) and Life Technologies (Carlsbad, Calif.).

A skilled person can readily select spectrally paired fluorophore donors and fluorophore acceptors or spectrally paired fluorophore donors and dark quenchers based on the known or easily measurable emission spectra for the donors, the known or easily measurable excitation spectra of the acceptors and the known or easily measurable absorption spectra of the dark quenchers.

In some embodiments, spectrally paired fluorophore donor and fluorophore acceptor or the spectrally paired fluorophore donor and dark quencher for practicing the method of the invention are selected from the group consisting of:

(i) protein-protein pairs, preferably selected from the group consisting of ECFP-Citrine, ECFP-Venus, Cerulean-Citrine, Cerulean-Venus, Cerulean-Ypet, Cerulean-YFP, CyPet-EYFP, CyPet-Venus, CyPet-YPet, CyPet-Citrine, mTurquoise-Venus, mTurquoise-Ypet, mTurquoise-Citrine, ECFP-EYFP, TagGFP-TagRFP, mTFP1-Citrine, Citrine-mKate2, mTurquoise1-SEYFP, mTurquoise2-SEYFP and clover-mRuby2, (ii) protein-organic dye pairs, preferably selected from the group consisting of EGFP-mCherry, SYFP2-mStrawberry, mTFP1-mOrange, Clover-mCherry, GFP-Cy3, YFP-Cy3, ECFP-BHQ-0, EYFP-BHQ-2, EGFP-Cy3 and EGFP-BHQ-1, (iii) organic dye-organic-dye pairs, preferably selected from the group consisting of: mOrange-mCherry, Alexa488-Alexa555, Alexa488-Cy3, Alexa 568-Alexa633, Cy3-Cy5, Alexa 488-Alexa514, Alexa488-Alexa532, Alexa488-546, Alexa488-610, Alexa647-Alexa 680, Alexa647-Alexa680, Alexa647-Aelxa700, Alexa647-Alexa750, BHQ-1-FAM, BHQ-1-TET, BHQ-1-JOE, BHQ-1-HEX, BHQ-1-Oregon green, BHQ-2-TAMRA, BHQ-2-ROX, BHQ-2-Cy3, BHQ-2-Cy3.5, BHQ-2-CAL Red, BHQ-2-Red 640, BHQ-3-Cy5, or BHQ-3-Cy5.5, Dabcyl-Edans and Dabsyl-Edans, fluorescine.

In some embodiments, the fluorophore pair is a donor/acceptor pair for fluorescence resonance energy transfer. In a most preferred version of this embodiment, the donor/acceptor pair is selected from the group consisting of:
fluorescein (d)+rhodamine(a)
fluorescein (d)+eosin (a)
fluorescein (d)+erythrosine (a)
fluorescein (d)+QSY-7 (a)
fluorescein (d)+ALEXA FLUOR® 54 (a)
fluorescein (d)+BODIPY®-TMR Cy3 (a)
fluorescein (d)+ALEXA FLUOR® 532 (a)
ALEXA FLUOR® 488 (d)+rhodamine (a)
ALEXA FLUOR® 488 (d)+eosin (a)
ALEXA FLUOR® 488 (d)+erythrosine (a)
ALEXA FLUOR® 488 (d)+QSY-7 (a)
ALEXA FLUOR® 488 (d)+ALEXA FLUOR® 54 (a)
ALEXA FLUOR® 488 (d)+BODIPY®-TMR Cy3 (a)
ALEXA FLUOR® 488 (d)+ALEXA FLUOR® 532 (a)
ALEXA FLUOR® 532 (d)+ALEXA FLUOR® 546 (a)
ALEXA FLUOR® 532 (d)+rhodamine (a)
ALEXA FLUOR® 350 (d)+ALEXA FLUOR® 430 (a);
ALEXA FLUOR® 430 (d)+ALEXA FLUOR® 532 (a)
ALEXA FLUOR® 430 (d)+eosin (a)
ALEXA FLUOR® 430 (d)+rhodamine (a)
ALEXA FLUOR® 430 (d)+BODIPY®-TMR Cy3 (a)

In some embodiments, the fluorophore pair is an excimer-forming pair. In a most preferred version of this embodiment, the excimer-forming pair is selected from the group consisting of a pyrene pair; and a BODIPY-FL® pair. In a further embodiment, the fluorophore pair is an exciplex-forming pair. In a most preferred version of this embodiment, the exciplex-forming pair consists of anthracene and diethylaniline.

In some embodiments a quencher or acceptor may be situated on any part of the duplex binding protein, e.g., on the surface of the protein or at the N- and/or C-terminal end.

The quencher or acceptor may be situated on any part of the duplex binding protein, or RBP as long as it does not interfere with the binding of the protein to the RBP:mRNA duplex, or binding of the RBP to the mRNA target sequence, respectively. The specific part of the duplex binding protein, or RBP that the quencher or acceptor is on is not as important as the distance between the fluorophore and acceptor or quencher, when the duplex binding protein (e.g, dsRBD) binds to the RBP;mRNA duplex. Thus, the quencher/acceptor-fluorophore pair is chosen so that the fluorophore is quenchable by the acceptor/quencher when the complex of RBP;mRNA duplex is bound by the duplex binding protein (e.g., dsRBD). The distance may be different for different fluorophore-quencher/acceptor pairs.

Cross-Linking Reagents:

In some embodiments, the dye, e.g., donor dye (e.g., fluorphore donor) or acceptor dye can be attached to a duplex-binding protein or a RNA-binding probe using a cross-linking agent. Cross-linking agents are commonly known in the art and can include bivalent or polyvalent linking agents useful in coupling protein molecules to other molecules. For example, representative coupling agents can include organic compounds such as thioesters, carbodiimides, succinimide esters, disocyanates, glutaraldehydes, diazobenzenes and hexamethylene diamines. This listing is not intended to be exhaustive of the various classes of coupling agents known in the art but, rather, is exemplary of the more common coupling agents. See Killen & Lindstrom, 133 J. Immunol. 1335 (1984); Jansen et al., 62 Imm. Rev. 185 (1982); Vitetta et al.

In some embodiments, cross-linking reagents agents described in the literature are encompassed for use in the methods, immunogenic compositions and kits as disclosed herein. See, e.g., Ramakrishnan, et al., 44 Cancer Res. 201 (1984) (describing the use of MBS (M-maleimidobenzoyl-N-hydroxysuccinimide ester)); Umemoto et al., U.S. Pat. No. 5,030,719 (describing the use of a halogenated acetyl hydrazide derivative coupled to an antibody by way of an oligopeptide linker). Particular linkers include: (a) EDC (1-ethyl-3-(3-dimethylamino-propyl) carbodiimide hydrochloride; (b) SMPT (4-succinimidyloxycarbonyl-alpha-methyl-alpha-(2-pyridyl-dithio)-toluene (Pierce Chem. Co., Cat. (21558G); (c) SPDP (succinimidyl-6 [3-(2-pyridyldithio) propionamido] hexanoate (Pierce Chem. Co., Cat #21651G); (d) Sulfo-LC-SPDP (sulfosuccinimidyl 6 [3-(2-pyridyldithio)-propianamide] hexanoate (Pierce Chem. Co. Cat. #2165-G); and (f) sulfo-NHS (N-hydroxysulfo-succinimide: Pierce Chem. Co., Cat. #24510) conjugated to EDC.

The linkages or linking agents described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage can be cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Exemplary cross-linking molecules for use in the methods and compositions as disclosed herein to attach a dye, e.g., donor dye (e.g., fluorphore donor) or acceptor dye to a duplex-binding protein or a RNA-binding probe include, but are not limited to those listed in Tables 4 and 5.

TABLE 4

Exemplary homobifunctional crosslinkers*

| Crosslinking Target | Crosslinker Reactive Groups, Features | Example Products |
|---|---|---|
| Amine-to-Amine | NHS esters | DSG; DSS; BS3; TSAT (trifunctional); Bioconjugate Toolkit Reagent Pairs |
|  | NHS esters, PEG spacer | BS(PEG)5; BS(PEG)9 |
|  | NHS esters, thiol-cleavable | DSP; DTSSP |
|  | NHS esters, misc-cleavable | DST; BSOCOES; EGS; Sulfo-EGS |
|  | Imidoesters | DMA; DMP; DMS |
|  | Imidoesters, thiol-cleavable | DTBP |
|  | Other | DFDNB; THPP (trifunctional); Aldehyde-Activated Dextran Kit |
| Sulfhydryl-to-Sulfhydryl | Maleimides | BMOE; BMB; BMH; TMEA (trifunctional) |
|  | Maleimides, PEG spacer | BM(PEG)2; BM(PEG)3 |
|  | Maleimides, cleavable | BMDB; DTME |
|  | Pyridyldithiols (cleavable) | DPDPB |
|  | Other | HBVS (vinylsulfone) |
| Nonselective | Aryl azides | BASED (thiol-cleavable) |

*crosslinking reagents that have the same type of reactive group at either end. Reagents are classified by what chemical groups they cross link (left column) and their chemical composition (middle column). Products are listed in order of increasing length within each cell.

TABLE 5

Exemplary heterobifunctional crosslinkers*

| Crosslinking Targets | Crosslinker Reactive Groups, Features | Example Products |
|---|---|---|
| Amine-to-Sulfhydryl | NHS ester/ Maleimide | AMAS; BMPS; GMBS and Sulfo-GMBS; MBS and Sulfo-MBS; SMCC and Sulfo-SMCC; EMCS and Sulfo-EMCS; SMPB and Sulfo-SMPB; SMPH; LC-SMCC; Sulfo-KMUS |
|  | NHS ester/ Maleimide, PEG spacer | SM(PEG)2; SM(PEG)4; SM(PEG)6; SM(PEG)8; SM(PEG)12; SM(PEG)24 |
|  | NHS ester/ Pyridyldithiol, cleavable | SPDP; LC-SPDP and Sulfo-LC-SPDP; SMPT; Sulfo-LC-SMPT |
|  | NHS esters/ Haloacetyl | SIA; SBAP; SIAB; Sulfo-SIAB |
| Amine-to-Nonselective | NHS ester/ Aryl Azide | NHS-ASA ANB-NOS Sulfo-HSAB Sulfo-NHS-LC-ASA SANPAH and Sulfo-SANPAH |
|  | NHS ester/ Aryl Azide, cleavable | Sulfo-SFAD; Sulfo-SAND; Sulfo-SAED |
|  | NHS ester/ Diazirine | SDA and Sulfo-SDA; LC-SDA and Sulfo-LC-SDA |
|  | NHS ester/ Diazirine, cleavable | SDAD and Sulfo-SDAD |

TABLE 5-continued

Exemplary heterobifunctional crosslinkers*

| Crosslinking Targets | Crosslinker Reactive Groups, Features | Example Products |
|---|---|---|
| Amine-to-Carboxyl | Carbodiimide | DCC; EDC |
| Sulfhydryl-to-Nonselective | Pyridyldithiol/ Aryl Azide | APDP |
| Sulfhydryl-to-Carbohydrate | Maleimide/ Hydrazide | BMPH; EMCH; MPBH; KMUH |
|  | Pyridyldithiol/ Hydrazide | BMPH; EMCH; MPBH; KMUH |
| Carbohydrate-to-Nonselective | Hydrazide/ Aryl Azide | ABH |
| Hydroxyl-to-Sulfhydryl | Isocyanate/ Maleimide | PMPI |
| Amine-to-DNA | NHS ester/ Psoralen | SPB |

*crosslinking reagents that have the different reactive groups at either end. Reagents are classified by what chemical groups they cross link (left column) and their chemical composition (middle column). Products are listed in order of increasing length within each cell.

Measuring FRET

In some embodiments, quantitation of target gene expression is achieved via fluorescence microscopy. This readout may be achieved by any of a number of means. For example, the RNA binding probe and the duplex binding protein can be labeled such that the label provides one signal when the duplex-binding protein is bound to its RBP:mRNA duplex and a different signal when not bound, thus enabling quantification of the number of RBP:mRNA duplexes formed and binding of the duplex binding protein, and thus the quantity of target RNA expressed.

When using fluorescent substrates, it will recognized that different types of fluorescent monitoring systems can be used to practice the invention. In some embodiments, FACS systems are used or systems dedicated to high throughput screening, e.g., 96 well or greater microtiter plates. Methods of performing assays on fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361.

Fluorescence in a sample can be measured using a fluorimeter. In general, excitation radiation, from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

In some embodiments, the degree of FRET can be determined by any spectral or fluorescence lifetime characteristic of the excited construct, for example, by determining the intensity of the fluorescent signal from the donor, the intensity of fluorescent signal from the acceptor, the ratio of the fluorescence amplitudes near the acceptor's emission maxima to the fluorescence amplitudes near the donor's emission maximum, or the excited state lifetime of the donor. For example, the intensity of fluorescence from the donor, or a decrease in the intensity of fluorescence from the donor or increase in intensity of fluorescence of the acceptor, or a decrease in the ratio of fluorescence amplitudes from the acceptor to that from the donor, and an increase in the excited state lifetime of the donor can be assessed.

In some embodiments, changes in the degree of FRET are determined as a function of the change in the ratio of the amount of fluorescence from the donor and acceptor moieties, a process referred to as "ratioing." Changes in the absolute amount of substrate, excitation intensity, and turbidity or other background absorbances in the sample at the excitation wavelength affect the intensities of fluorescence from both the donor and acceptor approximately in parallel. Therefore the ratio of the two emission intensities is a more robust and preferred measure of cleavage than either intensity alone.

The excitation state lifetime of the donor moiety is, likewise, independent of the absolute amount of substrate, excitation intensity, or turbidity or other background absorbances. Its measurement requires equipment with nanosecond time resolution, except in the special case of lanthanide complexes in which case microsecond to millisecond resolution is sufficient.

In some embodiments, quantitation of target gene expression is achieved via fluorescence microscopy. This readout may be achieved by any of a number of means. For example, the duplex binding protein (e.g., dsRBD) can be labeled such that the label provides one signal when it binds to the RBP:mRNA duplex and a different signal when not bound to the RBP:mRNA duplex, thus enabling quantification of the number of duplex binding proteins bound to the RBP:mRNA duplex, or number of RBP:mRNA duplexes present in the sample, and thus the quantity of target mRNA expressed. This may be accomplished when a single duplex binding protein binds to the RBP:mRNA duplex.

The efficiency of excitation of the acceptor in a FRET pair by the donor is an extremely sensitive function of the distance between donor and acceptor, and the efficiency of FRET may be measured by exciting the donor and comparing the emission intensities of the donor and the acceptor. FRET can occur when the emission spectrum of a donor overlaps significantly the absorption spectrum of an acceptor molecule, and the donor and acceptor molecules are located within less than approximately 100 Angstroms of each other. (dos Remedios and Moens, 1995. *J Struct Biol.* 115:175-85; Emmanouilidou et al. 1999, *Curr Biol.* 9:915-918.)

In some embodiments, the quantitative fluorescent readout may be achieved by other means, such as excimer or exciplex formation (Lakowicz, 1999, Chapter 1). Excimer formation involves formation of an excited state pairing of two molecules of the same fluorophore whose excitation and/or emission spectra differ greatly from those of the same fluorophore(s) when they are not interacting as a pair (*The Photonics Dictionary*, 42$^{rd}$ International Edition, Laurin Publishing Co.), while exciplex formation involves formation of an excited state pairing of two different flurophores whose excitation and/or emission spectra differ greatly from those of the same fluorophore(s) when they are not interacting as a pair Excimer or exciplex formation can be achieved either between fluors labeling two or more separate RNA-binding probes. In some embodiments, confocal fluorescence microscopy is used, for example, for assessing the binding of the RBP to the target mRNA and subsequent detection and binding of the duplex by the duplex binding protein (e.g., a dsRBP), which results in a change in the fluorescent signal. If a donor dye is present on the duplex binding protein, and the spectrally paired acceptor dye is on the RBP, when the RBP:mRNA duplex is formed and the duplex-binding protein binds, a fluorescent signal will change due to FRET, and the changed in emitted fluorescence signal will correlate with the amount of target mRNA bound/hybrizing to the RBP. Similarly and in an alternative embodiment, if an acceptor dye is present on the duplex binding protein, and the spectrally paired donor dye is on the RBP, when the RBP:mRNA duplex is formed and the duplex-binding protein binds, a fluorescent signal will change due to the occurrence of FRET, and the change in emitted fluorescence signal will correlate with the amount of target mRNA bound/hybrizing to the RBP.

FACS

In some embodiments, the fluorescence signal can be monitored and assessed by flow cytometry, for example, by Fluorescence activated cell sorting (FACS). In some embodiments, FACS can be used to isolate and collect a population of individual living cells that have a specific fluorescence signal due to the binding of dye-labeled RBP to target mRNA to form a duplex, and the binding of the duplex by a duplex binding protein that comprises a spectrally paired dye, as disclosed herein, where FACS can be used to isolate specific cells emitting a fluorescence signal indicative of a particular FRET reaction.

Accordingly, encompassed within the methods as disclosed herein, is a method to isolate a population of cells that express a gene of interest or multiple genes of interest for further study. In an exemplary embodiment, the methods disclosed herein are useful for identifying and collecting cell populations, e.g., stem cell populations, immune cells, cancer cells, cancer stem cells and the like, which express particular genes (e.g., have stem cells properties) and provide an intracellular reporter which allows isolation of this population of cells.

Accordingly, in some embodiments, the methods disclosed herein are useful for identifying and collecting a specific cell population (i.e., living cell population) that expresses a particular gene signature, from a heterologous population of cells. In some embodiments, the methods as disclosed herein can be used to isolate a specific population of cells from a heterologous population of cells, where the isolated population of cells comprises at least 80%, or at least 85% or at least 90% or more of the specific cells in the total cell population.

Gene of Interest

In some embodiments, the target gene of interest may be a gene native to the cell under study and present in the cell's genome. Alternatively, a target gene of interest may be one inserted into the genome by researchers employing molecular biological techniques such as retroviral insertion. In a further alternative, the target gene of interest may be contained in a plasmid used to stably or transiently transfect the cells under study. In some embodiment, a gene of interest is a cellular structural gene, an accessory gene or regulatory gene or any other gene relevant for the homeostasis, the regulation or metabolism of the cell.

In some embodiments, the methods, compositions and kits disclosed herein may be used for detecting the presence of one or more target sequences, quantifying one or more target sequences, and/or identifying the presence of one or more alleles of a target sequence. The target sequence may be any length that is amenable to specific hybridization by the RNA-binding probe (RBP) as disclosed herein. The target sequence may be any RNA or mRNA or nucleic acid sequence without exception.

In some embodiments, the target sequence may include but is not limited to: mRNA, tRNA, a viral sequence, a single nucleotide polymorphism (SNP), a bacterial sequence, a sequence identified with a specific disease, highly mutated nucleic acids, small interfering RNAs (siRNAs), and microRNAs (miRNAs). Thus, the methods, compositions and kits may be used in methods of diagnosis, pathogen detection, SNP/subtype/mutation detection, gene and RNA detection and/or quantification, and small RNA detection and/or quantification in individual living cells.

In some embodiments, the target nucleic acid sequence which is hybridized to by the RNA-binding probe is a non-coding RNA, e.g., a small non-coding RNA, or lncRNA or miRNA or the like, thereby allowing expression and intracellular movement of such non-coding RNAs in a living cell to be assessed.

If it is desired to quantify the expression of more than one target gene in the cell type (for example, to perform multiplex gene expression analysis), profiling of the expression of multiple genes may then be performed by growing and imaging the distinct cell lines in separate wells of a microplate, on separate domains of a miniaturized cell array (where each domain contains bound cells of a distinct cell line) (Taylor, 2000), by measuring fluorescence via a flow cytometer or, in general, by any means that allows the distinctly-tagged cell lines to be 'addressed' individually by the detection process. Such methods can be used in place of many current genomics and proteomics-based assays for determining gene expression profiles, as they can be conducted in a high throughput mode, and, since the assay utilizes intact cells, it provides data that is much more physiologically relevant than that provided by expression profiling of cDNA arrays, for example.

It may also be desirable to assess the expression of target genes whose nucleotide sequences are not known. In such cases, one may employ a non-specific RNA binding probe that binds to an unknown mRNA target sequence, and then isolating the cell and/or RNA-binding probe-mRNA duplex, and using a variety of techniques, such as restriction analysis, PCR, and cloning, to identify the gene of the target mRNA present in the duplex.

In some embodiments, a gene of interest for measuring gene expression using the methods, compositions and kits as disclosed herein can encompass genes involved in the homeostasis of cells, and especially genes of interest in the design of a therapeutic strategy or genes involved in the maintenance of the cell structure or in the regulation of the cell metabolism, including genes involved in the pathological conditions in a host, or activated as a result of such a condition, especially in a human host. A gene of interest may especially be any native mammalian gene, especially a native human gene, whose expression profile or regulation in a cell has to be studied and especially whose transcription should be studied. A gene of interest may also be a mutated version of a native gene, especially of a native mammalian, in particular human gene, whose presence and interest for cellular gene expression profiling and especially for such profiling at the transcript level should be investigated. In some embodiments, a gene of interest may also be a gene whose expression is induced or regulated in a host cell, especially a mammal cell or a human cell, as a result of a pathogen infection of the mammal or human host. In some embodiments, a gene of interest may especially be a gene regulated by or regulating immunological reactions in a host.

Examples of genes of interest according to the invention are especially genes involved in a therapeutic strategy. In a particular embodiment, they may be a target for or activated or inhibited by, either directly or indirectly, a pathogenic organism or agent, or a target for or activated or inhibited by, either directly or indirectly, a drug. They may be as such a drug or a drug candidate.

Within this definition of a "gene of interest" are the genes which are involved, either directly or indirectly, in a response to extracellular stimuli, especially to extracellular stress, such as that induced by pathogen organisms or agents or by physical stimuli such as heat or toxic chemical or biochemical compounds or pathological conditions.

In some embodiments, a gene of interest may be one involved in the immune response, in particular in the innate immune response, such as interleukins including IL10 or IL8, or cell adhesion molecules like ICAM or genes such as TgF-β, C-fos or CCL20.

In a particular embodiment genes of a determined cell that are affected by the disruption of cell gene expression or involved in dis-regulation of gene expression may be genes of interest. Examples of endogenous genes of specific cells of interest are genes involved in the homeostasis or in the development of the particular studied cells or of the entire organism comprising these cells, including but not limited to genes involved in the immune system, genes induced or silenced in pathologic conditions such as in tumor or cancer states.

Particular examples for such genes are genes encoding immunoglobulins or antigen-binding fragments thereof, especially genes encoding variable fragments of heavy chains of antibodies having an antigen-binding capacity-.Other examples include genes encoding receptors, either cellular receptors or soluble receptors, including receptors found on T lymphocytes. Particular examples of genes of the immune system that may be targeted for gene profiling encompass TgF-β, C-fos, ICAM, in particular ICAM-1, CCL20, Interferon gamma genes. Other genes of interest for gene profiling include interleukin genes, e.g. IL10 and IL8 genes. Further examples of genes of interest are genes encoding Tumor Associated Antigens., particularly genes involved in Leukemia as listed below:

For illustration purpose, the following genes indicative of adoption of LSC Fate, may be studied: L-GMP Marker Genes (Tarly) Mouse: Meis1, HoxA9, HoxA10, MYLK, HoxA5, Stau2; and for MLL-AML Marker Genes Human: Meis1, HoxA9, HoxA10, HoxA5. In another example, highly expressed genes in ALL, MLL and AML leukemias as the following may be profiled: ALL Marker Genes: MME (CD10), CD24, DYRK3, FOXO1A. MLL Marker Genes: FLT3, KIAA0428, NKG2D, ADAM-10, PROML-1, KIAA1025, LGALS-1, CCNA-1, DKFZp58600120, ITPA, CDNAag36C04, KIAA0920, LMO-2. AML Marker Genes: GJB-1, BSG, ENSA, CTSD, DF, TFDP-2, DRAP-1, NF2, CDNA20C10, PDE3B, ANPEP, Chrm19clone, Chrm22q11clone, RTN2, CRYAA.

In some embodiments, a gene of interest may be genes which are deregulated in a host, or which are induced in a host, especially a mammalian, in particular a human host, when said host is affected by a pathological condition, including for example pathologies leading to uncontrolled cell proliferation, especially cancer, or pathologies accompanied with deregulation of the immune system of the host.

In some embodiments, a gene of interest may be selected among genes which are sensitive to drugs or to other external stress factors (including pathogen organisms or agents) in a studied cell.

In some embodiments, a gene of interest may represent a candidate compound or target for a therapeutic treatment, whose expression profiling, either on or off and especially transcription profiling has to be determined after administration of this drug or stress factor.

In some embodiments, gene profiling may involve screening compounds libraries to determine the interaction of the compounds with the genes of the cell. Accordingly, the methods, compositions and kits as disclosed herein can be used to monitor gene profiling in a cell, by screening a library such as a DNA library, a RNAi library, a chemical library, a library of pathogens.

Gene profiling according to the invention encompasses monitoring of gene expression, through the observation of the transcription of gene of interests, including for example, determining the conditions to activate or elicit gene transcription (profiling on) or to inactivate gene or silence transcription (profiling off). In some embodiments, the gene profiling also relates to modulation of gene expression either to upregulate or to downregulate expression from a starting level of transcription. This may be studied at the level of one or several genes in a cell.

Living Cells for Multiplex Analysis of Gene Express in Individual Living Cells (MAGIC)

As disclosed herein, aspect of the disclosure relate to measuring the expression of multiple genes in a single living cell. In some embodiments, a cell is a living cell and in particular an individual cell. The cell may be a primary cell or a cell line.

In some embodiments, a cell or cell line is made of eukaryotic cell(s) or prokaryotic cells. In some embodiments, it is a mammalian cell or cell line especially a human cell or cell line. Alternatively, the cells are from a rodent, especially a mouse or another appropriate model animal, or from a zebra fish or from *Drosophila*.

In some embodiments, a mammalian cell or mammalian cell line is a non-human mammalian cell or cell line. In some embodiments, a cell is a differentiated cell or the cell line is derived from differentiated cells. In some embodiments, a cells are de-differentiated cells, such as, e.g., de-differentiated cells are cells that have escaped proliferation control in vivo. In some embodiments, a cell is a cancer cell or a cancer stem cell.

In some embodiments, a cell or cell line is a stem cell, e.g., an adult stem cell, embryonic stem cell, or an induced pluripotent stem cell. In some embodiments, a cell is derived from pluripotent cells or from stem cells, especially human pluripotent cells or stem cells, either embryonic or adult pluripotent or stem cells.

In some embodiments, examples of cells that may be used to perform the invention encompass cells involved in the immune system such as macrophages, dendritic cells, monocytes or epithelial cells. Other cells are cancer cells such as cells developing in breast cancer.

In some embodiments, cells can be non-polar cells such as non-polar HeLa cells, or may be polarized cells. Examples of cells used to derive cell lines include CaCo2 cells (of heterogenous human epithelial colorectal adenocarcinoma cells), U937 cells (established from a diffuse histiocytic lymphoma and displaying monocytic characteristics) or THP-1 cells (derived from monocytic leukemia).

In some embodiments, a cell or cell line as defined above and illustrated in the examples comprises one or several RNA-binding probes and at least one duplex binding protein as defined herein. As for the polynucleotide of the invention, said molecular probe(s) is (are) introduced in the cell by injection or preferably by transfection.

Other aspects of the invention also relates to a set of cells or to a set of cell lines, comprising one or several (i.e. a plurality) of RNA-binding probes and at least one duplex binding protein as defined herein.

In some embodiments, the RNA-binding probe and duplex-binding protein are introduced into the cell using standard methods, e.g., lipofectamine, electroporation and gene gun and the like. In some embodiments, the a plurality of RNA-binding probes and at least one duplex binding protein can be interoduced using nanoparticles, e.g., as part of a lipocomplex as disclosed herein.

Reagents and Kits

Also provided are reagents and kits thereof for practicing one or more of the above-described methods. The subject reagents and kits thereof may vary greatly. Reagents of interest include reagents specifically designed for use in production of the above described RNA binding probes (RBP), and duplex binding proteins (e.g., dsRBD), each of which are labeled or conjugated with a spectrally paired dye such that when the RBP hybridizes to the target mRNA of a gene of interest, the duplex is recognized and bound by the duplex binding protein and a FRET reaction occurs, which enables a detectable change in fluorescence to occur and which can be measured by fluorescence microscopy methods.

In some embodiments, the reagents provided are a duplex-binding protein, such as, for example, a dsRBD which comprises (e.g., labeled with, or fused to) a dye, e.g., a donor fluorphore or a acceptor fluorphore. In some embodiments, such a duplex-binding protein, such as, for example, a dsRBD which comprises (e.g., labeled with, or fused to) a dye, is a dry powder, e.g., a lyophilized powder.

In some embodiments, the reagents provided in a kit comprises a vector comprising a nucleic acid sequence encoding a duplex-binding protein, such as, for example, a dsRBD, where in some embodiments the nucleic acid encodes a duplex-binding protein, such as, for example, a dsRBD fused to a fluorophore, e.g., a donor or acceptor fluorophore as disclosed herein.

In some embodiments, the reagents provided in the kit include a second dye as disclosed herein, e.g., a dye that is spectrally paired with the dye present in, or attached to the duplex-binding protein. In some embodiments, the kit comprises reagents for attaching the second dye to a RNA-binding probe, for example, a RNA-binding probe provided by the kit user that specifically hybridizes to a mRNA of a gene of interest. In some embodiments, the reagents for attaching the second dye to a RNA-binding probe are cross-linkers and the like, commonly known in the art.

In some embodiments, the kit comprises one or more of: a T7 phage polymerase, ATP, CTP, GTP, aminoallyl-modified UTP, where a fluorphore can be added to UTP by amino-coupling to aminoallyl-modified uridine bases. In some embodiments, the kit also includes one or more flurophores, e.g., flurophore acceptors to be added to the RBP by amino-coupling to aminoallyl-modified uridine bases. In some embodiments, the kit also comprises reaction buffers and regents such that the kit user can in vitro transcribe RBPs that specifically hydride to their preferred target RNA, e.g., mRNA or other RNA type (e.g., small non-coding RNA). In some embodiments, the kit comprises a Alexa Fluor 647 which can be added to the amino groups on the uridine bases. The kit can comprise a number of different fluorphores, e.g., fluorphore accecpetors as described herein to allow the kit user to generate a range of dye-labeled RBP for multiplex gene expression analysis in single cells according to the methods disclosed herein. In some embodiment, the kit allows the addition of 1, 2 or 3 fluorophore molecules to be added to a single RNA-binding probe.

Accordingly, the kit can comprise include reagents employed in the various methods, such as primers for generating and in vitro transcription of target RNA-binding probes, dNTPs and/or rNTPs, which may be either premixed or separate, one or more uniquely labeled dNTPs and/or rNTPs, such as fluorophore-labeled or tagged dNTPs, with different scattering spectra, or other post synthesis labeling reagent, and various buffer mediums, e.g. hybridization and washing buffers.

In some embodiments, the kit can additionally comprise labeled RBP purification or duplex-binding protein reagents and components, like spin columns, etc., His-affinity column etc., and the like.

In some embodiments, the kit can optionally comprise one or more control RNA-binding probes, e.g., that specifically hybridize to the mRNA of a housekeeping gene(s), for example, to be used as positive controls. One such exemplary positive control RNA-binding probe comprises SEQ ID NO: 70 which binds to human α-actin mRNA. In some embodiments, a negatice control RNA-binding probe comprises SEQ ID NO: 74 as disclosed herein.

In some embodiments, the kit can optionally comprise RNA-binding probes, e.g., that specifically hybridize to the mRNA for genes known to be differentially expressed in a target population or subpopulation (e.g., reagents for detecting tumorigenic breast cancer cells can comprise RNA-binding probes that specifically hybridize to the mRNA of one or more of CD49f, CD24, and/or EPCAM).

Accordingly, the kit can be tailored to comprise one or more RNA-binding probes, or a collection or plurality of RNA-binding probes that specifically hybridize to the mRNA for a collection or plurality of genes for generating expression profiles of target cell populations and subpopulations. Gene specific primers and are described in U.S. Pat. No. 5,994,076, the disclosure of which is herein incorporated by reference. Of particular interest are kit comprising collections of RNA-binding probes that specifically hybridize to the mRNA of at least 2, or at least 3, or at least 4, or at least 5 of genes, or at least 6, 7, 8, 9, 10, 11, 12, 13, 14, 15, 20, 30, 40, 50, 60, 70, 80, 90, 100, 200, 300, 400, 500, 600, 700, 800, 900, 1000 genes or more. In some embodiments, the kit can comprise RNA-binding probe collections can include only RNA-binding probes specific for genes associated with a target population or subpopulation (e.g., mutations, known mis-regulated genes, etc.), or they may include RNA-binding probes for additional genes (e.g., housekeeping genes, controls).

Accordingly, in some embodiments, the kits of the subject invention can include the above described RNA-binding probe collections. In some embodiments, the kit can comprise RNA-binding probes that specifically hybridize to stem cell markers, e.g., to identify and purify pluripotent stem cells and the like. In some embodiments, the kit can comprise sets of RNA-binding probes that are useful in measuring gene expression of specific target populations, e.g., stem cell populations, cancer stem cell populations and the like. Accordingly, as the methods, compositions can be used to isolate cell that express a particular gene signature using FACS, the kit can be used to isolate and purify specific cell populations from a heterologous population using FACS as disclosed herein.

In some embodiments, the kits can further include a software package for statistical analysis of one or more phenotypes, and may include a reference database for calculating the statistical difference in gene expression levels of a gene of interest. The kit may include reagents employed in the various methods, such as media for expression of a fusion protein comprising a duplex-binding protein and a fluorphore, and optionally reagents for isolating and purifying said fusion protein. In some embodiments, the kit can comprise post synthesis labeling reagent, such as chemically active derivatives of fluorescent dyes, and the like, various buffer mediums, e.g. hybridization and washing buffers, prefabricated probe arrays, labeled probe purification reagents and components, like spin columns, etc., signal generation and detection reagents, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed, site. Any convenient means may be present in the kits.

The above-described analytical methods may be embodied as a program of instructions executable by computer to perform the different aspects of the invention. Any of the techniques described above may be performed by means of software components loaded into a computer or other information appliance or digital device. When so enabled, the computer, appliance or device may then perform the above-described techniques to assist the analysis of sets of values associated with a plurality of genes in the manner described above, or for comparing such associated values. The software component may be loaded from a fixed media or accessed through a communication medium such as the internet or other type of computer network. The above features are embodied in one or more computer programs may be performed by one or more computers running such programs.

In some embodiments, the kit for carrying out the methods as disclosed herein can comprises RNA-binding probes which specifically hybridize to the mRNA of at least about 20, or at least about 30, or at least about 40, or at least about 50, or at least about 60, or at least about 70, or at least about 80, or at least about 90 or more than 90 genes of interest. In some embodiments, the kit comprises RNA-binding probes which specifically hybridize to the mRNA of at least about 3 genes of interest. In some embodiments, the RNA-binding probes are labeled with a different dye, e.g., a different fluorophore dye, which is spectrally paired with the dye present on, or fused to, the duplex-binding protein, e.g., a dsRBD.

Accordingly, the present invention relates to a kit for measuring gene expression of multiple genes at the same time in a living cell or cell line, comprising reagents (e.g., duplex-binding proteins, and in some embodiments RNA-binding probes and other reagents) necessary for measuring gene expression levels of a plurality of genes in a living cell or cell line. In some embodiments, the kit further comprises instructions for use. In some embodiments, the kit comprises a computer readable medium comprising instructions encoded thereupon for running a software program on a computer to compare the levels of the expression of the gene of interests that are hybridized to the RBP in one cell as compared to another cell. In some embodiments, the kit comprises instructions to access a software program available online (e.g., on a cloud) to compare the measured levels of genes of interest from a test cell with another cell.

In some embodiments, a kit as disclosed herein also comprises at least one reagent for selecting a desired stem cell line, e.g., a pluripotent stem cell line among many cell lines, e.g., reagents to select one or more appropriate stem cell lines for the intended use of the stem cell line. Such agents are well known in the art, and include without limitation, labeled antibodies to select for cell-specific lineage markers and the like. In some embodiments, the labeled antibodies are fluorescently labeled, or labeled with magnetic beads and the like. In some embodiments, a kit as disclosed herein can further comprise at least one or more reagents for profiling and annotating an existing ES cell and/or iPS cell bank in high throughput, according to the methods as disclosed herein.

In addition to the above mentioned component(s), the kit can also include informational material. The informational material can be descriptive, instructional, marketing or other material that relates to the methods described herein and/or the use of the components for the assays, methods and systems described herein. For example, the informational material can describe methods for selecting a pluripotent stem cell, for characterizing a plurality of properties of a pluripotent cell, or generating a scorecard according to the invention. Without limitations, if a kit includes material suitable for administering to a subject, the kit can optionally include a delivery device.

Drug Screening and Other Uses

In some embodiments, the Multiplex Analysis of Gene expression in Individual living Cells ("MAGIC") system disclosed herein comprises a living cell is provided with (i) one or more RNA binding probes (RBP) which are labeled with a FRET dye, where the RNA binding probes are specific (e.g., can specifically hybridize) to the mRNA of gene(s) of interest, and (ii) a duplex binding polypeptide comprising a FRET dye that is spectrally paired with the FRET dye on the RNA binding probe, such that when the RNA binding probe hybridizes with the mRNA of gene of interest, it forms a duplex (e.g., a RNA binding probe-mRNA duplex or RBP:mRNA duplex) which is recognized and allows binding of the polypeptide, bringing the two FRET dyes into close proximity and allowing fluorescence resonance energy transfer (FRET) and a detectable change in fluorescence, which can be measured.

In some embodiments, the methods, compositions and kits as disclosed herein can be used in screening assays to screen a test compound and or in disease modeling assays.

The term "disease modeling" as used herein refers to the use of laboratory cell culture or animal research to obtain new information about human disease or illness. In some embodiments, a reprogrammed cell produced by the methods as disclosed herein can be used in disease modeling experiments. The term "drug screening" as used herein refers to the use of cells and tissues in the laboratory to identify drugs with a specific function. In some embodiments, the present invention provides drug screening to identify compounds or drugs which alter (e.g., increase or decrease) the level of expression of a set of early developmental genes, as compared to in the absence of the compound or drug.

Furthermore, with the wealth of new information now available on the molecular and cellular level of cells, and with respect to human diseases markers, it crucial to develop and test hypotheses about pathogenetic interrelations. The experimental access to specific cell types from all developmental stages and even from blastocysts deemed to harbor pathology based on pre-implantation genetic diagnosis can be useful in modeling and understanding aspects of human disease.

Importantly, in some embodiments, the methods, compositions and kits as disclosed herein can be used to assess the effect of gene expression of a gene of interest on the function of an individual living cell in real-time, which is very important to determining the pathogenic effects of a gene (e.g., a disease marker) as well as, for example, effect of a drug or other therapeutic agent (e.g., antibody or RNAi) on gene expression of a gene interest. Therefore, the methods, compositions and kits as disclosed herein can be use in the testing of drugs.

The term "marker" as used interchangeably with "biomarker" and describes the characteristics and/or phenotype of a cell. Markers can be used for selection of cells comprising characteristics of interest. Markers will vary with specific cells. Markers are characteristics, whether morphological, functional or biochemical (enzymatic) characteristics of the cell of a particular cell type, or molecules expressed by the cell type. Preferably, such markers are gene transcripts or their translation products (e.g., proteins). However, a marker can consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers can be detected by any method available to one of skill in the art. Markers can also be the absence of a morphological characteristic or absence of proteins, lipids etc. Markers can be a combination of a panel of unique characteristics of the presence and absence of polypeptides and other morphological characteristics.

Accordingly, the present invention provides methods and assays for screening a test compound for biological activity, the method comprising, not necessarily in this order: (a) obtaining a living cell and introducing into the cell a RBP and a duplex-binding protein as disclosed herein, (b) contacting the cell with a test compound; and (c) measuring a change on fluorescence of the FRET pairs of attached to the RBP and the duplex-binding protein, in the presence or absence of the test compound, where a change in the fluorescence indicates that the test compound has a biological activity that changes the level of expression a gene of interest.

As used herein, the term "biological activity" or "bioactivity" refers to the ability of a test compound to affect a biological sample. Biological activity can include, without limitation, elicitation of a stimulatory, inhibitory, regulatory, toxic or lethal response in a biological assay. For example, a biological activity can refer to the ability of a compound to modulate the effect of an enzyme, block a receptor, stimulate a receptor, modulate the expression level of one or more genes, modulate cell proliferation, modulate cell division, modulate cell morphology, or a combination thereof. In some instances, a biological activity can refer to the ability of a test compound to produce a toxic effect in a biological sample.

As used herein, the term "test compound" refers to the collection of compounds that are to be screened for their ability to have an effect on the cell. Test compounds can include a wide variety of different compounds, including chemical compounds, mixtures of chemical compounds, e.g., polysaccharides, small organic or inorganic molecules (e.g. molecules having a molecular weight less than 2000 Daltons, less than 1000 Daltons, less than 1500 Dalton, less than 1000 Daltons, or less than 500 Daltons), biological macromolecules, e.g., peptides, proteins, peptide analogs, and analogs and derivatives thereof, peptidomimetics, nucleic acids, nucleic acid analogs and derivatives, an extract made from biological materials such as bacteria, plants, fungi, or animal cells or tissues, naturally occurring or synthetic compositions.

Depending upon the particular embodiment being practiced, the test compounds can be provided free in solution, or can be attached to a carrier, or a solid support, e.g., beads. A number of suitable solid supports can be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds can be screened individually, or in groups. Group screening is particularly useful where hit rates for effective test compounds are expected to be low such that one would not expect more than one positive result for a given group.

A number of small molecule libraries are known in the art and commercially available. A comprehensive list of compound libraries can be found at http://www.broad.harvard.edu/chembio/platform/screening/compound_libraries/index.htm. A chemical library or compound library is a collection of stored chemicals usually used ultimately in high-throughput screening or industrial manufacture. The chemical library can consist in simple terms of a series of stored chemicals. Each chemical has associated information stored in some kind of database with information such as the chemical structure, purity, quantity, and physiochemical characteristics of the compound.

Without limitation, the compounds can be tested at any concentration that can exert an effect on the cells relative to a control over an appropriate time period. In some embodiments, compounds are tested at concentration in the range of about 0.01 nM to about 1000 mM, about 0.1 nM to about 500 µM, about 0.1 µM to about 20 µM, about 0.1 µM to about 10 µM, or about 0.1 µM to about 5 µM.

The compound screening assay can be used in a high through-put screen. High through-put screening is a process in which libraries of compounds are tested for a given activity. High through-put screening seeks to screen large numbers of compounds rapidly and in parallel. For example, using microtiter plates and automated assay equipment, a pharmaceutical company can perform as many as 100,000 assays per day in parallel.

The screening assay can be followed by a subsequent assay to further identify whether the identified test compound has properties desirable for the intended use. For example, the screening assay can be followed by a second assay selected from the group consisting of measurement of any of: bioavailability, toxicity, or pharmacokinetics, but is not limited to these methods.

In some embodiments, the technology described herein may be defined in any of the following numbered paragraphs:

1. A method for detection of the expression of one or more genes of interest in a living cell, comprising the steps of:
    a. providing a cell with at least one RNA binding probe (RBP) which specifically hybridizes to a target mRNA expressed by a gene of interest in the cell to form a duplex (also referred to herein as RBP-mRNA duplex), and a polypeptide which binds to a duplex,
        wherein the polypeptide is labeled with, or fused to at least a first dye, and
        wherein the at least one RNA binding probe is labeled with at least a second dye,
        wherein the first and second dyes are spectrally paired such that when juxtapositioned together, allows fluorescence resonance energy transfer (FRET) and detectable change of fluorescence,
    b. allowing the RNA binding probe to hybridize to the target mRNA to form the duplex,
    c. measuring fluorescence of the cell and detecting a change in fluorescence when the dsRBP-domain binds to the duplex, thereby detecting gene expression of the gene of interest in the living cell.
2. The method of paragraph 1, wherein the RNA binding probe comprises a nucleic acid sequence substantially complementary to the target mRNA of the gene of interest.
3. The method of paragraph 1 or 2, wherein the RNA binding probe is nucleic acid or nucleic acid analogue.
4. The method of any of paragraphs 1 to 3, wherein the RNA binding probe is selected from the group consisting of: RNA, modified RNA, DNA, ssDNA or a modified nucleic acid.
5. The method of paragraph 1, wherein the duplex is a dsRNA duplex.
6. The method of any of paragraphs 1 to 4, wherein the duplex is a heteroduplex comprising the target mRNA and ssDNA or LNA or nucleic acid analogue.
7. The method of any of paragraphs 1 to 6, wherein the RNA binding probe is a RNA or modified RNA, and the duplex is a double stranded RNA (dsRNA) duplex.
8. The method of paragraph 1, wherein the polypeptide which binds to the duplex comprises a double stranded RNA binding domain (dsRBD).
9. The method of any of paragraphs 1 to 8, wherein the dsRBD comprises a dsRBD from the ADAR family or the Staufen family.
10. The method of any of paragraphs 1 to 9, wherein the dsRBD comprises dsRBD selected from any of the following double stranded RNA binding proteins (dsRBP): protein kinase R (PKR), ADAD2, ADAR1, ADAR2, TRBP2, Stau1, Dicer, X1RBPA, DGCR8, NFAR1, NFAR2, SPNR, RHA, NREBP/SON, TENR, RDE1, Kanadaptin, HYL1 or RNaseIII.
11. The method of any of paragraphs 1 to 10, wherein the dsRBD is from protein kinase R (PKR) or a homologue thereof.
12. The method of any of paragraphs 1 to 11, wherein the dsRBD comprises SEQ ID NO: 1 or a protein that has at least 80% amino acid sequence identity to SEQ ID NO: 1.
13. The method of any of paragraphs 1 to 12, wherein the dsRBD comprises an amino acid of the consensus sequence of SEQ ID NO: 28.
14. The method of any of the above paragraphs, comprising at least 2 RNA binding probes, wherein each RNA binding probe hybridizes to a different target mRNA expressed by a gene of interest in the cell, and wherein each RNA binding probe comprises a different second dye.
15. The method of any of the above paragraphs, comprising at least 3-5 RNA binding probes, wherein each RNA binding probe hybridizes to a different target mRNA expressed by a gene of interest in the cell, and wherein each RNA binding probe comprises a different second dye.
16. The method of any of the above paragraphs, comprising at least 6-10 RNA binding probes, wherein each RNA binding probe hybridizes to a different target mRNA expressed by a gene of interest in the cell, and wherein each RNA binding probe comprises a different second dye.
17. The method of any of paragraphs 1 to 16, wherein the first dye is a donor dye (also referred to herein as flurophore donor) and the second dye is an acceptor dye (also referred to herein as quencher or dark quencher).
18. The method of any of paragraphs 1 to 17, wherein the first dye is an acceptor dye and the second dye is a donor dye.
19. The method of any of paragraphs 17 and 18, wherein the donor dye is a fluorescent donor dye (also referred to herein as flurophore donor) and the acceptor dye is a fluorescent acceptor dye (also referred to herein as flurophore acceptor, quencher or dark quencher).
20. The method of any of paragraphs 1 to 19, wherein the fluorophore donor is selected from fluorescent proteins and small fluorescent dye molecule, wherein
    (iv) fluorescent proteins are selected from the group consisting of
        a. blue fluorescent proteins, preferably selected from the group consisting of EBFP, EBFP2, Azurite and imTagBFP,
        b. cyan fluorescent proteins, preferably selected from the group consisting of ECFP, mECFP, Cerulean, mTurquoise, CyPet, AmCyan1, Midori-lshi Cyan, TagCFP and mTFP1 (Teal),
        c. yellow fluorescent proteins, preferably selected from the group consisting of EYFP, Topaz, Venus, mCitrine, YPet, TagYFP, PhiYFP, ZsYellow1 and mBanana,
        d. orange fluorescent proteins, preferably selected from the group consisting of Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer and mTangerine,
        e. red fluorescent proteins, preferably selected from the group consisting of mRuby, mApple, mStrawberry, AsRed2, mRFP1, JRed, mCherry, HcRed1, mRaspberry, dKeima-Tandem, HcRed-Tandem, mPlum and AQ143,
        f. green fluorescent proteins (GFP), selected from the group consisting of EGFP, Emerald, Superfolder GFP, Azami Green, mWasabi, TagGFP, TurboGFP, AcGFP, ZsGreen and T-Sapphire,
(v) small fluorescent dye molecules selected from the group consisting of
a. acridines, selected from: acridine orange or acridine yellow,
b. cyanines, selected from: Cy2, Cy3, Cy3B, Cy3.5, Cy5, Cy5.5, Cy7,
c. fluorones, selected from: Fluorescein, Carboxyfluorescein, Dichlorofluorescein, Eosin, Eosin B, Eosin Y or Erythrosine,
d. oxazines, selected from: Cresyl violet, Nile blue or Nile red,
e. phenanthridines, selected from: Ethidium bromide, Gelred or Propidium iodide, and
f. rhodamines, selected from: Rhodamine, Rhodamine 123, Rhodamine 6G, Rhodamine B, Auramine, Sulforhodamine 101, Sulforhodamine B or Texas red, 21. The method of any of paragraphs 1 to 19, wherein the fluorophore acceptor is selected from the group consisting of
(i) acridines, selected from acridine orange or acridine yellow,
(ii) cyanines, selected from Cy2, Cy3, Cy3B, Cy3.5, Cy5, Cy5.5 or Cy7,
(vi) fluorones, selected from Fluorescein, Carboxyfluorescein, Dichlorofluorescein, Eosin, Eosin B, Eosin Y or Erythrosine,
(vii) oxazines, preferably Cresyl violet, Nile blue or Nile red,
(viii) phenanthridines, preferably ethidium bromide, Gelred or propidium iodide, and
(ix) rhodamines, preferably Rhodamine, Rhodamine 123, Rhodamine 6G,
(x) Rhodamine B, Auramine, Sulforhodamine 101, Sulforhodamine B or Texas red, preferably cyanines (ii), more preferably Cy3.

22. The method of any of paragraphs 1 to 21, wherein the dark quencher selected from the group consisting of Dabcyl, Dabsyl, Black Hole Quencher (BHQ™) dyes, preferably BHQ-0, BHQ-1, BHQ-2 or BHQ-3, QXL quenchers, preferably QXL 490, QXL 570, QXL 610, QXL 670, or QXL 680, Iowa Black quenchers, preferably Iowa black FQ or Iowa Black RQ, and IRDyes, preferably IRDye 800, IRDye 800CW, IRDye 800RS, IRDye 680, IRDye 680LT, IRDye 700, or IRDye 700DX, more preferably Black Hole Quencher (BHQ™) dyes, most preferably BHQ-1.

23. The method of any of paragraphs 1 to 22, wherein the spectrally paired fluorophore donor and fluorophore acceptor, or the spectrally paired fluorophore donor and dark quencher are selected from the group consisting of:
a. protein-protein pairs, selected from the group consisting of ECFP-Citrine, ECFP-Venus, Cerulean-Citrine, Cerulean-Venus, Cerulean-Ypet, Cerulean-YFP, CyPet-EYFP, CyPet-Venus, CyPet-YPet, CyPet-Citrine, mTurquoise-Venus, mTurquoise-Ypet, mTurquoise-Citrine, ECFP-EYFP, TagGFP-TagRFP, mTFP1-Citrine, Citrine-mKate2, mTurquoise1-SEYFP, mTurquoise2-SEYFP and clover-mRuby2,
b. protein-organic dye pairs, selected from the group consisting of EGFP-mCherry, SYFP2-mStrawberry, mTFP1-mOrange, Clover-mCherry, GFP-Cy3, YFP-Cy3, ECFP-BHQ-0, EYFP-BHQ-2, EGFP-Cy3 and EGFP-BHQ-1,
c. organic dye-organic-dye pairs, selected from the group consisting of mOrange-mCherry, Alexa488-Alexa555, Alexa488-Cy3, Alexa 568-Alexa633, Cy3-Cy5, Alexa 488-Alexa514, Alexa488-Alexa532, Alexa488-546, Alexa488-610, Alexa647-Alexa 680, Alexa647-Alexa680, Alexa647-Aelxa700, Alexa647-Alexa750, BHQ-1-FAM, BHQ-1-TET, BHQ-1-JOE, BHQ-1-HEX, BHQ-1-Oregon green, BHQ-2-TAMRA, BHQ-2-ROX, BHQ-2-Cy3, BHQ-2-Cy3.5, BHQ-2-CAL Red, BHQ-2-Red 640, BHQ-3-Cy5, or BHQ-3-Cy5.5, Dabcyl-Edans and Dabsyl-Edans, fluorescine.

24. A set of probes comprising;
a. a polypeptide comprising a double stranded RNA binding domain (dsRBD) labeled with, or fused to, at least a first dye,
b. at least one RNA binding probe which hybridizes to a target mRNA expressed by a gene of interest in a cell to form a duplex, wherein the at least one RNA binding probe is labeled with a second dye,
wherein the first and second dyes are spectrally paired such that when juxtapositioned together, fluorescence resonance energy transfer (FRET) occurs and detectable change of fluorescence.

25. The probes of paragraph 24, wherein the first dye is a donor dye (also referred to herein as flurophore donor) and the second dye is an acceptor dye (also referred to herein as quencher or dark quencher).

26. The probes of paragraph 24, wherein the first dye is an acceptor dye and the second dye is a donor dye.

27. The probes of paragraphs 25 and 26, wherein the donor dye is a fluorescent donor dye (also referred to herein as flurophore donor) and the acceptor dye is a fluorescent acceptor dye (also referred to herein as flurophore acceptor, quencher or dark quencher).

28. The probes of any of paragraphs 24 to 27, wherein the fluorophore donor is selected from fluorescent proteins and small fluorescent dye molecule, wherein
(xi) fluorescent proteins are selected from the group consisting of
a. blue fluorescent proteins, preferably selected from the group consisting of EBFP, EBFP2, Azurite and imTagBFP,
b. cyan fluorescent proteins, preferably selected from the group consisting of ECFP, mECFP, Cerulean, mTurquoise, CyPet, AmCyan1, Midori-lshi Cyan, TagCFP and mTFP1 (Teal),
c. yelllow fluorescent proteins, preferably selected from the group consisting of EYFP, Topaz, Venus, mCitrine, YPet, TagYFP, PhiYFP, ZsYellow1 and
d. orange fluorescent proteins, preferably selected from the group consisting of Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer and mTangerine,
e. red fluorescent proteins, preferably selected from the group consisting of mRuby, mApple, mStrawberry, AsRed2, mRFP1, JRed, mCherry, HcRed1, mRaspberry, dKeima-Tandem, HcRed-Tandem, mPlum and AQ143,
f. green fluorescent proteins (GFP), selected from the group consisting of EGFP, Emerald, Superfolder GFP, Azami Green, mWasabi, TagGFP, TurboGFP, AcGFP, ZsGreen and T-Sapphire,
(xii) small fluorescent dye molecules selected from the group consisting of
a. acridines, selected from: acridine orange or acridine yellow,
b. cyanines, selected from: Cy2, Cy3, Cy3B, Cy3.5, Cy5, Cy5.5, Cy7,
c. fluorones, selected from: Fluorescein, Carboxyfluorescein, Dichlorofluorescein, Eosin, Eosin B, Eosin Y or Erythrosine,
d. oxazines, selected from: Cresyl violet, Nile blue or Nile red,
e. phenanthridines, selected from: Ethidium bromide, Gelred or Propidium iodide, and
f. rhodamines, selected from: Rhodamine, Rhodamine 123, Rhodamine 6G, Rhodamine B, Auramine, Sulforhodamine 101, Sulforhodamine B or Texas red, 29. The probes of any of paragraphs 24 to 28, wherein the fluorophore acceptor is selected from the group consisting of
(i) acridines, selected from acridine orange or acridine yellow,
(ii) cyanines, selected from Cy2, Cy3, Cy3B, Cy3.5, Cy5, Cy5.5 or Cy7,
(xiii) fluorones, selected from Fluorescein, Carboxyfluorescein, Dichlorofluorescein, Eosin, Eosin B, Eosin Y or Erythrosine,
(xiv) oxazines, preferably Cresyl violet, Nile blue or Nile red,
(xv) phenanthridines, preferably ethidium bromide, Gelred or propidium iodide, and
(xvi) rhodamines, preferably Rhodamine, Rhodamine 123, Rhodamine 6G,
(xvii) Rhodamine B, Auramine, Sulforhodamine 101, Sulforhodamine B or Texas red, preferably cyanines (ii), more preferably Cy3.

30. The probes of any of paragraphs 24 to 29, wherein the dark quencher selected from the group consisting of Dabcyl, Dabsyl, Black Hole Quencher (BHQ™) dyes, preferably BHQ-0, BHQ-1, BHQ-2 or BHQ-3, QXL quenchers, preferably QXL 490, QXL 570, QXL 610, QXL 670, or QXL 680, Iowa Black quenchers, preferably Iowa black FQ or Iowa Black RQ, and IRDyes, preferably IRDye 800, IRDye 800CW, IRDye 800RS, IRDye 680, IRDye 680LT, IRDye 700, or IRDye 700DX, more preferably Black Hole Quencher (BHQ™) dyes, most preferably BHQ-1.

31. The probes of any of paragraphs 24 to 30, wherein the spectrally paired fluorophore donor and fluorophore acceptor, or the spectrally paired fluorophore donor and dark quencher are selected from the group consisting of:
a. protein-protein pairs, selected from the group consisting of ECFP-Citrine, ECFP-Venus, Cerulean-Citrine, Cerulean-Venus, Cerulean-Ypet, Cerulean-YFP, CyPet-EYFP, CyPet-Venus, CyPet-YPet, CyPet-Citrine, mTurquoise-Venus, mTurquoise-Ypet, mTurquoise-Citrine, ECFP-EYFP, TagGFP-TagRFP, mTFP1-Citrine, Citrine-mKate2, mTurquoise1-SEYFP, mTurquoise2-SEYFP and clover-mRuby2,
b. protein-organic dye pairs, selected from the group consisting of EGFP-mCherry, SYFP2-mStrawberry, mTFP1-mOrange, Clover-mCherry, GFP-Cy3, YFP-Cy3, ECFP-BHQ-0, EYFP-BHQ-2, EGFP-Cy3 and EGFP-BHQ-1,
c. organic dye-organic-dye pairs, selected from the group consisting of mOrange-mCherry, Alexa488-Alexa555, Alexa488-Cy3, Alexa 568-Alexa633, Cy3-Cy5, Alexa 488-Alexa514, Alexa488-Alexa532, Alexa488-546, Alexa488-610, Alexa647-Alexa 680, Alexa647-Alexa680, Alexa647-Aelxa700, Alexa647-Alexa750, BHQ-1-FAM, BHQ-1-TET, BHQ-1-JOE, BHQ-1-HEX, BHQ-1-Oregon green, BHQ-2-TAMRA, BHQ-2-ROX, BHQ-2-Cy3, BHQ-2-Cy3.5, BHQ-2-CAL Red, BHQ-2-Red 640, BHQ-3-Cy5, or BHQ-3-Cy5.5, Dabcyl-Edans and Dabsyl-Edans, fluorescine.

32. The probes of any of paragraphs 24 to 31, wherein the dsRBD comprises a dsRBD from the ADAR family or the Staufen family.

33. The probes of any of paragraphs 24 to 32, wherein the dsRBD comprises a dsRBD selected from any of the following double stranded RNA binding proteins (dsRBP): protein kinase R (PKR), ADAD2, ADAR1, ADAR2, TRBP2, Stau1, Dicer, X1RBPA, DGCR8, NFAR1, NFAR2, SPNR, RHA, NREBP/SON, TENR, RDE1, Kanadaptin, HYL1 or RNaseIII.

34. The probes of any of paragraphs 24 to 33, wherein the dsRBD is protein kinase R (PKR) or a homologue thereof.

35. The probes of any of paragraphs 24 to 34, wherein the dsRBD comprises SEQ ID NO: 1 or a protein that has at least 80% amino acid sequence identity to SEQ ID NO: 1.

36. The probes of any of paragraphs 24 to 35, wherein the dsRBD comprises an amino acid of the consensus sequence of SEQ ID NO: 28.

37. A polypeptide comprising a double stranded RNA binding domain (dsRBD) labeled with, or fused to a fluorophore donor.

38. The polypeptide of paragraph 37, wherein the polypeptide is a fusion protein comprising a dsRBD fused to a fluorophore donor, wherein the flurophore donor is located at the N-terminal of the dsRBP.

39. The polypeptide of paragraph 37, wherein the polypeptide is a fusion protein comprising a dsRBD fused to a fluorophore donor, wherein the flurophore donor is located at the C-terminal of the dsRBP.

40. The polypeptide of any of paragraphs 37 to 39, wherein the dsRBD comprises a dsRBD from the ADAR family or the Staufen family.

41. The polypeptide of any of paragraphs 37 to 40, wherein the dsRBD comprises a dsRBD selected from any of the following double stranded RNA binding proteins (dsRBP): protein kinase R (PKR), ADAD2, ADAR1, ADAR2, TRBP2, Stau1, Dicer, X1RBPA, DGCR8, NFAR1, NFAR2, SPNR, RHA, NREBP/SON, TENR, RDE1, Kanadaptin, HYL1 or RNaseIII.

42. The polypeptide of any of paragraphs 37 to 41, wherein the dsRBD is protein kinase R (PKR) or a homologue thereof.

43. The polypeptide of any of paragraphs 37 to 42, wherein the dsRBD comprises SEQ ID NO: 1 or a protein that has at least 80% amino acid sequence identity to SEQ ID NO: 1.

44. The polypeptide of any of paragraphs 37 to 43, wherein the dsRBD comprises an amino acid of the consensus sequence of SEQ ID NO: 28.

45. The polypeptide of any of paragraphs 37 to 44, wherein the fluorophore donor is selected from fluorescent proteins and small fluorescent dye molecule, wherein
   (xviii) fluorescent proteins are selected from the group consisting of
      a. blue fluorescent proteins, preferably selected from the group consisting of EBFP, EBFP2, Azurite and imTagBFP,
      b. cyan fluorescent proteins, preferably selected from the group consisting of ECFP, mECFP, Cerulean, mTurquoise, CyPet, AmCyan1, Midori-lshi Cyan, TagCFP and mTFP1 (Teal),
      c. yellow fluorescent proteins, preferably selected from the group consisting of EYFP, Topaz, Venus, mCitrine, YPet, TagYFP, PhiYFP, ZsYellow1 and mBanana,
      d. orange fluorescent proteins, preferably selected from the group consisting of Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer and mTangerine,
      e. red fluorescent proteins, preferably selected from the group consisting of mRuby, mApple, mStrawberry, AsRed2, mRFP1, JRed, mCherry, HcRed1, mRaspberry, dKeima-Tandem, HcRed-Tandem, mPlum and AQ143,
      f. green fluorescent proteins (GFP), selected from the group consisting of EGFP, Emerald, Superfolder GFP, Azami Green, mWasabi, TagGFP, TurboGFP, AcGFP, ZsGreen and T-Sapphire,
   (xix) small fluorescent dye molecules selected from the group consisting of
      a. acridines, selected from: acridine orange or acridine yellow,
      b. cyanines, selected from: Cy2, Cy3, Cy3B, Cy3.5, Cy5, Cy5.5, Cy7,
      c. fluorones, selected from: Fluorescein, Carboxyfluorescein, Dichlorofluorescein, Eosin, Eosin B, Eosin Y or Erythrosine,
      d. oxazines, selected from: Cresyl violet, Nile blue or Nile red,
      e. phenanthridines, selected from: Ethidium bromide, Gelred or Propidium iodide, and
      f. rhodamines, selected from: Rhodamine, Rhodamine 123, Rhodamine 6G, Rhodamine B, Auramine, Sulforhodamine 101, Sulforhodamine B or Texas red,
46. A nucleic acid encoding the polypeptide of any of paragraphs 36 to 46.
47. A vector comprising the nucleic acid of paragraph 46.
48. A living cell or cell line comprising the two probes of paragraph 24.
49. A living cell or cell line comprising the vector of paragraph 47.
50. A kit comprising:
   a. a double stranded RNA binding domain (dsRBD) labeled with, or fused to, at least a first dye and/or a vector comprising a nucleic acid for encoding the same;
   b. at least one second dye; and
   c. reagents for attaching the second dye to a RNA probe.
51. The kit of paragraph 50, wherein the vector is the vector according to paragraph 47.
52. The kit of paragraph 50, wherein the dsRBD labeled with, or fused to, at least a first dye comprises the polypeptide of paragraph 37 to 45.
53. The kit of any of paragraphs 50 or 52, wherein the first dye is a donor dye (also referred to herein as flurophore donor) and the second dye is an acceptor dye (also referred to herein as quencher or dark quencher).
54. The kit of any of paragraphs 50 to 53, wherein the first dye is an acceptor dye and the second dye is a donor dye.
55. The kit of any of paragraphs 50 to 54, wherein the donor dye is a fluorescent donor dye (also referred to herein as flurophore donor) and the acceptor dye is a fluorescent acceptor dye (also referred to herein as flurophore acceptor, quencher or dark quencher).
56. The kit of any of paragraphs 50 to 55, wherein the fluorophore donor is selected from fluorescent proteins and small fluorescent dye molecule, wherein
   (xx) fluorescent proteins are selected from the group consisting of
      a. blue fluorescent proteins, preferably selected from the group consisting of EBFP, EBFP2, Azurite and imTagBFP,
      b. cyan fluorescent proteins, preferably selected from the group consisting of ECFP, mECFP, Cerulean, mTurquoise, CyPet, AmCyan1, Midori-lshi Cyan, TagCFP and mTFP1 (Teal),
      c. yellow fluorescent proteins, preferably selected from the group consisting of EYFP, Topaz, Venus, mCitrine, YPet, TagYFP, PhiYFP, ZsYellow1 and mBanana,
      d. orange fluorescent proteins, preferably selected from the group consisting of Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer and mTangerine,
      e. red fluorescent proteins, preferably selected from the group consisting of mRuby, mApple, mStrawberry, AsRed2, mRFP1, JRed, mCherry, HcRed1, mRaspberry, dKeima-Tandem, HcRed-Tandem, mPlum and AQ143,
      f. green fluorescent proteins (GFP), selected from the group consisting of EGFP, Emerald, Superfolder GFP, Azami Green, mWasabi, TagGFP, TurboGFP, AcGFP, ZsGreen and T-Sapphire,
   (xxi) small fluorescent dye molecules selected from the group consisting of
      a. acridines, selected from: acridine orange or acridine yellow,
      b. cyanines, selected from: Cy2, Cy3, Cy3B, Cy3.5, Cy5, Cy5.5, Cy7,
      c. fluorones, selected from: Fluorescein, Carboxyfluorescein, Dichlorofluorescein, Eosin, Eosin B, Eosin Y or Erythrosine,
      d. oxazines, selected from: Cresyl violet, Nile blue or Nile red,
      e. phenanthridines, selected from: Ethidium bromide, Gelred or Propidium iodide, and
      f. rhodamines, selected from: Rhodamine, Rhodamine 123, Rhodamine 6G, Rhodamine B, Auramine, Sulforhodamine 101, Sulforhodamine B or Texas red,
57. The kit of any of paragraphs 50 to 56, wherein the fluorophore acceptor is selected from the group consisting of (i) acridines, selected from acridine orange or acridine yellow,
(ii) cyanines, selected from Cy2, Cy3, Cy3B, Cy3.5, Cy5, Cy5.5 or Cy7,
(xxii) fluorones, selected from Fluorescein, Carboxyfluorescein, Dichlorofluorescein, Eosin, Eosin B, Eosin Y or Erythrosine,
(xxiii) oxazines, preferably Cresyl violet, Nile blue or Nile red,
(xxiv) phenanthridines, preferably ethidium bromide, Gelred or propidium iodide, and
(xxv) rhodamines, preferably Rhodamine, Rhodamine 123, Rhodamine 6G,
(xxvi) Rhodamine B, Auramine, Sulforhodamine 101, Sulforhodamine B or Texas red, preferably cyanines (ii), more preferably Cy3.

58. The kit of any of paragraphs 50 to 57, wherein the dark quencher selected from the group consisting of Dabcyl, Dabsyl, Black Hole Quencher (BHQ™) dyes, preferably BHQ-0, BHQ-1, BHQ-2 or BHQ-3, QXL quenchers, preferably QXL 490, QXL 570, QXL 610, QXL 670, or QXL 680, Iowa Black quenchers, preferably Iowa black FQ or Iowa Black RQ, and IRDyes, preferably IRDye 800, IRDye 800CW, IRDye 800RS, IRDye 680, IRDye 680LT, IRDye 700, or IRDye 700DX, more preferably Black Hole Quencher (BHQ™) dyes, most preferably BHQ-1.

59. The kit of any of paragraphs 50 to 58, wherein the spectrally paired fluorophore donor and fluorophore acceptor, or the spectrally paired fluorophore donor and dark quencher are selected from the group consisting of:
a. protein-protein pairs, selected from the group consisting of ECFP-Citrine, ECFP-Venus, Cerulean-Citrine, Cerulean-Venus, Cerulean-Ypet, Cerulean-YFP, CyPet-EYFP, CyPet-Venus, CyPet-YPet, CyPet-Citrine, mTurquoise-Venus, mTurquoise-Ypet, mTurquoise-Citrine, ECFP-EYFP, TagGFP-TagRFP, mTFP1-Citrine, Citrine-mKate2, mTurquoise1-SEYFP, mTurquoise2-SEYFP and clover-mRuby2,
b. protein-organic dye pairs, selected from the group consisting of EGFP-mCherry, SYFP2-mStrawberry, mTFP1-mOrange, Clover-mCherry, GFP-Cy3, YFP-Cy3, ECFP-BHQ-0, EYFP-BHQ-2, EGFP-Cy3 and EGFP-BHQ-1,
c. organic dye-organic-dye pairs, selected from the group consisting of mOrange-mCherry, Alexa488-Alexa555, Alexa488-Cy3, Alexa 568-Alexa633, Cy3-Cy5, Alexa 488-Alexa514, Alexa488-Alexa532, Alexa488-546, Alexa488-610, Alexa647-Alexa 680, Alexa647-Alexa680, Alexa647-Aelxa700, Alexa647-Alexa750, BHQ-1-FAM, BHQ-1-TET, BHQ-1-JOE, BHQ-1-HEX, BHQ-1-Oregon green, BHQ-2-TAMRA, BHQ-2-ROX, BHQ-2-Cy3, BHQ-2-Cy3.5, BHQ-2-CAL Red, BHQ-2-Red 640, BHQ-3-Cy5, or BHQ-3-Cy5.5, Dabcyl-Edans and Dabsyl-Edans, fluorescine.

EXAMPLES

Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the paragraphs to the invention, but are rather intended to be exemplary of certain embodiments. Any variations in the exemplified methods which occur to the skilled artisan are intended to fall within the scope of the present invention.

Pluripotent stem cells (PSC) offer a powerful approach to model human heart disease in vitro and to develop assays for drug discovery and development. Nonetheless, the cellular heterogeneity and relatively immature phenotype of PSC-derived cardiac myocytes (CMs) have limited the widespread use of this promising cell source. While recent technical advances have facilitated live-cell mRNA imaging by detecting specific gene transcripts in living cells, major drawbacks such as multiple binding sites, complexity of probe design, low multiplexing potential and low sensitivity have prevented their widespread use. In order to overcome these limitations, we have developed a novel technology for the multiplex analysis of gene expression in individual living cells (MAGIC) to perform live-cell imaging of gene expression and simultaneous functional analyses of single CMs. Here, the inventors have engineered a genetically and chemically modified fluorescent dsRNA-binding domain (e,g., a dsRBD) and combined it with chemically modified fluorescent antisense RNA probes (also referred to as RNA-binding probes) to selectively visualize specific mRNA transcripts in single living cells.

In particular, the inventors demonstrate herein the feasibility of the system for live-single cell imaging and analyses and demonstrate that the method can be used to specifically detect hybridized probes. Demonstrated herein, in an exemplary method, is a live-cell mRNA imaging technology allowing the functional characterization of single human PSC-CMs expressing myosin light chain 2v and myosin heavy chain α (MHCα) as markers for the ventricular cell fate and myocardial maturity, respectively. In conclusion, the inventors herein have developed a method and system for the multiplex analysis of gene expression in individual living cells (MAGIC). This method can be used to phenotypically characterize, track and study living cells with distinct genetic profile. By tailoring the single cell live fluorescence gene expression imaging with functional assays, the methods, systems and kits disclosed herein are useful in methods for enhancing our understanding of cardiac and cardiomyocyte biology, heart disease and cardiovascular function on a living cell basis, and can be applied to any biological system where cellular heterogeneity plays an important biological role, such as cancer pathobiology.

Example 1

In vitro cellular modeling of heritable human heart disease has been greatly facilitated by iPSC technology[1-3]. Nonetheless, the cellular heterogeneity and relatively immature phenotype of iPSC-CMs has limited the wide spread use of this promising cell source for human disease modeling[4-7]. In order to overcome these limitations, the inventors developed a method and technology for live-cell imaging of gene expression and simultaneous functional analysis of single cells. Most commonly, gene expression assays in living cells rely on the detection of fluorescently labeled proteins under the transcriptional control of the gene of interest. Accordingly, these approaches have entailed the generation of transgenic animals[8,9] or embryonic stem cell lines[10,11] to isolate and study discrete subsets of cells with specific gene expression profiles. However, these methods are cumbersome, time consuming, and expensive and therefore allow for only a limited number of genes to be examined at a time.

Recent technical advances have facilitated live-cell mRNA imaging by detecting gene transcripts via nucleic acid[12,13] or protein probes[14,15]. However, several drawbacks of these existing techniques such as genetic encoding of target mRNA and reporter protein, the necessity to target multiple binding sites, complexity of probe design, low multiplexing potential and low sensitivity[16,17,] however, have prevented their widespread use.

Accordingly, an important advantage and strength to the methods and technology described herein is the development of a method for the real-time detection of multiple different specific transcripts at the same time, in single living cells. Importantly, the methods, compositions and technology described herein can be tailored, such that single cell live fluorescence gene expression imaging and functional assays can be performed in any living cell, and can be adapted for use with cells from in vivo and in vitro disease models, and can be used to greatly enhance the understanding of disease biology, for example, cardiomyocyte biology and heart disease.

Example 2

Described herein is a Förster Resonance Energy Transfer (FRET)-based technology for the multiplex analysis of gene expression in individual living cells (MAGIC). The methodology utilizes gene-specific fluorescently labeled RNA-binding probe (RBP) such as, e.g., a gene-specific antisense RNA (also referred to herein as a "MAGIC probe"), and a duplex-binding protein (also referred to herein as a "MAGIC factor") for example, a duplex-binding protein consisting of the double-stranded (dsRNA)-binding domain (dsRBD) of human protein kinase R (PKR) protein. In this exemplary embodiment, the dsRBD of PKR consists of 169 amino acids[18] and has been shown to be sufficient to bind dsRNA selectively over ssRNA in a sequence-independent manner[19,20]. The protein production, purification and fluorescent labeling strategy is shown in FIG. 1A. The inventorsd cloned cDNA containing the dsRBD coding site of human PKR into pET-14b recombinant expression vector and recombinantly expressed the dsRBD including a polyhistidine-tag at its N-terminus in E. coli. The purified protein was obtained via cobalt immobilized metal chelate affinity beads and subsequently fluorescently labeled it with Alexa Fluor 488. Chemical attachment of Alexa Fluor 488 was achieved via conjugation to thiol and carboxylic acid groups of the protein, however, there was not significant labeling of the protein with these methods (data not shown).

Figure 2:
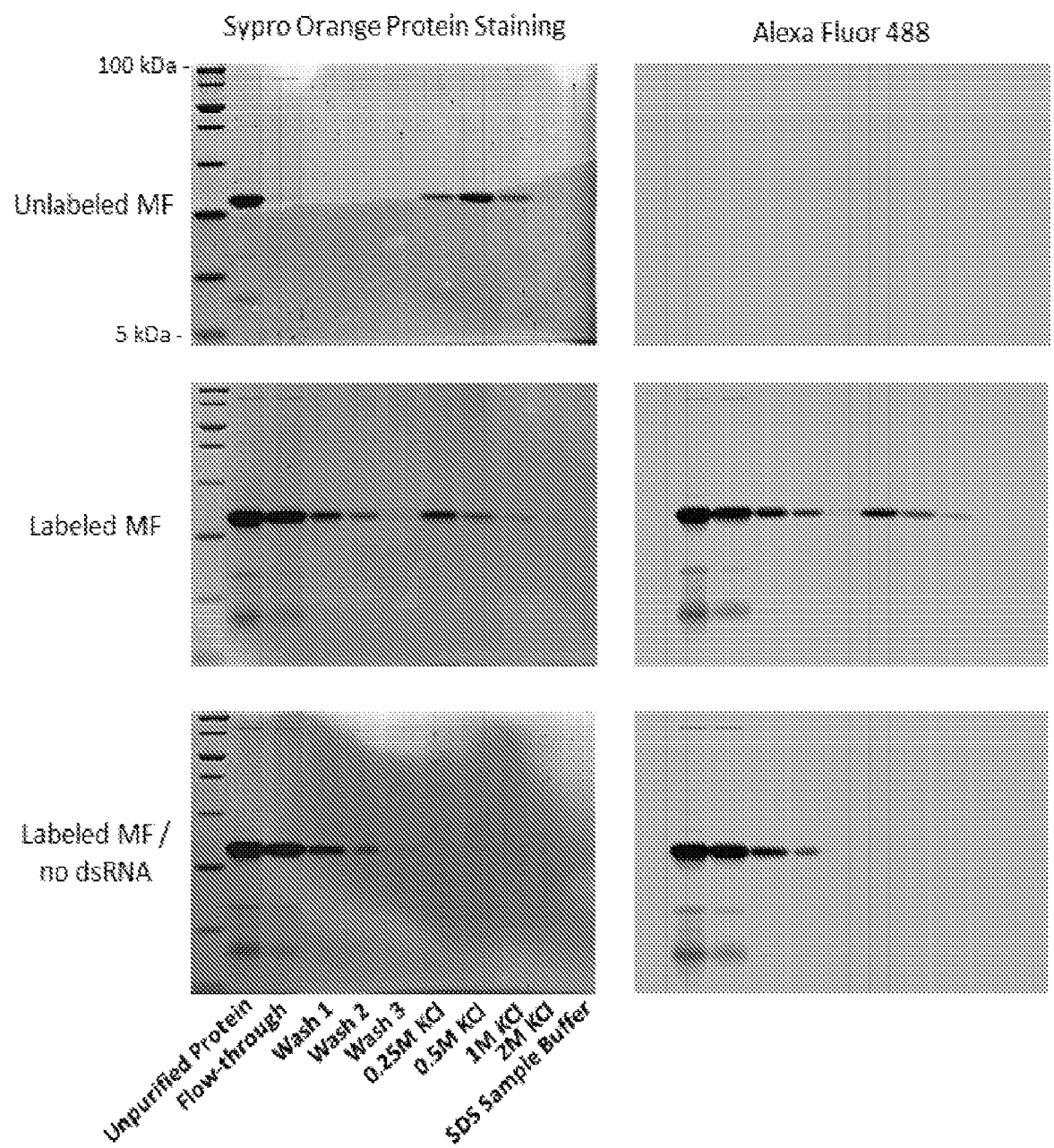
FIG. 2 shows affinity Purification of dsRBD MAGIC Factor. Unlabeled and fluorescently-labeled MAGIC factor (MF) was affinity purified using dsRNA-coupled agarose beads. The proteins were reacted with the beads for 1 h, washed three times with binding buffer and then gradually eluted with increasing concentrations of KCl. At the end, remaining proteins were eluted with 1×SDS-PAGE sample buffer and all samples run on a 12% SDS-PAGE gel. As a control experiment, fluorescently-labeled MAGIC factor was reacted with agarose beads in the absence of dsRNA.
Figure 3A:
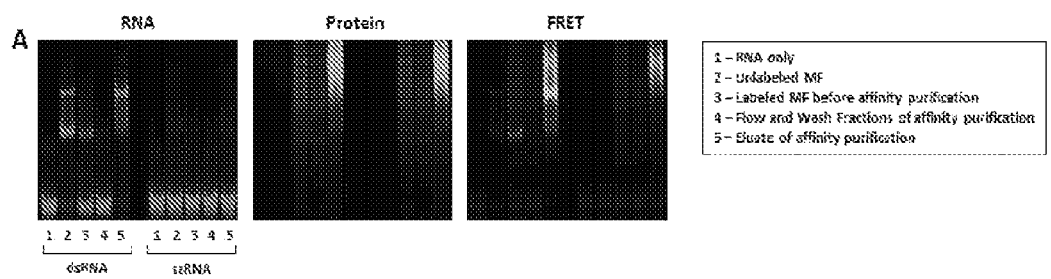
FIG. 3A-3B shows the Affinity Purification of the dsRBD Restores Binding Affinity of Fluorescent MAGIC Factor. MAGIC factor was fluorescently-labeled with Alexa Fluor 488 and then reacted with dsRNA-coupled agarose beads to separate binding, functional protein (eluate) from non-binding, non-functional protein (flow and wash fractions).
Figure 3B:
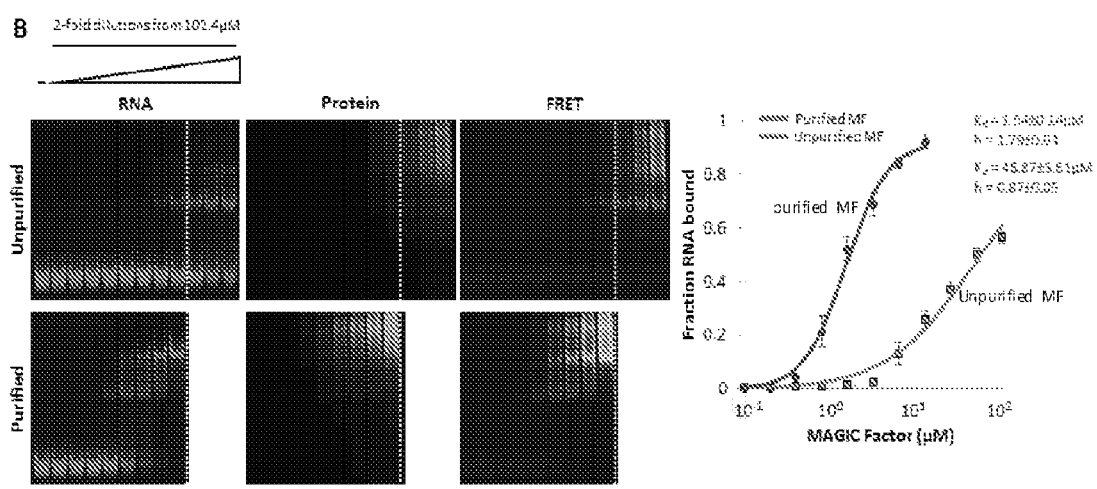

Alternatively, the duplex-binding protein (e.g., dsRBD) or MAGIC factor was labeled with a Alexa Fluor 488 targeting primary amino groups of protein. However, as demonstrated in FIG. 2, the chemical modification of MAGIC factor at its amino groups largely results in the loss of its ability to bind dsRNA, as opposed to unlabeled MAGIC factor that is capable of binding dsRNA entirely. Quantification of protein concentration in the individual fraction showed that only 4% of MAGIC factor is able to bind dsRNA after fluorescent labeling. Therefore affinity purification of the fluorescently-labeled MAGIC factor was performed against dsRNA using agarose beads that were linked to dsRNA molecules. As a result, the inventors were able to entirely restore its binding affinity and/or isolate only dsRBD that retained the dsRNA binding affinity. The inventors then further quantified the binding affinity of unpurified and affinity purified, labeled MAGIC factor and found that affinity purification results in a ~30-fold increase in binding affinity, as shown using the corresponding Kd-values (FIG. 3). Taken together, the inventors were able to genetically and chemically engineer a fluorescently-labeled protein comprising a dsRNA-binding domain that binds specifically to dsRNA.

Figure 4A:
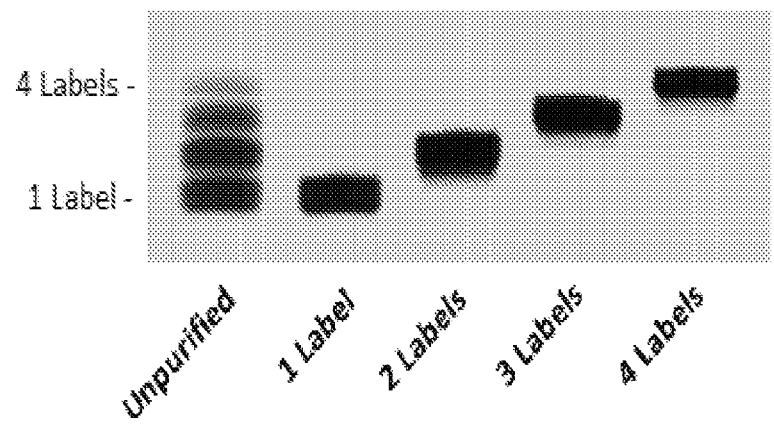
FIG. 4A-4B shows the effect of the Degree of Fluorescent Labeling on the Fluorescence Intensity of RNA-binding Probes.
Figure 4B:
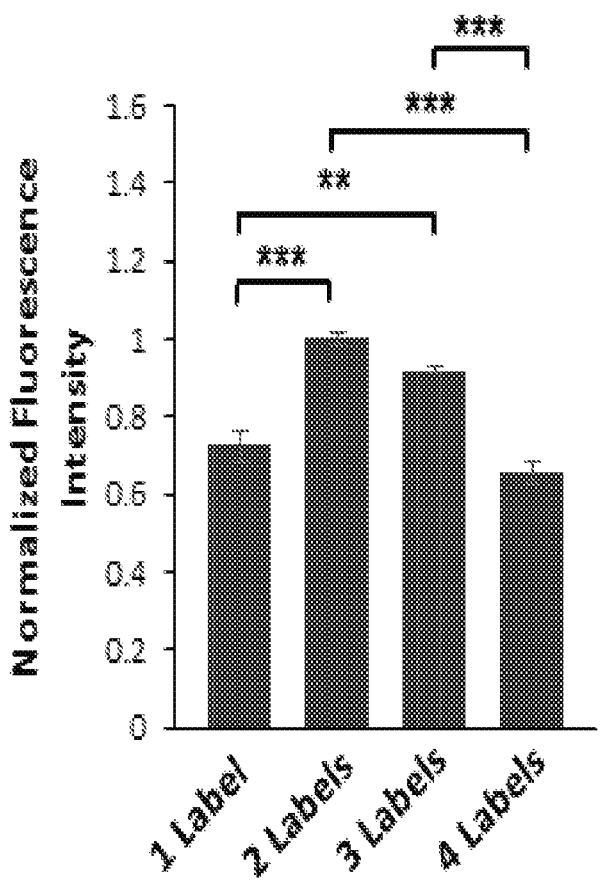
Figure 5A:
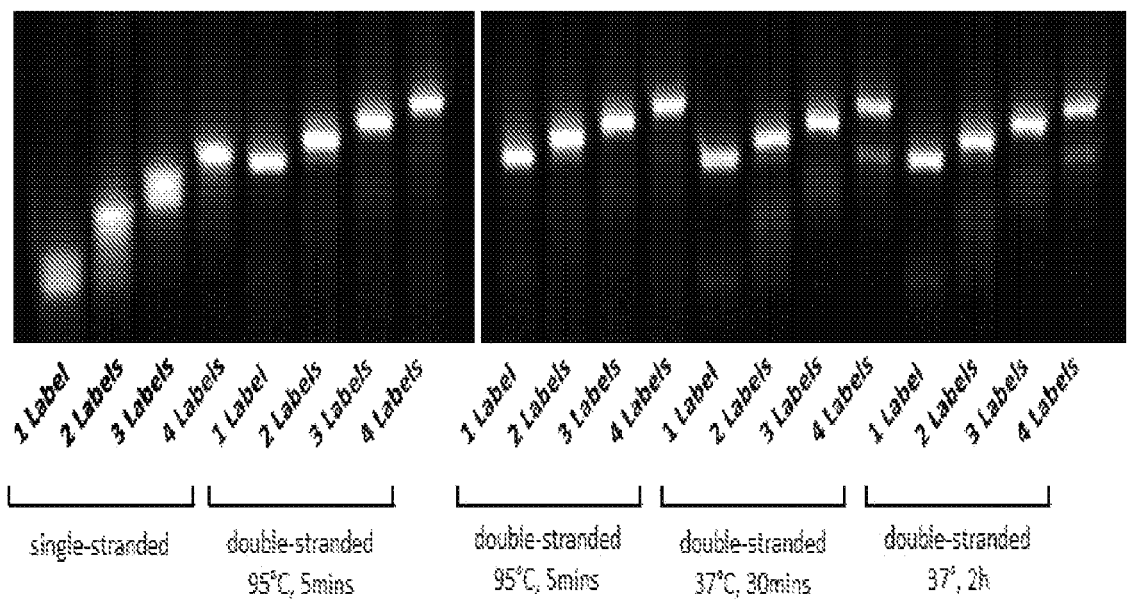
FIG. 5A-5B shows the effect of the Degree of Fluorescent Labeling on the Hybridization Kinetics of RNA Probes.
Figure 5B:
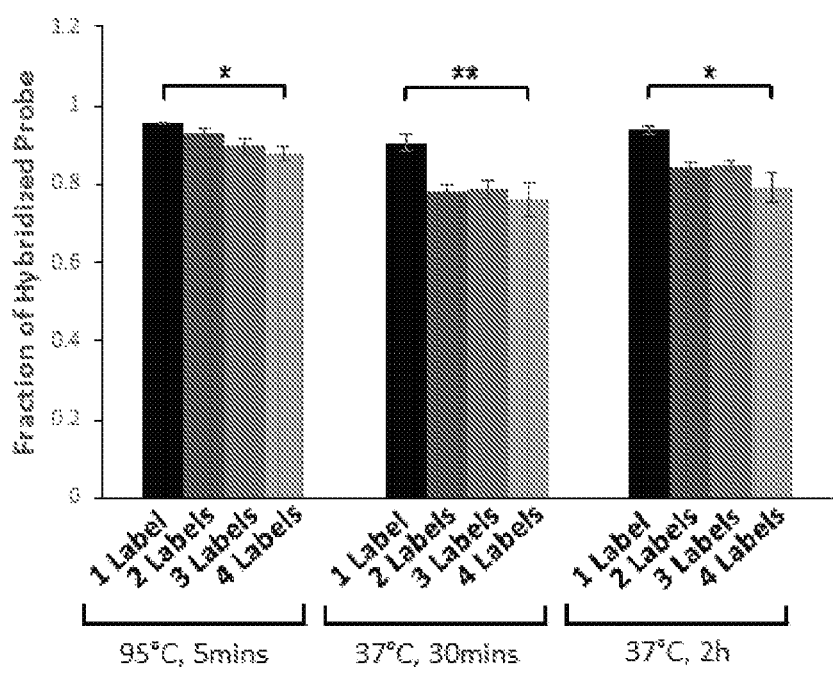
Figure 6A:
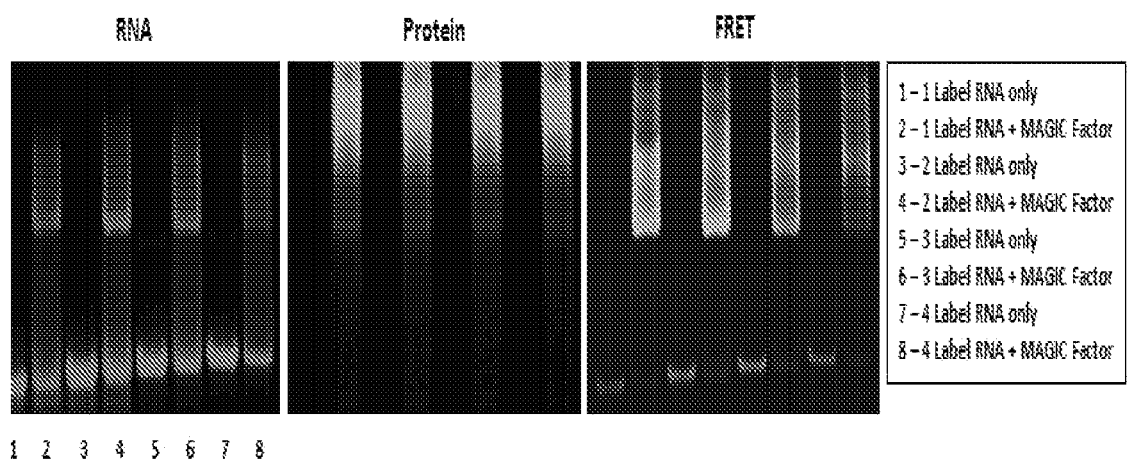
FIG. 6A-6B shows the effect of the Degree of Fluorescent Labeling of RNA Probes on the Binding of MAGIC Factor and FRET Intensity.
Figure 6B:
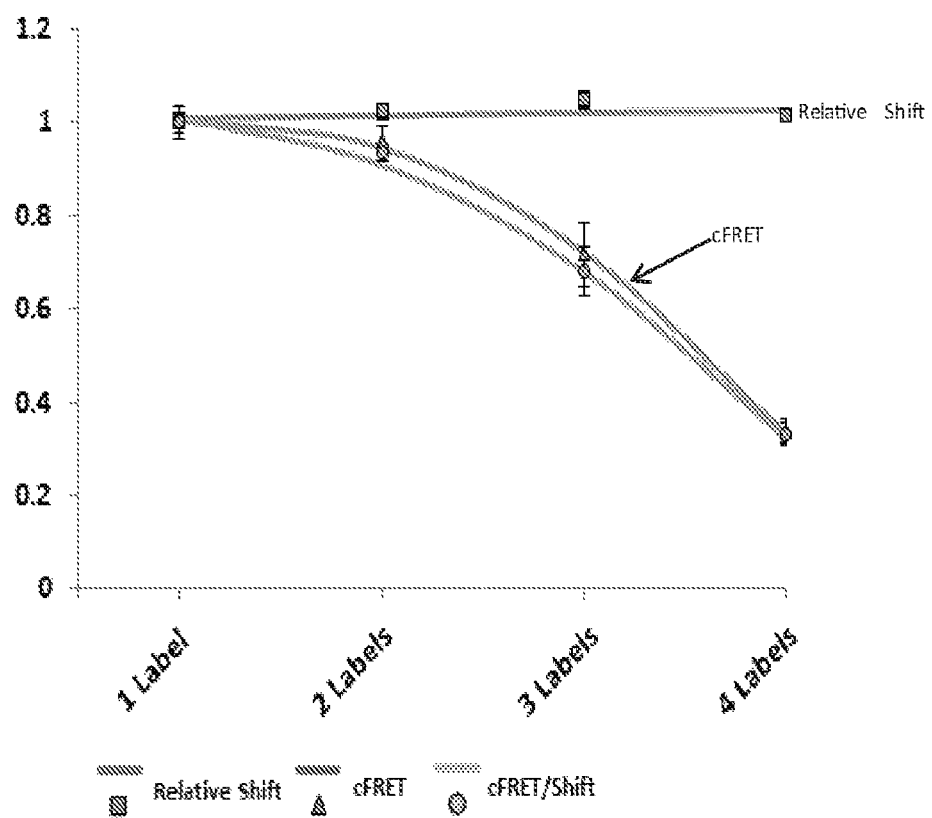

As disclosed herein, the technology utilizes gene-specific, fluorescently-labeled RNA binding probes (RBP) (also referred to in the Examples section as MAGIC probes). Production, purification and fluorescent labeling of the RNA binding probes is shown in FIG. 1B. As exemplary examples, the RNA-binding probes used in the experiments comprise a 20-mer RNA generated through standard in vitro transcription using T7 phage polymerase, although different mer ranges of 6-45 or 50 or more are encompassed for use in the methods and compositions as disclosed herein. An amino-reactive fluorescent dye was used that replaced uridine bases with aminoallyl-modified uridine bases during in vitro transcription. The RNA probes where then fluorescently-labeled by chemically attaching Alexa Fluor 647 to the amino groups on the uridine bases. However, because the chemical modification of RNA bears the potential to alter its fluorescence and hybridization kinetics and consequently the FRET signal between the RBP (e.g. MAGIC probe) and labelled dsRBD (e.g., MAGIC factor), the inventors evaluated the effects of the number of fluorescent dyes on each 20-mer RNA molecule. The RNA was fluorescently-labeled and purified one-, two-, three- and four-labeled RNA's were collected and isolated from a denaturing polyacrylamide gel. The inventors discovered a marked difference in the resulting fluorescence intensity between the differently labeled RNA probes (FIG. 4). When the inventors hybridized the fluorescent RNA binding probe to its complementary RNA at 37° C., it was discovered that only the four-labeled RNA exhibited altered hybridization kinetics, however, there was no difference in the other three RNA binding probe molecules (FIG. 5). The inventors then investigated whether the number of fluorescent dyes might affect the binding ability of fluorescently labeled dsRBD (i.e., the MAGIC factor) and determined that there was no difference among the four different RNA binding probes (FIG. 6). However, the inventors discovered that the stronger labeled the RNA binding probe, the less the resulting FRET between MAGIC factor and the RNA binding probe became, indicating that fluorescence quenching at the stronger labeled RNA binding probe. Based on these results, the inventors determined that one- and two-labeled MAGIC RNA binding probe probes are optimal for in vitro live-cell experiments in order to maximize the resulting FRET signal.

Example 3

Figure 7D:
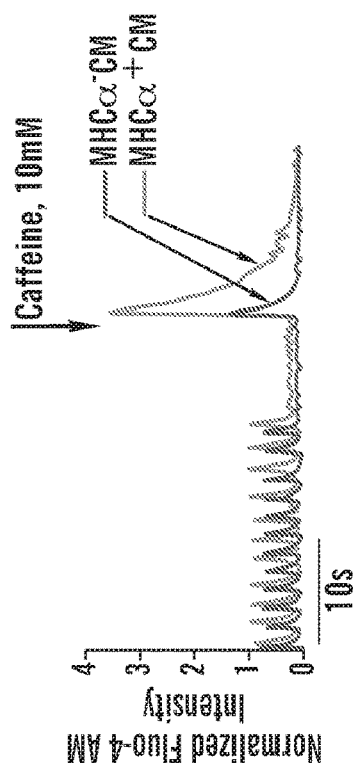
Figure 7E:
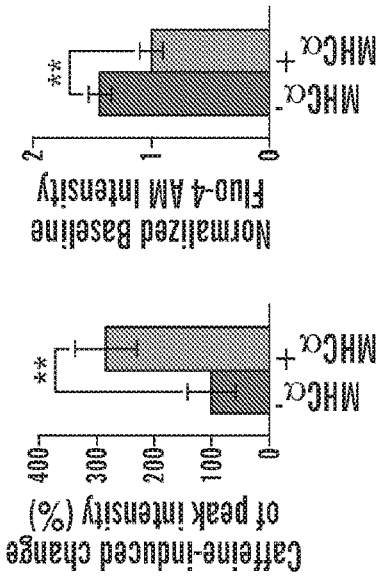
Figure 7F:
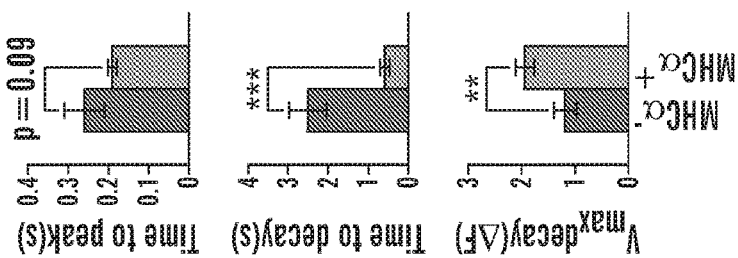
Figure 7G:
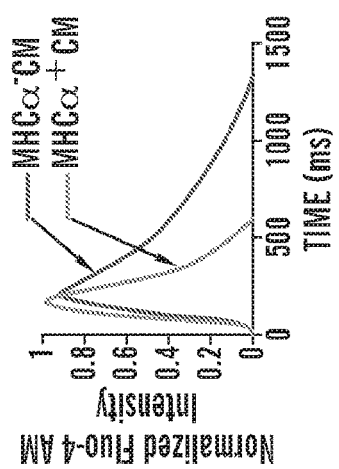
Figures 8A, 8B:
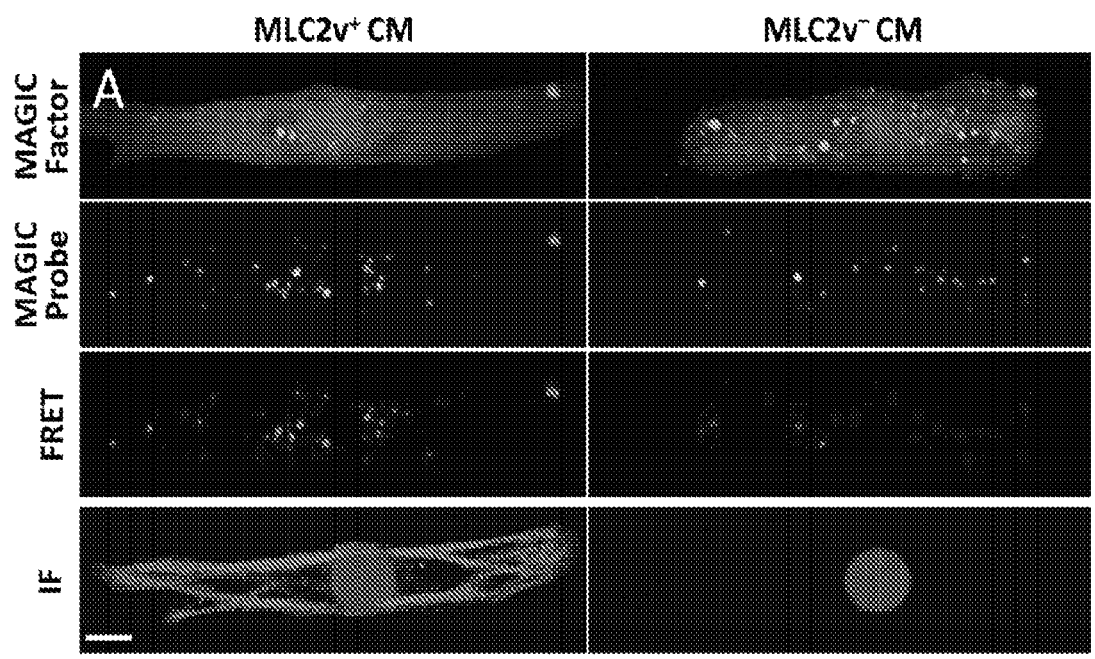
FIG. 8A-8B shows real-time Identification of Human Ventricular CMs Using the MAGIC technology.
Figure 9A:
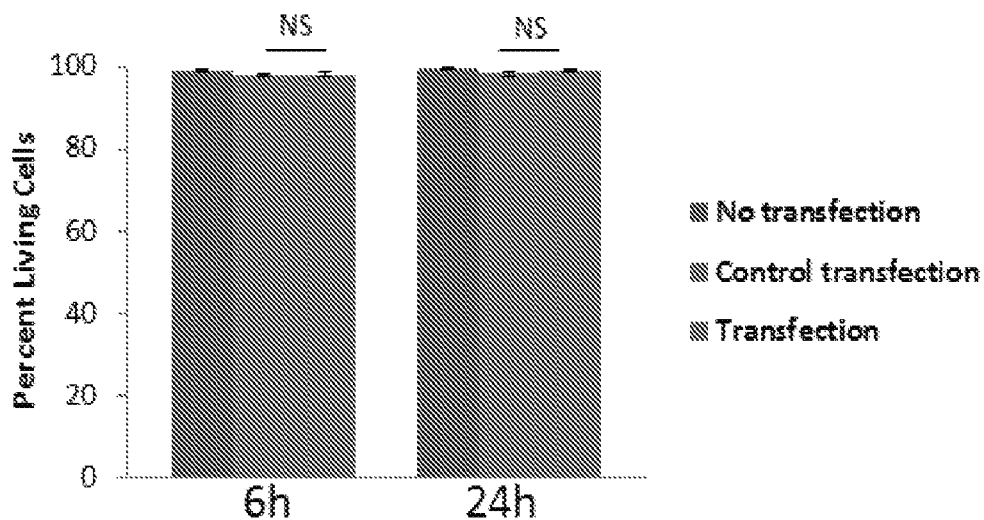
FIG. 9A-9B show Cell Viability After Transfection.
Figure 9B:
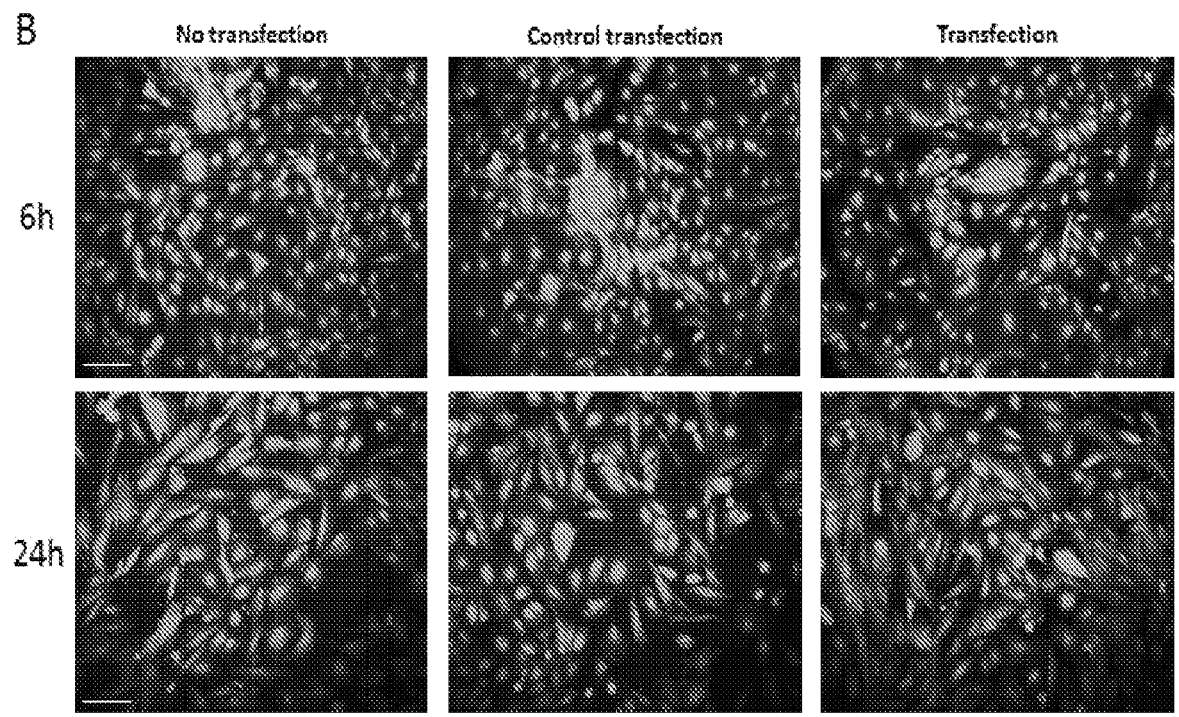
Figure 10A:
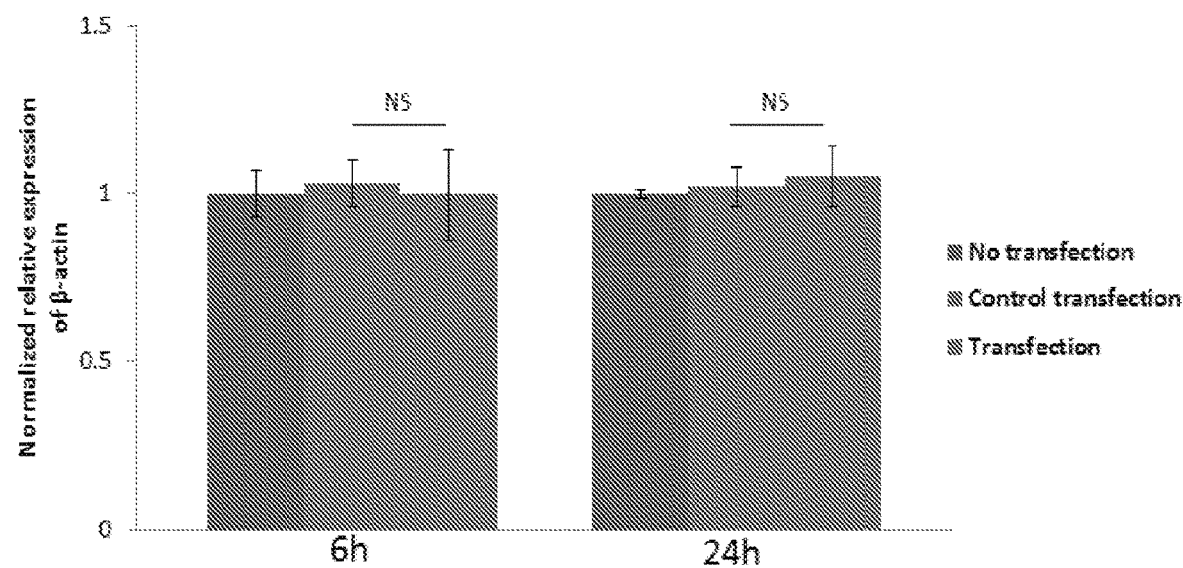
FIG. 10A-10B show relative mRNA and Protein Expression of β-actin After Transfection. hESC-CMs were either not transfected, exposed to the transfection reagents only or delivered with unlabeled MAGIC factor and unlabeled MAGIC probe against the human β-actin mRNA.
Figure 10B:
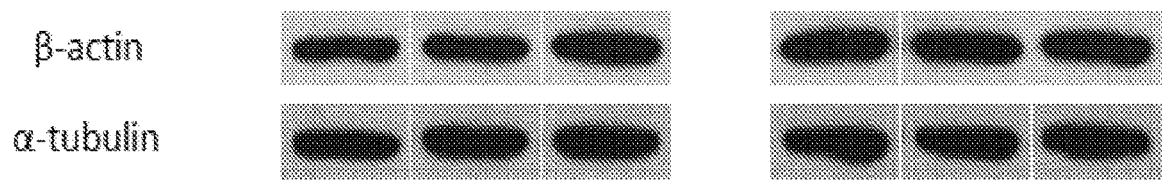

Upon delivery into living cells, MAGIC RNA-binding probes hybridize to native mRNA. In the exemplary example, this dsRNA duplex is recognized by the labeled dsRBD MAGIC factor to generate a FRET pair and allows for the selective detection of bound probes. Unbound RNA-binding probes do not create a FRET pair and are readily distinguished from the RNA-RNA hybrid (schematic shown in FIG. 7A). The inventors demonstrate herein, as an exemplary example, the application of the technology in live-cell mRNA imaging system for the functional analysis of different subsets of CMs. Prior work from a number of laboratories demonstrates that myosin heavy chain a (MHCα) expression increases with the functional and structural maturation of PSC-CMs[21,22], suggesting a key role for proper development of cardiac contractile function. Herein, the inventors targeted the MHCα mRNA as a gene of interest in a pure human embryonic stem cell-derived CM population and demonstrated a high degree of specificity and sensitivity of MAGIC RNA-binding probe (FIGS. 7B & 7C). $Ca^{2+}$ imaging of MHCα+ and MHCα- CMs demonstrated that MHCα+ CMs possess more mature spontaneous $Ca^{2+}$ handling properties (FIGS. 7D & E) as well as in response to caffeine (FIGS. 7F & 7G). The inventors further selectively identify ventricular CMs using a specific MAGIC probe against the human myosin light chain 2v (MLC2v) mRNA (FIG. 8A) with again a high degree of specificity and sensitivity of our technology (FIG. 8B). Collectively, the technology and methods was determined to able to analyze the cellular physiology of individual live cells specific subtypes of stem cell-derived CMs. Furthermore, the addition of the dye-labelled RNA-binding protein (RBP) or the dye-labelled duplex-binding protein (e.g., dsRBD) approach did not alter cell viability, mRNA expression, or protein levels (FIGS. 9 AND 10).

Example 4

Figure 11A:
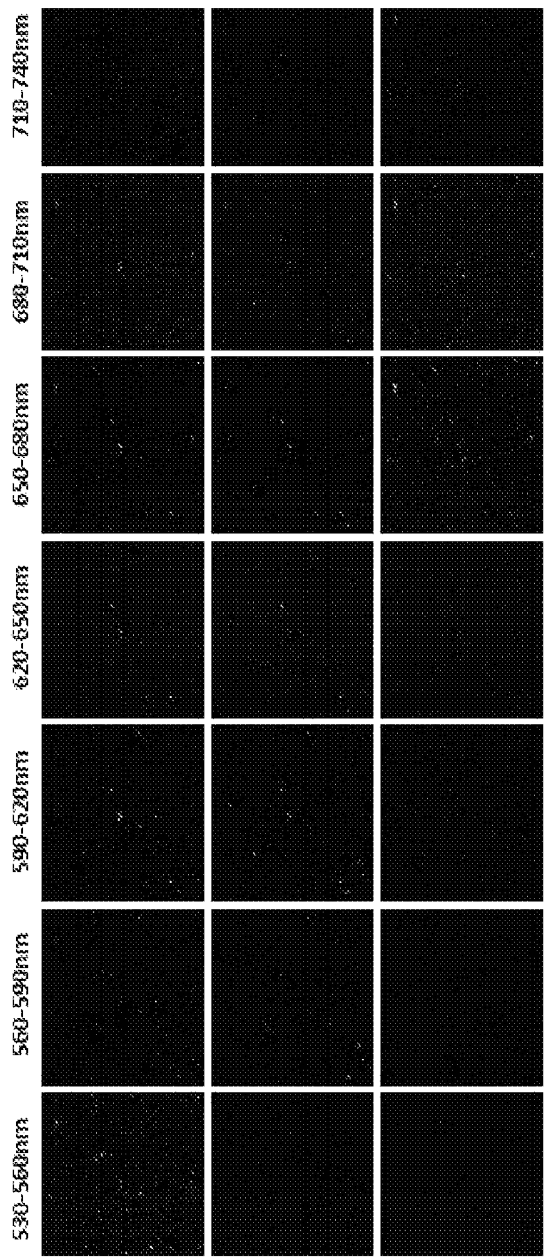
FIG. 11A-11B show Multiplex Imaging of Three FRET Pairs. Three FRET pairs (Alexa Fluor 488-546, 488-594 and 488-647) and the corresponding single labeled constructs (Alexa Fluor 488, 546, 594 and 647) were packed in individual lipocomplexes such that every lipocomplex contains only one type of fluorescent construct.
Figure 11B:
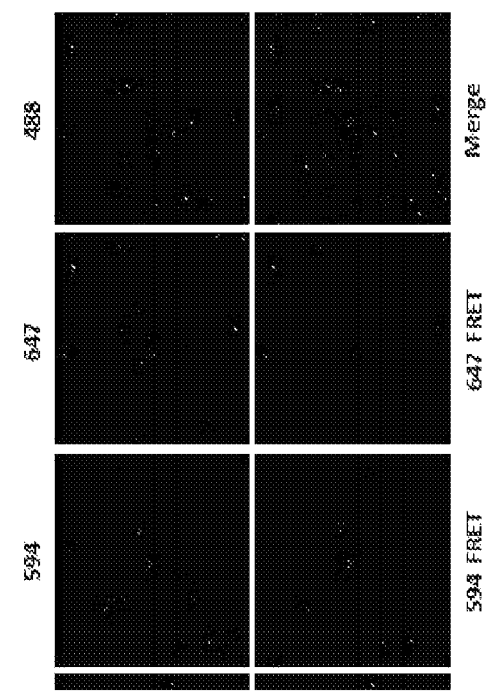
Figure 12:
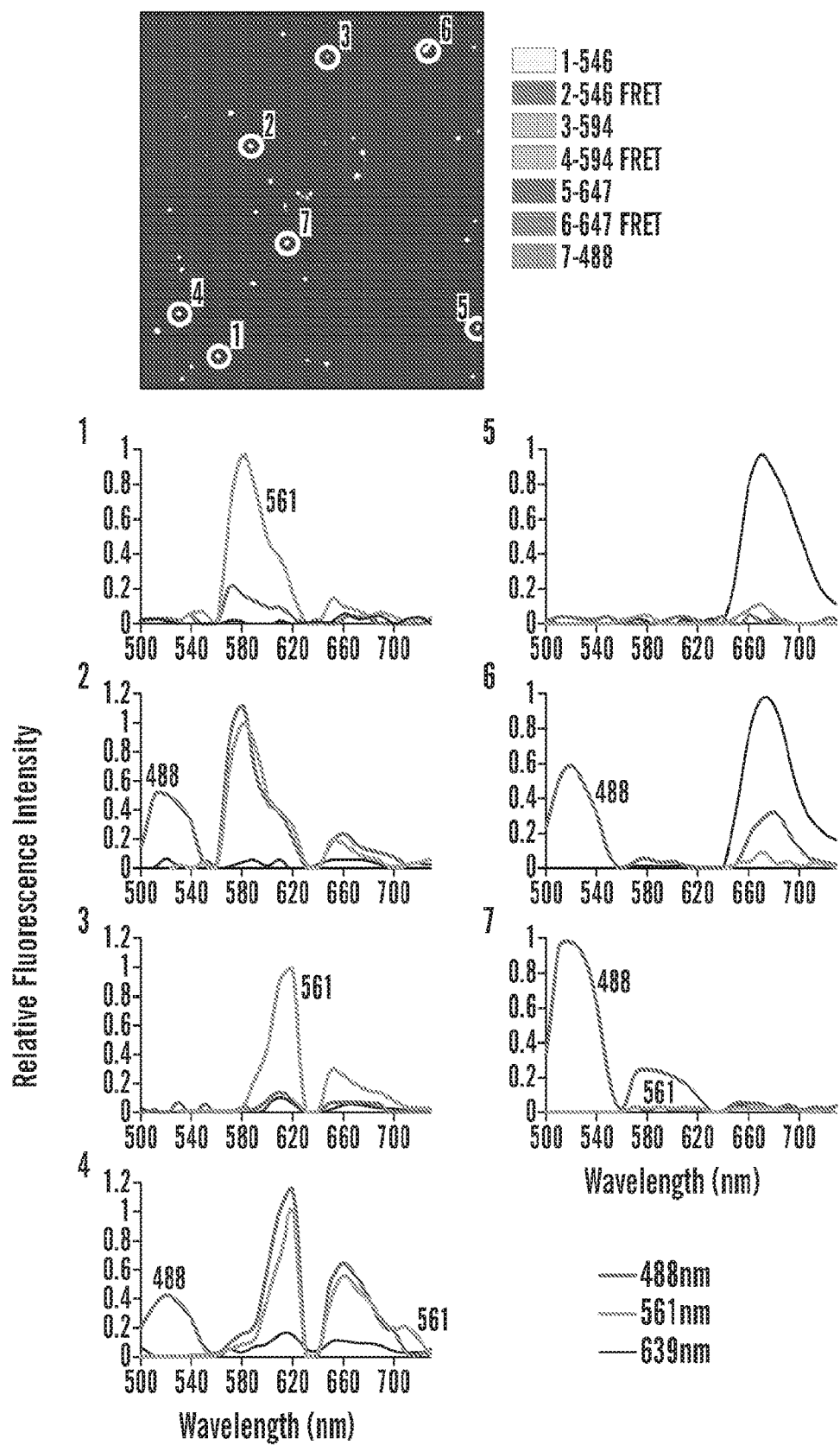
FIG. 12 shows the validation of Multiplex Imaging of Three FRET Pairs. The fluorescent constructs on the merge image from FIG. 11 were identified and plotted the spectral profile of that lipocomplex from spectral imaging data from FIG. 11.

The technology, methods and compositions as disclosed herein can be adapted easily for multiplexing, e.g., multiplex gene expression analysis. Previous, similar methodologies have been limited by their lack multiplexicity. Therefore, the inventors demonstrated the ability of the technology disclosed herein to perform multiplexed imaging of three RNA-binding FRET probes (FIGS. 11 AND 12). The inventors imaged the FRET pairs Alexa Fluor 488-546, 488-594 and 488-647 along with the single labeled constructs Alexa Fluor 488, 546, 594 and 647 altogether by spectral imaging using a laser scanning confocal microscope. The inventors successfully demonstrated that distinct fluorescence images could be detected of the individual constructs after applying linear unmixing and independent component analysis, further demonstrating that the technology herein is useful and a major innovation in multiplex live-cell RNA imaging.

In conclusion, the inventors herein have developed a technology that enables the analysis of multiple specific mRNA in single living cells via a fluorescent hybrid approach comprising a RNA-nucleic acid probe and duplex-binding protein, e.g., a dsRNA-binding protein. In the Examples, the approach utilizes FRET as a tool to discern hybridized probes within living cells. Accordingly, the inventors provided evidence that the methodology allows for the specific visualization of multiple gene transcripts in a single cell and also demonstrates that subpopulations of cells with distinct gene expression profile can be tracked, an/or isolated using FACS, as well as their function simultaneously assessed in real-time. Accordingly, the methods, compositions and kits as disclosed herein can be used for cell tracking and is useful for any application that include heterogeneous cell types or where cellular heterogeneity plays an important biological role. In cancer research, for example, tumor heterogeneity has affected the study of cancer pathobiology and effects of drug treatment[23]. Using the MAGIC technology disclosed herein, cancer cells and cancer stem cells with a specific genetic profile could now be studied with respect to their pathophysiology and how they respond to specific drugs. Also, the technology disclosed herein is advantageous in that no genetic manipulations are required, therefore making this methodology suitable for a wide variety of cell types and in vivo applications including high throughput applications.

Additionally, the technology described herein can be used to track the expression and intracellular movement of other RNA types, including but not limited to, long non-coding RNA or microRNA, could potentially also be tracked in real-time in individual living cells, since the detection of specific target RNA relies on hybridization of a RNA binding probe (RBP) and the duplex detected with a duplex binding protein, as disclosed herein. Lastly, unlike the increasingly more complex and expensive probes[24] used for gene expression analysis, the present technology is simple in that it relies unmodified RNA-binding probes, in that they are only labeled with one or two fluorphores, therefore returning to simple RNA-binding probes that can be specific to the RNA of gene of interest are cost-effective.

REFERENCES

The references are incorporated herein in their entirety by reference.
1. Lan, F., et al. Abnormal calcium handling properties underlie familial hypertrophic cardiomyopathy pathology in patient-specific induced pluripotent stem cells. *Cell stem cell* 12, 101-113 (2013).
2. Sun, N., et al. Patient-specific induced pluripotent stem cells as a model for familial dilated cardiomyopathy. *Science translational medicine* 4, 130ra147 (2012).
3. Wang, G., et al. Modeling the mitochondrial cardiomyopathy of Barth syndrome with induced pluripotent stem cell and heart-on-chip technologies. *Nature medicine* 20, 616-623 (2014).
4. Moretti, A., Laugwitz, K. L., Dorn, T., Sinnecker, D. & Mummery, C. Pluripotent stem cell models of human heart disease. *Cold Spring Harbor perspectives in medicine* 3 (2013).
5. Sallam, K., Kodo, K. & Wu, J. C. Modeling inherited cardiac disorders. *Circulation journal: official journal of the Japanese Circulation Society* 78, 784-794 (2014).
6. Zhu, W. Z., et al. Neuregulin/ErbB signaling regulates cardiac subtype specification in differentiating human embryonic stem cells. *Circulation research* 107, 776-786 (2010).
7. Zhang, Q., et al. Direct differentiation of atrial and ventricular myocytes from human embryonic stem cells by alternating retinoid signals. *Cell research* 21, 579-587 (2011).
8. Domian, I. J., et al. Generation of functional ventricular heart muscle from mouse ventricular progenitor cells. *Science* 326, 426-429 (2009).
9. Wu, S. M., et al. Developmental origin of a bipotential myocardial and smooth muscle cell precursor in the mammalian heart. *Cell* 127, 1137-1150 (2006).
10. Elliott, D. A., et al. NKX2-5(eGFP/w) hESCs for isolation of human cardiac progenitors and cardiomyocytes. *Nature methods* 8, 1037-1040 (2011).
11. Klug, M. G., Soonpaa, M. H., Koh, G. Y. & Field, L. J. Genetically selected cardiomyocytes from differentiating embronic stem cells form stable intracardiac grafts. *The Journal of clinical investigation* 98, 216-224 (1996).
12. Santangelo, P. J., et al. Single molecule-sensitive probes for imaging RNA in live cells. *Nature methods* 6, 347-349 (2009).
13. Tyagi, S. & Kramer, F. R. Molecular beacons: probes that fluoresce upon hybridization. *Nature biotechnology* 14, 303-308 (1996).
14. Bertrand, E., et al. Localization of ASH1 mRNA particles in living yeast. *Molecular cell* 2, 437-445 (1998).
15. Ozawa, T., Natori, Y., Sato, M. & Umezawa, Y. Imaging dynamics of endogenous mitochondrial RNA in single living cells. *Nature methods* 4, 413-419 (2007).
16. Armitage, B. A. Imaging of RNA in live cells. *Current opinion in chemical biology* 15, 806-812 (2011).

17. Tyagi, S. Imaging intracellular RNA distribution and dynamics in living cells. *Nature methods* 6, 331-338 (2009).
18. St Johnston, D., Brown, N. H., Gall, J. G. & Jantsch, M. A conserved double-stranded RNA-binding domain. *Proceedings of the National Academy of Sciences of the United States of America* 89, 10979-10983 (1992).
19. Bevilacqua, P. C. & Cech, T. R. Minor-groove recognition of double-stranded RNA by the double-stranded RNA-binding domain from the RNA-activated protein kinase PKR. *Biochemistry* 35, 9983-9994 (1996).
20. Nallagatla, S. R. & Bevilacqua, P. C. Nucleoside modifications modulate activation of the protein kinase PKR in an RNA structure-specific manner. *Rna* 14, 1201-1213 (2008).
21. Lundy, S. D., Zhu, W. Z., Regnier, M. & Laflamme, M. A. Structural and functional maturation of cardiomyocytes derived from human pluripotent stem cells. *Stem cells and development* 22, 1991-2002 (2013).
22. Zhang, D., et al. Tissue-engineered cardiac patch for advanced functional maturation of human ESC-derived cardiomyocytes. *Biomaterials* 34, 5813-5820 (2013).
23. Meacham, C. E. & Morrison, S. J. Tumour heterogeneity and cancer cell plasticity. *Nature* 501, 328-337 (2013).
24. Bao, G., Rhee, W. J. & Tsourkas, A. Fluorescent probes for live-cell RNA detection. *Annual review of biomedical engineering* 11, 25-47 (2009).

SEQUENCE LISTING

```
<160> NUMBER OF SEQ ID NOS: 75

<210> SEQ ID NO 1
<211> LENGTH: 184
<212> TYPE: PRT
<213> ORGANISM: Homo sapiens

<400> SEQUENCE: 1

Met Ala Gly Asp Leu Ser Ala Gly Phe Phe Met Glu Glu Leu Asn Thr
1               5                   10                  15

Tyr Arg Gln Lys Gln Gly Val Val Leu Lys Tyr Gln Glu Leu Pro Asn
            20                  25                  30

Ser Gly Pro Pro His Asp Arg Arg Phe Thr Phe Gln Val Ile Ile Asp
        35                  40                  45

Gly Arg Glu Phe Pro Glu Gly Glu Gly Arg Ser Lys Lys Glu Ala Lys
    50                  55                  60

Asn Ala Ala Ala Lys Leu Ala Val Glu Ile Leu Asn Lys Glu Lys Lys
65                  70                  75                  80

Ala Val Ser Pro Leu Leu Leu Thr Thr Thr Asn Ser Ser Glu Gly Leu
                85                  90                  95

Ser Met Gly Asn Tyr Ile Gly Leu Ile Asn Arg Ile Ala Gln Lys Lys
            100                 105                 110

Arg Leu Thr Val Asn Tyr Glu Gln Cys Ala Ser Gly Val His Gly Pro
        115                 120                 125

Glu Gly Phe His Tyr Lys Cys Lys Met Gly Gln Lys Glu Tyr Ser Ile
    130                 135                 140

Gly Thr Gly Ser Thr Lys Gln Glu Ala Lys Gln Leu Ala Ala Lys Leu
145                 150                 155                 160

Ala Tyr Leu Gln Ile Leu Ser Glu Glu Thr Ser Val Lys Ser Asp Tyr
                165                 170                 175

Leu Ser Ser Gly Ser Phe Ala Thr
            180

<210> SEQ ID NO 2
<211> LENGTH: 205
<212> TYPE: PRT
<213> ORGANISM: Artificial Sequence
<220> FEATURE:
<223> OTHER INFORMATION: Description of Artificial Sequence: Synthetic
      polynucleotide

<400> SEQUENCE: 2

Met Gly Ser Ser His His His His His His Ser Ser Gly Leu Val Pro
1               5                   10                  15
```

```
Arg Gly Ser His Met Met Ala Gly Asp Leu Ser Ala Gly Phe Met
            20                  25                  30

Glu Glu Leu Asn Thr Tyr Arg Gln Lys Gln Gly Val Val Leu Lys Tyr
         35                  40                  45

Gln Glu Leu Pro Asn Ser Gly Pro Pro His Asp Arg Arg Phe Thr Phe
 50                  55                  60

Gln Val Ile Ile Asp Gly Arg Glu Phe Pro Glu Gly Glu Gly Arg Ser
 65                  70                  75                  80

Lys Lys Glu Ala Lys Asn Ala Ala Ala Lys Leu Ala Val Glu Ile Leu
                 85                  90                  95

Asn Lys Glu Lys Lys Ala Val Ser Pro Leu Leu Leu Thr Thr Thr Asn
            100                 105                 110

Ser Ser Glu Gly Leu Ser Met Gly Asn Tyr Ile Gly Leu Ile Asn Arg
        115                 120                 125

Ile Ala Gln Lys Lys Arg Leu Thr Val Asn Tyr Glu Gln Cys Ala Ser
    130                 135                 140

Gly Val His Gly Pro Glu Gly Phe His Tyr Lys Cys Lys Met Gly Gln
145                 150                 155                 160

Lys Glu Tyr Ser Ile Gly Thr Gly Ser Thr Lys Gln Glu Ala Lys Gln
                165                 170                 175

Leu Ala Ala Lys Leu Ala Tyr Leu Gln Ile Leu Ser Glu Glu Thr Ser
            180                 185                 190

Val Lys Ser Asp Tyr Leu Ser Ser Gly Ser Phe Ala Thr
        195                 200                 205

<210> SEQ ID NO 3
<211> LENGTH: 68
<212> TYPE: PRT
<213> ORGANISM: Drosophila melanogaster

<400> SEQUENCE: 3

Thr Pro Met Cys Leu Val Asn Glu Leu Ala Arg Tyr Asn Lys Ile Thr
1               5                  10                  15

His Gln Tyr Arg Leu Thr Glu Glu Arg Gly Pro Ala His Cys Lys Thr
            20                  25                  30

Phe Thr Val Thr Leu Met Leu Gly Asp Glu Glu Tyr Ser Ala Asp Gly
        35                  40                  45

Phe Lys Ile Lys Lys Ala Gln His Leu Ala Ala Ser Lys Ala Ile Glu
    50                  55                  60

Glu Thr Met Tyr
65

<210> SEQ ID NO 4
<211> LENGTH: 68
<212> TYPE: PRT
<213> ORGANISM: Drosophila melanogaster

<400> SEQUENCE: 4

Ser Pro Ile Ser Gln Val His Glu Ile Gly Ile Lys Arg Asn Met Thr
1               5                  10                  15

Val His Phe Lys Val Leu Arg Glu Glu Gly Pro Ala His Met Lys Asn
            20                  25                  30

Phe Ile Thr Ala Cys Ile Val Gly Ser Ile Val Thr Glu Gly Glu Gly
        35                  40                  45

Asn Gly Lys Lys Val Ser Lys Lys Arg Ala Ala Glu Lys Met Leu Val
    50                  55                  60
```

Glu Leu Gln Lys
65

<210> SEQ ID NO 5
<211> LENGTH: 71
<212> TYPE: PRT
<213> ORGANISM: Drosophila melanogaster

<400> SEQUENCE: 5

Asn Pro Ile Thr Lys Leu Ile Gln Leu Gln Gln Thr Arg Lys Glu Lys
1               5                   10                  15

Glu Pro Ile Phe Glu Leu Ile Ala Lys Asn Gly Asn Glu Thr Ala Arg
            20                  25                  30

Arg Arg Glu Phe Val Met Glu Val Ser Ala Ser Gly Ser Thr Ala Arg
        35                  40                  45

Gly Thr Gly Asn Ser Lys Lys Leu Ala Lys Arg Asn Ala Ala Gln Ala
    50                  55                  60

Leu Phe Glu Leu Leu Glu Ala
65                  70

<210> SEQ ID NO 6
<211> LENGTH: 69
<212> TYPE: PRT
<213> ORGANISM: Homo sapiens

<400> SEQUENCE: 6

Phe Phe Met Glu Glu Leu Asn Thr Tyr Arg Gln Lys Gln Gly Val Val
1               5                   10                  15

Leu Lys Tyr Gln Glu Leu Pro Asn Ser Gly Pro Pro His Asp Arg Arg
            20                  25                  30

Phe Thr Phe Gln Val Ile Ile Asp Gly Arg Glu Phe Pro Glu Gly Glu
        35                  40                  45

Gly Arg Ser Lys Lys Glu Ala Lys Asn Ala Ala Ala Lys Leu Ala Val
    50                  55                  60

Glu Ile Leu Asn Lys
65

<210> SEQ ID NO 7
<211> LENGTH: 68
<212> TYPE: PRT
<213> ORGANISM: Homo sapiens

<400> SEQUENCE: 7

Asn Tyr Ile Gly Leu Ile Asn Arg Ile Ala Gln Lys Lys Arg Leu Thr
1               5                   10                  15

Val Asn Tyr Glu Gln Cys Ala Ser Gly Val His Gly Pro Glu Gly Phe
            20                  25                  30

His Tyr Lys Cys Lys Met Gly Gln Lys Glu Tyr Ser Ile Gly Thr Gly
        35                  40                  45

Ser Thr Lys Gln Glu Ala Lys Gln Leu Ala Ala Lys Leu Ala Tyr Leu
    50                  55                  60

Gln Ile Leu Ser
65

<210> SEQ ID NO 8
<211> LENGTH: 68
<212> TYPE: PRT
<213> ORGANISM: Homo sapiens

<400> SEQUENCE: 8

-continued

Thr Pro Ile Gln Val Leu His Glu Tyr Gly Met Lys Thr Lys Asn Ile
1               5                   10                  15

Pro Val Tyr Glu Cys Glu Arg Ser Asp Val Gln Ile His Val Pro Thr
                20                  25                  30

Phe Thr Phe Arg Val Thr Val Gly Asp Ile Thr Cys Thr Gly Glu Gly
                35                  40                  45

Thr Ser Lys Lys Leu Ala Lys His Arg Ala Ala Glu Ala Ala Ile Asn
        50                  55                  60

Ile Leu Lys Ala
65

<210> SEQ ID NO 9
<211> LENGTH: 69
<212> TYPE: PRT
<213> ORGANISM: Homo sapiens

<400> SEQUENCE: 9

Asn Pro Ile Gly Ser Leu Gln Glu Leu Ala Ile His His Gly Trp Arg
1               5                   10                  15

Leu Pro Glu Tyr Thr Leu Ser Gln Glu Gly Gly Pro Ala His Lys Arg
                20                  25                  30

Glu Tyr Thr Thr Ile Cys Arg Leu Glu Ser Phe Met Glu Thr Gly Lys
                35                  40                  45

Gly Ala Ser Lys Lys Gln Ala Lys Arg Asn Ala Ala Glu Lys Phe Leu
        50                  55                  60

Ala Lys Phe Ser Asn
65

<210> SEQ ID NO 10
<211> LENGTH: 68
<212> TYPE: PRT
<213> ORGANISM: Xenopus leavis

<400> SEQUENCE: 10

Thr Pro Ile Gln Leu Leu His Glu Phe Gly Thr Lys Thr Gly Asn His
1               5                   10                  15

Pro Val Tyr Thr Leu Glu Lys Ala Glu Gly Gln Ala His Asn Pro Ser
                20                  25                  30

Phe Thr Phe Arg Leu Val Ile Gly Asp Ile Thr Ser Leu Gly Glu Gly
                35                  40                  45

Pro Ser Lys Lys Thr Pro Lys Gln Lys Ala Ala Glu Phe Ala Leu Asn
        50                  55                  60

Ile Leu Arg Gly
65

<210> SEQ ID NO 11
<211> LENGTH: 69
<212> TYPE: PRT
<213> ORGANISM: Xenopus leavis

<400> SEQUENCE: 11

Asn Pro Val Gly Ser Leu Gln Glu Leu Ala Val Gln Lys Gly Trp Arg
1               5                   10                  15

Leu Pro Glu Tyr Thr Val Ala Gln Glu Ser Gly Pro Pro His Lys Arg
                20                  25                  30

Glu Phe Thr Ile Thr Cys Arg Val Glu Thr Phe Val Glu Thr Gly Ser
                35                  40                  45

```
Gly Thr Ser Lys Gln Val Ala Lys Arg Val Ala Ala Glu Lys Leu Leu
        50                  55                  60
Thr Lys Phe Lys Thr
 65
```

<210> SEQ ID NO 12
<211> LENGTH: 68
<212> TYPE: PRT
<213> ORGANISM: Homo sapiens

<400> SEQUENCE: 12

```
Thr Pro Ile Ser Leu Leu Gln Glu Tyr Gly Thr Arg Ile Gly Lys Thr
  1               5                  10                  15
Pro Val Tyr Asp Leu Leu Lys Ala Glu Gly Gln Ala His Gln Pro Asn
             20                  25                  30
Phe Thr Phe Arg Val Thr Val Gly Asp Thr Ser Cys Thr Gly Gln Gly
         35                  40                  45
Pro Ser Lys Lys Ala Ala Lys His Lys Ala Ala Glu Val Ala Leu Lys
     50                  55                  60
His Leu Lys Gly
 65
```

<210> SEQ ID NO 13
<211> LENGTH: 69
<212> TYPE: PRT
<213> ORGANISM: Homo sapiens

<400> SEQUENCE: 13

```
Asn Pro Val Gly Ala Leu Gln Glu Leu Val Val Gln Lys Gly Trp Arg
  1               5                  10                  15
Leu Pro Glu Tyr Thr Val Thr Gln Glu Ser Gly Pro Ala His Arg Lys
             20                  25                  30
Glu Phe Thr Met Thr Cys Arg Val Glu Arg Phe Ile Glu Ile Gly Ser
         35                  40                  45
Gly Thr Ser Lys Lys Leu Ala Lys Arg Asn Ala Ala Lys Met Leu
     50                  55                  60
Leu Arg Val His Thr
 65
```

<210> SEQ ID NO 14
<211> LENGTH: 68
<212> TYPE: PRT
<213> ORGANISM: Homo sapiens

<400> SEQUENCE: 14

```
Ser Glu Val Cys Ile Leu His Glu Tyr Met Gln Arg Val Leu Lys Val
  1               5                  10                  15
Arg Pro Val Tyr Asn Phe Phe Glu Cys Glu Asn Pro Ser Glu Pro Phe
             20                  25                  30
Gly Ala Ser Val Thr Ile Asp Gly Val Thr Tyr Gly Ser Gly Thr Ala
         35                  40                  45
Ser Ser Lys Lys Leu Ala Lys Asn Lys Ala Ala Arg Ala Thr Leu Glu
     50                  55                  60
Ile Leu Ile Pro
 65
```

<210> SEQ ID NO 15
<211> LENGTH: 68
<212> TYPE: PRT

-continued

<213> ORGANISM: Homo sapiens

<400> SEQUENCE: 15

Ser Pro Tyr Gln Ile Leu His Glu Cys Leu Lys Arg Asn His Gly Met
1               5                   10                  15

Gly Asp Thr Ser Ile Lys Phe Glu Val Val Pro Gly Lys Asn Gln Lys
            20                  25                  30

Ser Glu Tyr Val Met Ala Cys Gly Lys His Thr Val Arg Gly Trp Cys
        35                  40                  45

Lys Asn Lys Arg Val Gly Lys Gln Leu Ala Ser Gln Lys Ile Leu Gln
    50                  55                  60

Leu Leu His Pro
65

<210> SEQ ID NO 16
<211> LENGTH: 69
<212> TYPE: PRT
<213> ORGANISM: Homo sapiens

<400> SEQUENCE: 16

Asn Pro Ile Ser Gly Leu Leu Glu Tyr Ala Gln Phe Ala Ser Gln Thr
1               5                   10                  15

Cys Glu Phe Asn Met Ile Glu Gln Ser Gly Pro Pro His Glu Pro Arg
            20                  25                  30

Phe Lys Phe Gln Val Val Ile Asn Gly Arg Glu Phe Pro Pro Ala Glu
        35                  40                  45

Ala Gly Ser Lys Lys Val Ala Lys Gln Asp Ala Ala Met Lys Ala Met
    50                  55                  60

Thr Ile Leu Leu Glu
65

<210> SEQ ID NO 17
<211> LENGTH: 69
<212> TYPE: PRT
<213> ORGANISM: Homo sapiens

<400> SEQUENCE: 17

Ser Pro Val Thr Thr Leu Leu Glu Cys Met His Lys Leu Gly Asn Ser
1               5                   10                  15

Cys Glu Phe Arg Leu Leu Ser Lys Glu Gly Pro Ala His Glu Pro Lys
            20                  25                  30

Phe Gln Tyr Cys Val Ala Val Gly Ala Gln Thr Phe Pro Ser Val Ser
        35                  40                  45

Ala Pro Ser Lys Lys Val Ala Lys Gln Met Ala Ala Glu Glu Ala Met
    50                  55                  60

Lys Ala Leu His Gly
65

<210> SEQ ID NO 18
<211> LENGTH: 64
<212> TYPE: PRT
<213> ORGANISM: Homo sapiens

<400> SEQUENCE: 18

Asn Ala Leu Met Gln Leu Asn Glu Ile Lys Pro Gly Leu Gln Tyr Thr
1               5                   10                  15

Leu Leu Ser Gln Thr Gly Pro Val His Ala Pro Leu Phe Val Met Ser
            20                  25                  30

Val Glu Val Asn Gly Gln Val Phe Glu Gly Ser Gly Pro Thr Lys Lys
            35                  40                  45

Lys Ala Lys Leu His Ala Ala Glu Lys Ala Leu Arg Ser Phe Val Gln
    50                  55                  60

<210> SEQ ID NO 19
<211> LENGTH: 64
<212> TYPE: PRT
<213> ORGANISM: Homo sapiens

<400> SEQUENCE: 19

Asn Pro Val Met Ile Leu Asn Glu Leu Arg Pro Gly Leu Lys Tyr Asp
1               5                   10                  15

Phe Leu Ser Glu Ser Gly Glu Ser His Ala Lys Ser Phe Val Met Ser
            20                  25                  30

Val Val Val Asp Gly Gln Phe Phe Glu Gly Ser Gly Arg Asn Lys Lys
        35                  40                  45

Leu Ala Lys Ala Arg Ala Ala Gln Ser Ala Leu Ala Ala Ile Phe Asn
    50                  55                  60

<210> SEQ ID NO 20
<211> LENGTH: 64
<212> TYPE: PRT
<213> ORGANISM: Drosophila melanogaster

<400> SEQUENCE: 20

Asn Thr Val Ala Met Leu Asn Glu Leu Arg His Gly Leu Ile Tyr Lys
1               5                   10                  15

Leu Glu Ser Gln Thr Gly Pro Val His Ala Pro Leu Phe Thr Ile Ser
            20                  25                  30

Val Glu Val Asp Gly Gln Lys Tyr Leu Gly Gln Gly Arg Ser Lys Lys
        35                  40                  45

Val Ala Arg Ile Glu Ala Ala Thr Ala Leu Arg Ser Phe Ile Gln
    50                  55                  60

<210> SEQ ID NO 21
<211> LENGTH: 64
<212> TYPE: PRT
<213> ORGANISM: Drosophila melanogaster

<400> SEQUENCE: 21

Gly Pro Val Met Leu Leu Tyr Glu Leu Phe Asn Asp Val Asn Phe Glu
1               5                   10                  15

Cys Ile Asn Ile Asp Gly Ala Gln Asn Asn Cys Arg Phe Lys Met Thr
            20                  25                  30

Val Thr Ile Asn Glu Lys Lys Phe Asp Gly Thr Gly Pro Ser Lys Lys
        35                  40                  45

Thr Ala Lys Asn Ala Ala Ala Lys Ala Ala Leu Ala Ser Leu Cys Asn
    50                  55                  60

<210> SEQ ID NO 22
<211> LENGTH: 63
<212> TYPE: PRT
<213> ORGANISM: Homo sapiens

<400> SEQUENCE: 22

Ser Pro Val Arg Glu Leu Leu Glu Met Glu Pro Glu Thr Ala Lys Phe
1               5                   10                  15

Ser Pro Ala Glu Arg Thr Tyr Asp Gly Lys Val Arg Val Thr Val Glu
            20                  25                  30

```
Val Val Gly Lys Gly Lys Phe Lys Gly Val Gly Arg Ser Tyr Arg Ile
            35                  40                  45

Ala Lys Ser Ala Ala Ala Arg Arg Ala Leu Arg Ser Leu Lys Ala
 50                  55                  60

<210> SEQ ID NO 23
<211> LENGTH: 69
<212> TYPE: PRT
<213> ORGANISM: Saccharomyces cerevisiae

<400> SEQUENCE: 23

Asn Ala Lys Arg Gln Leu Tyr Ser Leu Ile Gly Tyr Ala Ser Leu Arg
  1               5                  10                  15

Leu His Tyr Val Thr Val Lys Lys Pro Thr Ala Val Asp Pro Asn Ser
             20                  25                  30

Ile Val Glu Cys Arg Val Gly Asp Gly Thr Val Leu Gly Thr Gly Val
         35                  40                  45

Gly Arg Asn Ile Lys Ile Ala Gly Ile Arg Ala Ala Glu Asn Ala Leu
     50                  55                  60

Arg Asp Lys Lys Met
 65

<210> SEQ ID NO 24
<211> LENGTH: 71
<212> TYPE: PRT
<213> ORGANISM: Escherichia coli

<400> SEQUENCE: 24

Asp Pro Lys Thr Arg Leu Gln Glu Tyr Leu Gln Gly Arg His Leu Pro
  1               5                  10                  15

Leu Pro Thr Tyr Leu Val Val Gln Val Arg Gly Glu Ala His Asp Gln
             20                  25                  30

Glu Phe Thr Ile His Cys Gln Val Ser Gly Leu Ser Glu Pro Val Val
         35                  40                  45

Gly Thr Gly Ser Ser Arg Arg Lys Ala Glu Gln Ala Ala Ala Glu Gln
     50                  55                  60

Ala Leu Lys Lys Leu Glu Leu
 65                  70

<210> SEQ ID NO 25
<211> LENGTH: 69
<212> TYPE: PRT
<213> ORGANISM: Aquifex aeolicus

<400> SEQUENCE: 25

Asp Tyr Lys Thr Ile Leu Gln Glu Ile Thr Gln Lys Arg Trp Lys Glu
  1               5                  10                  15

Arg Pro Glu Tyr Arg Leu Ile Ser Val Glu Gly Pro His His Lys Lys
             20                  25                  30

Lys Phe Ile Val Glu Ala Lys Ile Lys Glu Tyr Arg Thr Leu Gly Glu
         35                  40                  45

Gly Lys Ser Lys Lys Glu Ala Glu Gln Arg Ala Ala Glu Glu Leu Ile
     50                  55                  60

Lys Leu Leu Glu Glu
 65

<210> SEQ ID NO 26
<211> LENGTH: 70
```

```
<212> TYPE: PRT
<213> ORGANISM: Arabidopsis thaliana

<400> SEQUENCE: 26

Val Phe Lys Ser Arg Leu Gln Glu Tyr Ala Gln Lys Tyr Lys Leu Pro
1               5                   10                  15

Thr Pro Val Tyr Glu Ile Val Lys Glu Gly Pro Ser His Lys Ser Leu
            20                  25                  30

Phe Gln Ser Thr Val Ile Leu Asp Gly Val Arg Tyr Asn Ser Leu Pro
        35                  40                  45

Gly Phe Phe Asn Arg Lys Ala Ala Glu Gln Ser Ala Ala Glu Val Ala
    50                  55                  60

Leu Arg Glu Leu Ala Lys
65                  70

<210> SEQ ID NO 27
<211> LENGTH: 70
<212> TYPE: PRT
<213> ORGANISM: Arabidopsis thaliana

<400> SEQUENCE: 27

Leu Cys Lys Asn Leu Leu Gln Glu Tyr Ala Gln Lys Met Asn Tyr Ala
1               5                   10                  15

Ile Pro Leu Tyr Gln Cys Gln Lys Val Glu Thr Leu Gly Arg Val Thr
            20                  25                  30

Gln Phe Thr Cys Thr Val Glu Ile Gly Gly Ile Lys Tyr Thr Gly Ala
        35                  40                  45

Ala Thr Arg Thr Lys Lys Asp Ala Glu Ile Ser Ala Gly Arg Thr Ala
    50                  55                  60

Leu Leu Ala Ile Gln Ser
65                  70

<210> SEQ ID NO 28
<211> LENGTH: 73
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (10)..(18)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (22)..(27)
<223> OTHER INFORMATION: Any amino acid
<220> FEATURE:
<221> NAME/KEY: MOD_RES
<222> LOCATION: (30)..(30)
<223> OTHER INFORMATION: Any amino acid
```

```
<220> FEATURE:
<221> NAME/KEY: MOD_RES
<222> LOCATION: (32)..(34)
<223> OTHER INFORMATION: Any amino acid
<220> FEATURE:
<221> NAME/KEY: MOD_RES
<222> LOCATION: (36)..(38)
<223> OTHER INFORMATION: Any amino acid
<220> FEATURE:
<221> NAME/KEY: MOD_RES
<222> LOCATION: (40)..(40)
<223> OTHER INFORMATION: Any amino acid
<220> FEATURE:
<221> NAME/KEY: MOD_RES
<222> LOCATION: (42)..(42)
<223> OTHER INFORMATION: Any amino acid
<220> FEATURE:
<221> NAME/KEY: MOD_RES
<222> LOCATION: (44)..(49)
<223> OTHER INFORMATION: Any amino acid
<220> FEATURE:
<221> NAME/KEY: MOD_RES
<222> LOCATION: (51)..(51)
<223> OTHER INFORMATION: Any amino acid
<220> FEATURE:
<221> NAME/KEY: MOD_RES
<222> LOCATION: (53)..(53)
<223> OTHER INFORMATION: Any amino acid
<220> FEATURE:
<221> NAME/KEY: MOD_RES
<222> LOCATION: (57)..(57)
<223> OTHER INFORMATION: Any amino acid
<220> FEATURE:
<221> NAME/KEY: MOD_RES
<222> LOCATION: (60)..(61)
<223> OTHER INFORMATION: Any amino acid
<220> FEATURE:
<221> NAME/KEY: MOD_RES
<222> LOCATION: (65)..(65)
<223> OTHER INFORMATION: Any amino acid
<220> FEATURE:
<221> NAME/KEY: MOD_RES
<222> LOCATION: (68)..(69)
<223> OTHER INFORMATION: Any amino acid
<220> FEATURE:
<221> NAME/KEY: MOD_RES
<222> LOCATION: (71)..(73)
<223> OTHER INFORMATION: Any amino acid

<400> SEQUENCE: 28

Xaa Pro Xaa Xaa Xaa Leu Xaa Glu Leu Xaa Xaa Xaa Xaa Xaa Xaa
1               5                   10                  15

Xaa Xaa Pro Xaa Tyr Xaa Xaa Xaa Xaa Xaa Gly Pro Xaa His Xaa
                20                  25                  30

Xaa Xaa Phe Xaa Xaa Xaa Val Xaa Val Xaa Gly Xaa Xaa Xaa Xaa
            35                  40                  45

Xaa Gly Xaa Gly Xaa Ser Lys Lys Xaa Ala Lys Xaa Xaa Ala Ala Glu
    50                  55                  60

Xaa Ala Leu Xaa Xaa Leu Xaa Xaa Xaa
65                  70

<210> SEQ ID NO 29
<211> LENGTH: 73
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (1)..(1)
<223> OTHER INFORMATION: Any amino acid
<220> FEATURE:
```

```
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (7)..(8)
<223> OTHER INFORMATION: Any amino acid
<220> FEATURE:
<221> NAME/KEY: MOD_RES
<222> LOCATION: (10)..(18)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (22)..(34)
<223> OTHER INFORMATION: Any amino acid
<220> FEATURE:
<221> NAME/KEY: MOD_RES
<222> LOCATION: (36)..(38)
<223> OTHER INFORMATION: Any amino acid
<220> FEATURE:
<221> NAME/KEY: MOD_RES
<222> LOCATION: (40)..(40)
<223> OTHER INFORMATION: Any amino acid
<220> FEATURE:
<221> NAME/KEY: MOD_RES
<222> LOCATION: (42)..(42)
<223> OTHER INFORMATION: Any amino acid
<220> FEATURE:
<221> NAME/KEY: MOD_RES
<222> LOCATION: (44)..(49)
<223> OTHER INFORMATION: Any amino acid
<220> FEATURE:
<221> NAME/KEY: MOD_RES
<222> LOCATION: (51)..(51)
<223> OTHER INFORMATION: Any amino acid
<220> FEATURE:
<221> NAME/KEY: MOD_RES
<222> LOCATION: (53)..(53)
<223> OTHER INFORMATION: Any amino acid
<220> FEATURE:
<221> NAME/KEY: MOD_RES
<222> LOCATION: (55)..(57)
<223> OTHER INFORMATION: Any amino acid
<220> FEATURE:
<221> NAME/KEY: MOD_RES
<222> LOCATION: (59)..(61)
<223> OTHER INFORMATION: Any amino acid
<220> FEATURE:
<221> NAME/KEY: MOD_RES
<222> LOCATION: (64)..(65)
<223> OTHER INFORMATION: Any amino acid
<220> FEATURE:
<221> NAME/KEY: MOD_RES
<222> LOCATION: (68)..(69)
<223> OTHER INFORMATION: Any amino acid
<220> FEATURE:
<221> NAME/KEY: MOD_RES
<222> LOCATION: (71)..(73)
<223> OTHER INFORMATION: Any amino acid

<400> SEQUENCE: 29

Xaa Pro Xaa Xaa Xaa Leu Xaa Xaa Leu Xaa Xaa Xaa Xaa Xaa Xaa
  1               5                   10                  15

Xaa Xaa Pro Xaa Tyr Xaa Xaa Xaa Xaa Xaa Xaa Xaa Xaa Xaa Xaa
                 20                  25                  30

Xaa Xaa Phe Xaa Xaa Xaa Val Xaa Val Xaa Gly Xaa Xaa Xaa Xaa
             35                  40                  45

Xaa Gly Xaa Gly Xaa Ser Xaa Xaa Xaa Ala Xaa Xaa Xaa Ala Ala Xaa
 50                  55                  60

Xaa Ala Leu Xaa Xaa Leu Xaa Xaa Xaa
```

<210> SEQ ID NO 30
<211> LENGTH: 73
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (1)..(7)
<223> OTHER INFORMATION: Any amino acid
<220> FEATURE:
<221> NAME/KEY: MOD_RES
<222> LOCATION: (9)..(20)
<223> OTHER INFORMATION: Any amino acid
<220> FEATURE:
<221> NAME/KEY: MOD_RES
<222> LOCATION: (22)..(27)
<223> OTHER INFORMATION: Any amino acid
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (32)..(34)
<223> OTHER INFORMATION: Any amino acid
<220> FEATURE:
<221> NAME/KEY: MOD_RES
<222> LOCATION: (36)..(54)
<223> OTHER INFORMATION: Any amino acid
<220> FEATURE:
<221> NAME/KEY: MOD_RES
<222> LOCATION: (57)..(58)
<223> OTHER INFORMATION: Any amino acid
<220> FEATURE:
<221> NAME/KEY: MOD_RES
<222> LOCATION: (60)..(73)
<223> OTHER INFORMATION: Any amino acid

<400> SEQUENCE: 30

Xaa Xaa Xaa Xaa Xaa Xaa Xaa Glu Xaa Xaa Xaa Xaa Xaa Xaa Xaa Xaa
1               5                   10                  15

Xaa Xaa Xaa Xaa Tyr Xaa Xaa Xaa Xaa Xaa Xaa Gly Pro Xaa His Xaa
            20                  25                  30

Xaa Xaa Phe Xaa Xaa Xaa Xaa Xaa Xaa Xaa Xaa Xaa Xaa Xaa Xaa Xaa
        35                  40                  45

Xaa Xaa Xaa Xaa Xaa Xaa Lys Lys Xaa Xaa Lys Xaa Xaa Xaa Xaa Xaa
    50                  55                  60

Xaa Xaa Xaa Xaa Xaa Xaa Xaa Xaa Xaa
65                  70

<210> SEQ ID NO 31
<211> LENGTH: 73
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(7)
<223> OTHER INFORMATION: Any amino acid
<220> FEATURE:
<221> NAME/KEY: MOD_RES
<222> LOCATION: (9)..(20)

```
<223> OTHER INFORMATION: Any amino acid
<220> FEATURE:
<221> NAME/KEY: MOD_RES
<222> LOCATION: (22)..(27)
<223> OTHER INFORMATION: Any amino acid
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (32)..(34)
<223> OTHER INFORMATION: Any amino acid
<220> FEATURE:
<221> NAME/KEY: MOD_RES
<222> LOCATION: (36)..(54)
<223> OTHER INFORMATION: Any amino acid
<220> FEATURE:
<221> NAME/KEY: MOD_RES
<222> LOCATION: (57)..(73)
<223> OTHER INFORMATION: Any amino acid

<400> SEQUENCE: 31

Xaa Xaa Lys Xaa Xaa Xaa Xaa Glu Xaa Xaa Xaa Xaa Xaa Xaa Xaa Xaa
 1               5                  10                  15

Xaa Xaa Xaa Xaa Tyr Xaa Xaa Xaa Xaa Xaa Xaa Gly Pro Xaa His Xaa
             20                  25                  30

Xaa Xaa Phe Xaa Xaa Xaa Xaa Xaa Xaa Xaa Xaa Xaa Xaa Xaa Xaa
         35                  40                  45

Xaa Xaa Xaa Xaa Xaa Lys Lys Xaa Xaa Xaa Xaa Xaa Xaa Xaa Xaa
     50                  55                  60

Xaa Xaa Xaa Xaa Xaa Xaa Xaa Xaa Xaa
 65                  70

<210> SEQ ID NO 32
<211> LENGTH: 27
<212> TYPE: PRT
<213> ORGANISM: Unknown
<220> FEATURE:
<223> OTHER INFORMATION: Description of Unknown:
      Signal sequence peptide

<400> SEQUENCE: 32

Gly Ala Leu Phe Leu Gly Trp Leu Gly Ala Ala Gly Ser Thr Met Gly
 1               5                  10                  15

Ala Trp Ser Gln Pro Lys Lys Lys Arg Lys Val
             20                  25

<210> SEQ ID NO 33
<211> LENGTH: 16
<212> TYPE: PRT
<213> ORGANISM: Unknown
<220> FEATURE:
<223> OTHER INFORMATION: Description of Unknown:
      Signal sequence peptide

<400> SEQUENCE: 33

Ala Ala Val Ala Leu Leu Pro Ala Val Leu Leu Ala Leu Leu Ala Pro
 1               5                  10                  15

<210> SEQ ID NO 34
<211> LENGTH: 26
<212> TYPE: PRT
<213> ORGANISM: Unknown
<220> FEATURE:
<223> OTHER INFORMATION: Description of Unknown:
      Transportan peptide
```

```
<400> SEQUENCE: 34

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 35

<400> SEQUENCE: 35

000

<210> SEQ ID NO 36
<211> LENGTH: 18
<212> TYPE: PRT
<213> ORGANISM: Unknown
<220> FEATURE:
<223> OTHER INFORMATION: Description of Unknown:
      Amphiphilic model peptide

<400> SEQUENCE: 36

Lys Leu Ala Leu Lys Leu Ala Leu Lys Ala Leu Lys Ala Ala Leu Lys
1               5                   10                  15

Leu Ala

<210> SEQ ID NO 37
<211> LENGTH: 11
<212> TYPE: PRT
<213> ORGANISM: Human immunodeficiency virus 1

<400> SEQUENCE: 37

Tyr Gly Arg Lys Lys Arg Arg Gln Arg Arg Arg
1               5                   10

<210> SEQ ID NO 38
<211> LENGTH: 13
<212> TYPE: PRT
<213> ORGANISM: Human immunodeficiency virus 1

<400> SEQUENCE: 38

Gly Arg Lys Lys Arg Arg Gln Arg Arg Arg Thr Pro Gln
1               5                   10

<210> SEQ ID NO 39
<211> LENGTH: 9
<212> TYPE: PRT
<213> ORGANISM: Human immunodeficiency virus 1

<400> SEQUENCE: 39

Arg Lys Lys Arg Arg Gln Arg Arg Arg
1               5

<210> SEQ ID NO 40
<211> LENGTH: 26
<212> TYPE: PRT
<213> ORGANISM: Human herpesvirus 8

<400> SEQUENCE: 40

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25
```

```
<210> SEQ ID NO 41
<211> LENGTH: 17
<212> TYPE: PRT
<213> ORGANISM: Caiman crocodilus

<400> SEQUENCE: 41

Met Gly Leu Gly Leu His Leu Leu Val Leu Ala Ala Ala Leu Gln Gly
1               5                   10                  15

Ala

<210> SEQ ID NO 42
<211> LENGTH: 23
<212> TYPE: PRT
<213> ORGANISM: Human immunodeficiency virus 1

<400> SEQUENCE: 42

Gly Ala Leu Phe Leu Gly Phe Leu Gly Ala Ala Gly Ser Thr Met Gly
1               5                   10                  15

Ala Pro Lys Ser Lys Arg Lys
            20

<210> SEQ ID NO 43
<211> LENGTH: 16
<212> TYPE: PRT
<213> ORGANISM: Drosophila melanogaster

<400> SEQUENCE: 43

Arg Gln Ile Lys Ile Trp Phe Gln Asn Arg Arg Met Lys Trp Lys Lys
1               5                   10                  15

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 44

Xaa Arg Gly Asp Xaa
1               5

<210> SEQ ID NO 45
<211> LENGTH: 24
<212> TYPE: PRT
<213> ORGANISM: Influenza virus

<400> SEQUENCE: 45

Gly Leu Phe Glu Ala Ile Ala Gly Phe Ile Glu Asn Gly Trp Glu Gly
1               5                   10                  15

Met Ile Asp Gly Gly Gly Tyr Cys
            20

<210> SEQ ID NO 46
<211> LENGTH: 27
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 46

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 47

Ser Asp His Gln Leu Asn Pro Ala Phe
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: L-Phe or D-Phe
<220> FEATURE:
<221> NAME/KEY: MOD_RES
<222> LOCATION: (5)..(5)
<223> OTHER INFORMATION: L-Trp or D-Trp

<400> SEQUENCE: 48

Ser Phe Cys Tyr Trp Lys Thr Cys Thr
1               5

<210> SEQ ID NO 49
<211> LENGTH: 26
<212> TYPE: PRT
<213> ORGANISM: Human herpesvirus 8

<400> SEQUENCE: 49

Ala Ala Val Ala Leu Leu Pro Ala Val Leu Leu Ala Leu Leu Ala Pro
1               5                   10                  15

Ala Ala Ala Asp Gln Asn Gln Leu Met Pro
            20                  25

<210> SEQ ID NO 50
<211> LENGTH: 34
<212> TYPE: PRT
<213> ORGANISM: Herpes simplex virus

<400> SEQUENCE: 50

Asp Ala Ala Thr Ala Thr Arg Gly Arg Ser Ala Ala Ser Arg Pro Thr
1               5                   10                  15
```

Glu Arg Pro Arg Ala Pro Ala Arg Ser Ala Ser Arg Pro Arg Arg Pro
            20                  25                  30

Val Glu

<210> SEQ ID NO 51
<211> LENGTH: 16
<212> TYPE: PRT
<213> ORGANISM: Unknown
<220> FEATURE:
<223> OTHER INFORMATION: Description of Unknown:
      Grb2 binding peptide sequence

<400> SEQUENCE: 51

Arg Arg Trp Arg Arg Trp Trp Arg Arg Trp Trp Arg Arg Trp Arg Arg
1               5                   10                  15

<210> SEQ ID NO 52
<211> LENGTH: 7
<212> TYPE: PRT
<213> ORGANISM: Unknown
<220> FEATURE:
<223> OTHER INFORMATION: Description of Unknown:
      Cationic peptide

<400> SEQUENCE: 52

Arg Arg Arg Arg Arg Arg Arg
1               5

<210> SEQ ID NO 53
<211> LENGTH: 9
<212> TYPE: PRT
<213> ORGANISM: Unknown
<220> FEATURE:
<223> OTHER INFORMATION: Description of Unknown:
      Cationic peptide

<400> SEQUENCE: 53

Arg Arg Arg Arg Arg Arg Arg Arg Arg
1               5

<210> SEQ ID NO 54
<211> LENGTH: 11
<212> TYPE: PRT
<213> ORGANISM: Unknown
<220> FEATURE:
<223> OTHER INFORMATION: Description of Unknown:
      Cationic peptide

<400> SEQUENCE: 54

Arg Arg Arg Arg Arg Arg Arg Arg Arg Arg Arg
1               5                   10

<210> SEQ ID NO 55
<211> LENGTH: 10
<212> TYPE: PRT
<213> ORGANISM: Unknown
<220> FEATURE:
<223> OTHER INFORMATION: Description of Unknown:
      Cell penetrating peptide

<400> SEQUENCE: 55

Arg Pro Lys Lys Arg Lys Val Arg Arg Arg
1               5                   10

<210> SEQ ID NO 56
<211> LENGTH: 4

```
<212> TYPE: PRT
<213> ORGANISM: Unknown
<220> FEATURE:
<223> OTHER INFORMATION: Description of Unknown:
      Branched cationic peptide

<400> SEQUENCE: 56

Lys Lys Lys Lys
1

<210> SEQ ID NO 57
<211> LENGTH: 4
<212> TYPE: PRT
<213> ORGANISM: Unknown
<220> FEATURE:
<223> OTHER INFORMATION: Description of Unknown:
      Branched cationic peptide

<400> SEQUENCE: 57

Lys Trp Lys Lys
1

<210> SEQ ID NO 58
<211> LENGTH: 4
<212> TYPE: PRT
<213> ORGANISM: Unknown
<220> FEATURE:
<223> OTHER INFORMATION: Description of Unknown:
      Branched cationic peptide

<400> SEQUENCE: 58

Arg Trp Arg Arg
1

<210> SEQ ID NO 59
<211> LENGTH: 28
<212> TYPE: PRT
<213> ORGANISM: Unknown
<220> FEATURE:
<223> OTHER INFORMATION: Description of Unknown:
      Transportan peptide

<400> SEQUENCE: 59

Gly Ala Leu Phe Leu Gly Phe Leu Gly Gly Ala Ala Gly Ser Thr Met
1               5                   10                  15

Gly Ala Trp Ser Gln Pro Lys Ser Lys Arg Lys Val
            20                  25

<210> SEQ ID NO 60
<211> LENGTH: 21
<212> TYPE: PRT
<213> ORGANISM: Unknown
<220> FEATURE:
<223> OTHER INFORMATION: Description of Unknown:
      Transportan-10 peptide

<400> SEQUENCE: 60

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 61
<211> LENGTH: 26
<212> TYPE: PRT
<213> ORGANISM: Unknown
<220> FEATURE:
```

```
<223> OTHER INFORMATION: Description of Unknown:
      VT5 peptide

<400> SEQUENCE: 61

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 62
<211> LENGTH: 18
<212> TYPE: PRT
<213> ORGANISM: Unknown
<220> FEATURE:
<223> OTHER INFORMATION: Description of Unknown:
      Alpha helical amphipathic peptide

<400> SEQUENCE: 62

Lys Leu Ala Leu Lys Leu Ala Leu Lys Ala Leu Lys Ala Ala Leu Lys
1               5                   10                  15

Leu Ala

<210> SEQ ID NO 63
<211> LENGTH: 18
<212> TYPE: PRT
<213> ORGANISM: Mus sp.

<400> SEQUENCE: 63

Leu Leu Ile Ile Leu Arg Arg Arg Ile Arg Lys Gln Ala His Ala His
1               5                   10                  15

Ser Lys

<210> SEQ ID NO 64
<211> LENGTH: 16
<212> TYPE: PRT
<213> ORGANISM: Unknown
<220> FEATURE:
<223> OTHER INFORMATION: Description of Unknown:
      Islet 1 gene enhancer peptide

<400> SEQUENCE: 64

Arg Val Ile Arg Val Trp Phe Gln Asn Lys Arg Cys Lys Asp Lys Lys
1               5                   10                  15

<210> SEQ ID NO 65
<211> LENGTH: 21
<212> TYPE: PRT
<213> ORGANISM: Unknown
<220> FEATURE:
<223> OTHER INFORMATION: Description of Unknown:
      Amphipathic peptide carrier Pep-1

<400> SEQUENCE: 65

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 66
<211> LENGTH: 28
<212> TYPE: PRT
<213> ORGANISM: Mus sp.

<400> SEQUENCE: 66
```

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 67
<211> LENGTH: 16
<212> TYPE: PRT
<213> ORGANISM: Unknown
<220> FEATURE:
<223> OTHER INFORMATION: Description of Unknown:
      Penetratin peptide

<400> SEQUENCE: 67

Arg Gln Ile Lys Ile Trp Phe Gln Asn Arg Arg Met Lys Trp Lys Lys
1               5                   10                  15

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
gagtccttcc acgatacc                                                 18

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 69
ggtatcgtgg aaggactc                                                 18

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 70
ggatagcaca gcctggata                                                19

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
gggcatcggt catcttgg                                                 18

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic probe

<400> SEQUENCE: 72
gagccccctc ctagtccttc                                               20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
ggaagtcaac ttcattgtcc                                               20

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
gagtgccggc tcgcccttt                                                19

<210> SEQ ID NO 75
<211> LENGTH: 4361
<212> TYPE: DNA
<213> ORGANISM: Homo sapiens

<400> SEQUENCE: 75
agcagacgag ggcttgtgcg agaggggggcc gggcggctgc agggaaggcg gagtccaagg    60
ggaaaacgaa actgagaacc agctctcccg aagccgcggg tctccggccg gcggcggcgg   120
cggcggcggc ggcggcgcag tttgctcata cttttgtgact tgcggtcaca gtggcattca   180
gctccacact tggtagaacc acaggcacga caagcataga aacatcctaa acaatcttca   240
tcgaggcatc gaggtccatc ccaataaaaa tcaggagacc ctggctatca tagacccttag   300 tcttcgctgg tatcactcgt ctgtctgaac cagcggttgc atttttttaa gccttctttt   360
ttctctttta ccagtttctg gagcaaattc agtttgcctt cctggatttg taaattgtaa   420
tgacctcaaa actttagcag ttcttccatc tgactcaggt ttgcttctct ggcggtcttc   480
agaatcaaca tccacacttc cgtgattatc tgcgtgcatt ttggacaaag cttccaacca   540
ggatacggga agaagaaatg gctggtgatc tttcagcagg tttcttcatg gaggaactta   600
atacataccg tcagaagcag ggagtagtac ttaaatatca agaactgcct aattcaggac   660
ctccacatga taggaggttt acatttcaag ttataataga tggaagagaa tttccagaag   720
gtgaaggtag atcaaagaag gaagcaaaaa atgccgcagc caaattagct gttgagatac   780
ttaataagga aaagaaggca gttagtcctt tattattgac aacaacgaat tcttcagaag   840
gattatccat ggggaattac ataggcctta tcaatagaat tgcccagaag aaaagactaa   900
ctgtaaatta tgaacagtgt gcatcggggg tgcatgggcc agaaggattt cattataaat   960 gcaaatggg acagaaagaa tatagtattg gtacaggttc tactaaacag gaagcaaaac  1020
aattggccgc taaacttgca tatcttcaga tattatcaga agaaacctca gtgaaatctg  1080
actacctgtc ctctggttct tttgctacta cgtgtgagtc ccaaagcaac tctttagtga  1140
ccagcacact cgcttctgaa tcatcatctg aaggtgactt ctcagcagat acatcagaga  1200

```
taaattctaa cagtgacagt ttaaacagtt cttcgttgct tatgaatggt ctcagaaata    1260
atcaaaggaa ggcaaaaaga tctttggcac ccagatttga ccttcctgac atgaaagaaa    1320
caaagtatac tgtggacaag aggtttggca tggattttaa agaaatagaa ttaattggct    1380
caggtggatt tggccaagtt ttcaaagcaa aacacagaat tgacggaaag acttacgtta    1440
ttaaacgtgt taaatataat aacgagaagg cggagcgtga agtaaaagca ttggcaaaac    1500
ttgatcatgt aaatattgtt cactacaatg gctgttggga tggatttgat tatgatcctg    1560
agaccagtga tgattctctt gagagcagtg attatgatcc tgagaacagc aaaaatagtt    1620
caaggtcaaa gactaagtgc ttttcatcc aaatggaatt ctgtgataaa gggaccttgg      1680
aacaatggat tgaaaaaga gaggcgaga actagacaa agttttggct ttggaactct        1740
ttgaacaaat aacaaagg gtggattata tacattcaaa aaaattaatt catagagatc       1800
ttaagccaag taatatattc ttagtagata caaacaagt aaagattgga gactttggac      1860
ttgtaacatc tctgaaaaat gatggaaagc gaacaaggag taagggaact ttgcgataca    1920
tgagcccaga acagatttct tcgcaagact atggaaagga agtggacctc tacgctttgg    1980
ggctaattct tgctgaactt cttcatgtat gtgacactgc ttttgaaaca tcaaagtttt    2040
tcacagacct acgggatggc atcatctcag atatatttga taaaaagaa aaaactcttc      2100 tacagaaatt actctcaaag aaacctgagg atcgacctaa cacatctgaa atactaagga    2160
ccttgactgt gtggaagaaa gcccagaga aaatgaacg acacacatgt tagagccctt       2220 ctgaaaagt atcctgcttc tgatatgcag ttttcttaa attatctaaa atctgctagg       2280
gaatatcaat agatatttac cttttatttt aatgtttcct ttaattttt actatttta      2340 ctaatctttc tgcagaaaca gaaaggtttt cttctttttg cttcaaaaac attcttacat    2400
tttacttttt cctggctcat ctctttattc ttttttttt tttaaagaca gagtctcgct      2460
ctgttgccca ggctggagtg caatgacaca gtcttggctc actgcaactt ctgcctcttg    2520
ggttcaagtg attctcctgc ctcagcctcc tgagtagctg gattacaggc atgtgccacc    2580
cacccaacta ttttgtgt ttttaataaa gacagggttt caccatgttg gccaggctgg      2640
tctcaaactc ctgacctcaa gtaatccacc tgcctcggcc tcccaaagtg ctgggattac    2700
agggatgagc caccgcgccc agcctcatct ctttgttcta agatggaaa aaccaccccc     2760 aaatttctt tttatactat taatgaatca atcaattcat atctatttat taaatttcta     2820
ccgcttttag gccaaaaaaa tgtaagatcg ttctctgcct cacatagctt acaagccagc    2880
tggagaaata tggtactcat taaaaaaaaa aaaaaagtg atgtacaacc acttcggaaa     2940
acaatttggc attatctagt aaagttgaat ccatgtatac ccacatagct atcaattcta    3000
ttcctacata cgtgcttaca agaatgtcca taaaaccctg tttataatag ccaaaagaac    3060
agggaacaac cataatgcac atcaaaagaa gaatggatta aaaaaattat attcacacac    3120
aggagtacta tatagtattg aaaacaattg aagtacagct aaatgtaata acgtaacaca    3180
atacaactct cagaaacata atgttaagcg aacaaagcag gttttcagaa aatatatgca    3240
gaataattcc atttatataa agttccagag catgcaaaac taaatcattt tgtataaaaa    3300
acccaacaaa tgtgatgaga caataatggg aaggaaggga atgagaaata ttaaattctg    3360
gatggtggtt atctttgagg gaggggaatg atgtgattgg ggaaatggac tttcaaaggt    3420
aatggtaact tccttaagct ggatggtagg tccactagtg tttgctgcat agttatacct    3480
tttatcttaa atacatttg tatctattgt aacaaccact ttaaagacaa ccgtgctgta     3540
```

```
aggcagtagc taaaaacaga aaatagtcca tcgggaaggg taagatggct ttctgctgag    3600
cacagggcta gaagtgacag cccagtgggc cttccaacta tatgccaggg tgttagatga    3660
gtagagagga gaccacccag gaagtctgga caagggtct ggcatgagct ctggagaaga    3720
tatatttgag gaacatgggg tatgctagtt tgttgtcctg aattgctgta gagaagataa    3780
tttaaattgc atcttagaag acgaccctga gggtgaattt caacttaggg caattgtttt    3840
agtttgtttc ttattggttt aaatggatac ttgaagctgg ataatttata aggaaaagag    3900
atttatatga cttacagttc tgcaggctgt acaagaaaca tggcaccagc atctgcttct    3960
tccccggctg cttccactca tggtggaagg tgaaggggag ccggatgtgc agagatcata    4020
tggcaagaga ggaagcaaga gagcgaggga gaaggtgcca ggctcttttt aaataaccgg    4080
ctcttgaggg aactaataga ttgagaactc cttgcttctc ctccccagca caccccaccc    4140
ccagggacgg cattaatgta ttcatgaggg gtcttccccc atgacccaaa cacctcccat    4200
caggccccac ctccaacact gggatcaaat ttcaacatga gattttgggg gacaaacatg    4260
caaactatag cagcaaccag ctaccattct aaaactgcca tatgatttta ggatttttaa    4320
aaagggccaa atttaggtta agcaaaaaaa aaaaaaaaa a                         4361
```

The invention claimed is:

1. A method for detection of the expression of one or more genes of interest in a living cell, comprising the steps of:
   a. providing a cell with at least one RNA binding probe (RBP) which specifically hybridizes to a target mRNA expressed by a gene of interest in the cell to form a duplex, and a polypeptide which binds to a duplex, wherein the polypeptide is labeled with, or fused to at least a first dye, and
   wherein the at least one RNA binding probe is labeled with at least a second dye,
   wherein the first and second dyes are spectrally paired such that when juxtapositioned together, allows fluorescence resonance energy transfer (FRET) and detectable change of fluorescence,
   b. allowing the RNA binding probe to hybridize to the target mRNA to form the duplex,
   c. measuring fluorescence of the cell and detecting a change in fluorescence when the dsRBP-domain binds to the duplex, thereby detecting gene expression of the gene of interest in the living cell.

2. The method of claim 1, wherein the RNA binding probe comprises a nucleic acid sequence substantially complementary to the target mRNA of the gene of interest.

3. The method of claim 1, wherein the RNA binding probe is selected from the group consisting of: a nucleic acid or nucleic acid analogue, RNA, modified RNA, DNA, ssDNA or a modified nucleic acid.

4. The method of claim 1, wherein the duplex is selected from the group consisting of: a dsRNA duplex, a heteroduplex comprising the target mRNA and ssDNA or LNA or nucleic acid analogue, a double stranded RNA (dsRNA) duplex, where the RNA binding probe is a RNA or modified RNA.

5. The method of claim 1, wherein the polypeptide which binds to the duplex comprises a double stranded RNA binding domain (dsRBD).

6. The method of claim 1, wherein the dsRBD comprises dsRBD selected from any of the following double stranded RNA binding proteins (dsRBP): protein kinase R (PKR), ADAD2, ADAR1, ADAR2, TRBP2, Stau1, Dicer, X1RBPA, DGCR8, NFAR1, NFAR2, SPNR, RHA, NREBP/SON, TENR, RDE1, Kanadaptin, HYL1 or RNaseIII.

7. The method of claim 1, wherein the dsRBD comprises any of the following:
   i. SEQ ID NO: 1 or a protein that has at least 80% amino acid sequence identity to SEQ ID NO: 1;
   ii. a consensus sequence of SEQ ID NO: 28.

8. The method of claim 1, wherein the method comprises providing the cell with any of the following:
   a.—at least 2 RNA binding probes, wherein each RNA binding probe hybridizes to a different target mRNA expressed by a gene of interest in the cell, and wherein the second dye of each RNA binding probe has a different spectral pairing with the first dye that is fused to, or labelled on the polypeptide;
   b. at least 3-5 RNA binding probes, wherein each RNA binding probe hybridizes to a different target mRNA expressed by a gene of interest in the cell, and wherein the second dye of each RNA binding probe has a different spectral pairing with the first dye that is fused to, or labelled on the polypeptide; or
   c. at least 6-10 RNA binding probes, wherein each RNA binding probe hybridizes to a different target mRNA expressed by a gene of interest in the cell, and wherein the second dye of each RNA binding probe has a different spectral pairing with the first dye that is fused to, or labelled on the polypeptide.

9. The method of claim 1, wherein the method comprises any of the following:
   a. the first dye is a donor dye and the second dye is an acceptor dye;
   b. the first dye is an acceptor dye and the second dye is a donor dye;
   wherein the donor dye is a fluorescent donor and the acceptor dye is a fluorescent acceptor.

10. The method of claim 9, wherein the fluorophore donor is selected from a fluorescent protein or a fluorescent dye molecule, wherein
   (i) a fluorescent protein is selected from the group consisting of a. a blue fluorescent protein, selected from the group consisting of EBFP, EBFP2, and imTagBFP,
b. a cyan fluorescent protein, selected from the group consisting of ECFP, mECFP, mTurquoise, AmCyan1, Midori-lshi Cyan, TagCFP and mTFP1 (Teal),
c. a yellow fluorescent protein, selected from the group consisting of YPet, ZsYellow1 and mBanana,
d. an orange fluorescent protein, selected from the group consisting of Kusabira Orange, Kusabira Orange2, dTomato, dTomato-Tandem, TagRFP, TagRFP-T, DsRed, DsRed2, DsRed-Express (T1), DsRed-Monomer and mTangerine,
e. a red fluorescent protein, selected from the group consisting of mRuby, mApple, mStrawberry, AsRed2, mRFP1, JRed, HcRed1, mRaspberry, dKeima-Tandem, HcRed-Tandem, mPlum and AQ143,
f. a green fluorescent protein (GFP), selected from the group consisting of EGFP, Superfolder GFP, Azami Green, mWasabi, TagGFP, TurboGFP, AcGFP, ZsGreen and T-Sapphire,
(ii) a fluorescent dye molecule is selected from the group consisting of
a. an acridine, selected from: acridine orange or acridine yellow,
b. a cyanine, selected from: Cy2, Cy3, Cy3B, Cy3.5, Cy5, Cy5.5, Cy7,
c. a fluorone, selected from: Fluorescein, Carboxyfluorescein, Dichlorofluorescein, Eosin, Eosin B, Eosin Y or Erythrosine,
d. an oxazine, selected from: Cresyl violet, Nile blue or Nile red,
e. a phenanthridine, selected from: Ethidium bromide, or Propidium iodide, and
f. a rhodamine, selected from: Rhodamine, Rhodamine 123, Rhodamine 6G, Rhodamine B, Auramine, Sulforhodamine 101, Sulforhodamine.

11. The method of claim 9, wherein the fluorophore acceptor is selected from the group consisting of:
(i) an acridine, selected from acridine orange or acridine yellow,
(ii) a cyanine, selected from Cy2, Cy3, Cy3B, Cy3.5, Cy5, Cy5.5 or Cy7,
(iii) a fluorone, selected from Fluorescein, Carboxyfluorescein, Dichlorofluorescein, Eosin, Eosin B, Eosin Y or Erythrosine,
(iv) an oxazine selected from Cresyl violet, Nile blue or Nile red,
(v) a phenanthridine selected from ethidium bromide, or propidium iodide, and
(vi) a rhodamine selected from Rhodamine, Rhodamine 123, Rhodamine 6G,
(vii) Rhodamine B, Auramine, Sulforhodamine 101, or Sulforhodamine B;
(viii) a dark quencher.

12. The method of claim 1, wherein the spectrally paired first and second dyes are a spectrally paired fluorophore donor and fluorophore acceptor, or a spectrally paired fluorophore donor and a dark quencher selected from the group consisting of:
a. a protein-protein pair selected from the group consisting of CyPet-YPet, mTurquoise-Ypet,
b. a protein-organic dye pair selected from the group consisting of GFP-Cy3 and EGFP-Cy3,
c. organic dye-organic-dye pairs, selected from the group consisting of Dabcyl-Edans and Dabsyl-Edans, fluorescein.

* * * * *